United States Patent
Lee et al.

(10) Patent No.: US 11,125,745 B2
(45) Date of Patent: Sep. 21, 2021

(54) MAGNETIC ELECTROCHEMICAL SENSING

(71) Applicants: The General Hospital Corporation, Boston, MA (US); The Brigham and Women's Hospital, Inc., Boston, MA (US)

(72) Inventors: Hakho Lee, Acton, MA (US); Ralph Weissleder, Peabody, MA (US); Sangmoo Jeong, New York, NY (US); Jongmin Park, Cambridge, MA (US); Cesar Castro, Reading, MA (US); Hsing-Ying Lin, Kaohsiung (TW); Jamil Azzi, Chestnut Hill, MA (US)

(73) Assignees: The General Hospital Corporation, Boston, MA (US); The Brigham and Women's Hospital, Inc., Boston, MA (US)

(*) Notice: Subject to any disclaimer, the term of this patent is extended or adjusted under 35 U.S.C. 154(b) by 258 days.

(21) Appl. No.: 16/073,540

(22) PCT Filed: Jan. 27, 2017

(86) PCT No.: PCT/US2017/015433
§ 371 (c)(1),
(2) Date: Jul. 27, 2018

(87) PCT Pub. No.: WO2017/132564
PCT Pub. Date: Aug. 3, 2017

(65) Prior Publication Data
US 2019/0346434 A1    Nov. 14, 2019

Related U.S. Application Data

(60) Provisional application No. 62/339,519, filed on May 20, 2016, provisional application No. 62/288,254, (Continued)

(51) Int. Cl.
*G01N 33/543* (2006.01)
*G01N 27/327* (2006.01)

(52) U.S. Cl.
CPC ... *G01N 33/54333* (2013.01); *G01N 27/3271* (2013.01)

(58) Field of Classification Search
CPC .......... G01N 33/5433; G01N 33/5434; G01N 33/5438; G01N 33/54386; G01N 33/547;
(Continued)

(56) References Cited

U.S. PATENT DOCUMENTS 5,509,410 A    4/1996    Hill et al.
5,837,144 A    11/1998   Bienhaus et al.
(Continued)

FOREIGN PATENT DOCUMENTS

CN    101892294 A    11/2010
CN    102095848 A    6/2011
(Continued)

OTHER PUBLICATIONS

J. Allergy Clin Immunol, 2006, 719-724 (Year: 2006).*
(Continued)

*Primary Examiner* — Gurpreet Kaur
(74) *Attorney, Agent, or Firm* — Fish & Richardson P.C.

(57) ABSTRACT

Target analyte detection devices include a housing having a potentiostat and a microcontroller coupled to the potentiostat. The device also includes a substrate having a plurality of electrodes on a first surface of the substrate. A first set of electrodes of the plurality of electrodes defines a first sample detection region. The substrate is removably attachable to the housing such that the first set of electrodes is coupled to the potentiostat upon attaching the substrate to the housing. The device also includes a magnet assembly couplable to a second surface of the substrate. The magnet
(Continued)

assembly includes a magnet positioned in the magnet assembly such that a magnetic field from the magnet extends through the substrate and the first set of electrodes into an area above the first sample detection region upon coupling the magnet assembly to the substrate.

28 Claims, 43 Drawing Sheets

Related U.S. Application Data filed on Jan. 28, 2016, provisional application No. 62/287,719, filed on Jan. 27, 2016.

(58) Field of Classification Search
CPC ............... G01N 33/535; G01N 33/536; G01N 33/54326; G01N 27/3273; G01N 27/28
See application file for complete search history.

(56) References Cited

U.S. PATENT DOCUMENTS

| | | | | |
|---|---|---|---|---|
| 6,403,038 | B1* | 6/2002 | Heermann | B03C 1/0332 422/527 |
| 2009/0118604 | A1 | 5/2009 | Phan et al. | |
| 2011/0098937 | A1 | 4/2011 | Cummins | |
| 2011/0172550 | A1 | 7/2011 | Martin et al. | |
| 2013/0178383 | A1* | 7/2013 | Spetzler | G01N 1/4077 506/9 |
| 2014/0069213 | A1 | 3/2014 | Yong | |
| 2015/0068894 | A1 | 3/2015 | Khattak et al. | |
| 2017/0153233 | A1* | 6/2017 | Pividori Gurgo | C07K 14/415 |

FOREIGN PATENT DOCUMENTS

| | | |
|---|---|---|
| CN | 103308675 A | 9/2013 |
| CN | 104854456 A | 8/2015 |
| WO | WO 2014/060454 | 4/2014 |
| WO | WO 2014/147049 | 9/2014 |
| WO | WO 2014/207270 | 12/2014 |
| WO | WO 2015/085262 | 6/2015 |

OTHER PUBLICATIONS

European Extended Search Report in European Appl. No. 17745010. 3, dated Jun. 13, 2019, 9 pages.
Gonzalez-Techera et al, "Development of a highly sensitive non-competitive electrochemical immunosensor for the detection of atrazine by phage anti-inmunocomplex assay," Biosensors and Bioelectronics, 2014, 64:650-656.
Office Action in Singapore Appln. No. 11201806385P, dated Nov. 15, 2019, 8 pages.
Aldovini et al., "M-CAM expression as marker of poor prognosis in epithelial ovarian cancer," Int J Cancer, 2006, 119: 1920-1926.
Ambrosi et al., "Enhanced gold nanoparticle based ELISA for a breast cancer biomarker," Anal Chem, 2010, 82: 1151-1156.
Andre et al., "Malignant effusions and immunogenic tumour-derived exosomes," Lancet, 2002, 360: 295-305.
Balaj et al., "Tumour microvesicles contain retrotransposon elements and amplified oncogene sequences," Nat Commun, 2011, 2: 180.
Bast et al., "CA 125: the past and the future," Int J Biol Markers 1998, 13: 179-187.
Campuzano et al., "Magnetobiosensors based on viral protein p19 for microRNA determination in cancer cells and tissues," Chem Int Ed Engl, 2014, 53: 6168-6171.
Chen et al., "Microfluidic isolation and transcriptome analysis of serum microvesicles," Lab Chip, 2010, 10: 505-511.
Costa-Silva et al., "Pancreatic cancer exosomes initiate pre-metastatic niche formation in the liver," Nat Cell Biol, 2015, 17: 816-826.
Das and Kelley, "Tuning the bacterial detection sensitivity of nanostructured microelectrodes," Anal Chem 2013, 85: 7333-7338.
Das et al., "An electrochemical clamp assay for direct, rapid analysis of circulating nucleic acids in serum," Nat Chem, 2015, 7: 569-575.
Gercel-Taylor, "Nanoparticle analysis of circulating cell-derived vesicles in ovarian cancer patients," Anal Biochem, 2012, 428: 44-53.
Graner et al., "Proteomic and immunologic analyses of brain tumor exosomes," FASEB J, 2009, 23: 1541-1557.
Grange et al., "Microvesicles released from human renal cancer stem cells stimulate angiogenesis and formation of lung pre-metastatic niche," Cancer Res, 2011, 71: 5346-5356.
Hoshino et al., "Tumour exosome integrins determine organotropic metastasis," Nature, 2015, 527: 329-335.
Hsieh et al., "Rapid, Sensitive, and Quantitative Detection of Pathogenic DNA at the Point of Care via Microfluidic Electrochemical Quantitative Loop-Mediated Isothermal Amplification (MEQ-LAMP)," Angew Chem Int Ed Engl, 2012, 51: 4896-4900.
Im et al., "Label-free Detection and Molecular Profiling of Exosomes With a Nano-Plasmonic Sensor," Nat. Biotechnol, 2014, 32: 490-495.
International Preliminary Report on Patentability in International Application Np. PCT/US2017/015433, dated Aug. 9, 2018, 13 pages.
International Search Report and Written Opinion in International Application No. PCT/US2017/015433, dated Jun. 9, 2017, 17 pages.
Jeong et al., "Integrated Magneto-Electrochemical Sensor for Exosome Analysis," ACS nano, Feb. 2016, 10: 1802-1809.
Jorgensen et al., Extracellular Vesicle (EV) Array: microarray capturing of exosomes and other extracellular vesicles for multiplexed phenotypingJ Extracell Vesicles, 2013, 2: 20920.
Kalra et al., "Vesiclepedia: A Compendium for Extracellular Vesicles with Continuous Community Annotation," PLoS Biol, 2012, 10: e1001450.
Kobayashi et al., "Ovarian cancer cell invasiveness is associated with discordant exosomal sequestration of Let-7 miRNA and miR-200," Transl Med, 2014, 12: 4.
Kristiansen et al., "CD24 Is Expressed in Ovarian Cancer and Is a New Independent Prognostic Marker of Patient Survival," Am J Pathol, 2002, 161: 1215-1221.
Lawrie et al., "Microparticle sizing by dynamic light scattering in fresh-frozen plasma," Vox Sang, 2009, 96: 206-212.
Lee et al., "Acoustic Purification of Extracellular Microvesicles," ACS Nano 2015, 9: 2321-2327.
Li et al., "A dual-amplified electrochemical detection of mRNA based on duplex-specific nuclease and bio-bar-code conjugates," Biosens Bioelectron, 2015, 65: 245-250.
Logozzi et al., "High Levels of Exosomes Expressing CD63 and Caveolin-1 in Plasma of Melanoma Patients," PLoS One, 2009, 4: e5219.
Lotvall et al., "Minimal experimental requirements for definition of extracellular vesicles and their functions: a position statement from the International Society for Extracellular Vesicles," J Extracell Vesicles, 2014, 3: 26913.
Mandeville and Rustin, "The role of CA 125 in epithelial ovarian carcinoma," J BUON, 2002, 7: 13-17.
Meden and Kuhn, "Overexpression of the oncogene c-erbB-2 (HER2/neu) in ovarian cancer: a new prognostic factor," Eur J Obstet Gynecol Reprod Biol, 1997, 71: 173-179.
Melo et al., "Cancer Exosomes Perform Cell-Independent MicroRNA Biogenesis and Promote Tumorigenesis," Cancer Cell 2014, 26, 707-721.
Melo et al., "Glypican1 identifies cancer exosomes and facilitates early detection of cancer," Nature, 2015: 523, 177-182.
Munge et al., "Nanostructured immunosensor for attomolar detection of cancer biomarker interleukin-8 using massively labeled superparamagnetic particles," Int Ed Engl, 2011, 50: 7915-7918.
Nemiroski et al., "Universal mobile electrochemical detector designed for use in resource-limited applications," PNAS, 2014, 111: 11984-11989.

(56) References Cited

OTHER PUBLICATIONS

Paggetti et al., "Exosomes released by chronic lymphocytic leukemia cells induce the transition of stromal cells into cancer-associated fibroblasts," Blood, 2015, 126: 1106-1117.
Peinado et al., Melanoma exosomes educate bone marrow progenitor cells toward a pro-metastatic phenotype through METN, Nat Med, 2012, 18: 883-891.
Psyrri et al., "Effect of Epidermal Growth Factor Receptor Expression Level on Survival in Patientswith Epithelial Ovarian Cancer," Clin Cancer Res, 2005, 11: 8637-8643.
Raimondo, "Advances in membranous vesicle and exosome proteomics improving biological understanding and biomarker discovery," Proteomics, 2011, 11: 709-720.
Rho et al., "Magnetic Nanosensor for Detection and Profiling of Erythrocyte-Derived Microvesicles," ACS Nano 2013, 7: 11227-11233.
Rowe et al., "CheapStat: An Open-Source, "Do-It-Yourself" Potentiostat for Analytical and Educational Applications," PLoS One, 2011, 6: e23783.
Rubin et al., "Microparticles in stored red blood cells: an approach using flow cytometry and proteomic tools," Vox Sang, 2008, 95: 288-297.
Runz et al., "Malignant ascites-derived exosomes of ovarian carcinoma patients contain CD24 and EpCAM," Gynecol Oncol, 2007, 107: 563-571.
Shao et al., "Chip-based analysis of exosomal mRNA mediating drug resistance in glioblastoma," Nat Commun, 2015, 6: 6999.
Shao et al., "Protein Typing of Circulating Microvesicles Allows Real-time Monitoring of Glioblastoma Therapy," Nat. Med, 2012, 18: 1835-1840.
Skog et al., "Glioblastoma microvesicles transport RNA and protein that promote tumor growth and provide diagnostic biomarkers," Nat Cell Biol 2008, 10: 1470-1476.
Théry et al., "Exosomes: composition, biogenesis and function," Nat Rev Immunol, 2002, 2: 569-579.
Théry et al., "Membrane vesicles as conveyors of immune responses," Nat Rev Immunol, 2009, 9: 581-593.
Valadi et al., "Exosome-mediated transfer of mRNAs and microRNAs is a novel mechanism of genetic exchange between cells," Nat Cell Biol, 2007, 9: 654-659.
Van der Pol et al., "Single vs. swarm detection of microparticles and exosomes by flow cytometry," J Thromb Haemost 2012, 10: 919-930.
Verri et al., "HER2/neu Oncoprotein Overexpression in Epithelial Ovarian Cancer: Evaluation of its Prevalence and Prognostic Significance," Oncology, 2005, 68: 154-161.
Wei et al., "Electrochemical Sensor forMultiplex Biomarkers Detection," Clin Cancer Res, 2009, 15: 4446-4452.
Wei et al., "Noninvasive Saliva-based EGFR Gene Mutation Detection in Patients with Lung Cancer," Am J Respir Crit Care Med, 2014, 190: 1117-1126.
Wen et al., "DNA Nanostructure-based Interfacial engineering for PCR-free ultrasensitive electrochemical analysis of microRNA," Sci Rep, 2012, 2: 867.
Yang et al., "Detection of tumor cell-specific mRNA and protein in exosome-like microvesicles from blood and saliva," PLoS One, 2014, 9: e110641.
EP Office Action in European Appln. No. 17745010.3, dated Mar. 20, 2020, 7 pages.
Montiel et al., "Sensitive and selective magnetoimmunosensing platform for determination of the food allergen Ara h 1", Analytica chimica acta, Jun. 2015, 880:52-59.
CN Office Action in Chinese Appln. No. 201780018832.8, dated May 11, 2021, 27 pages (with English translation).

* cited by examiner

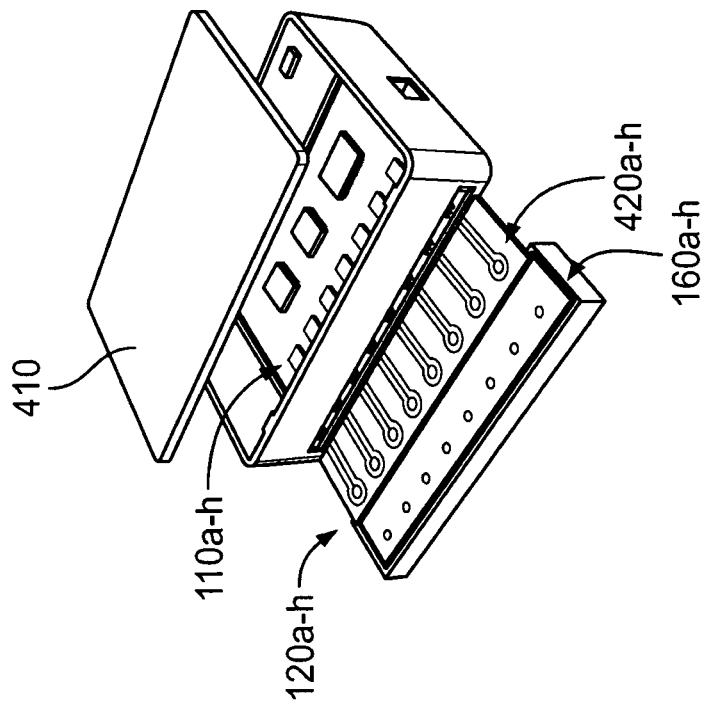
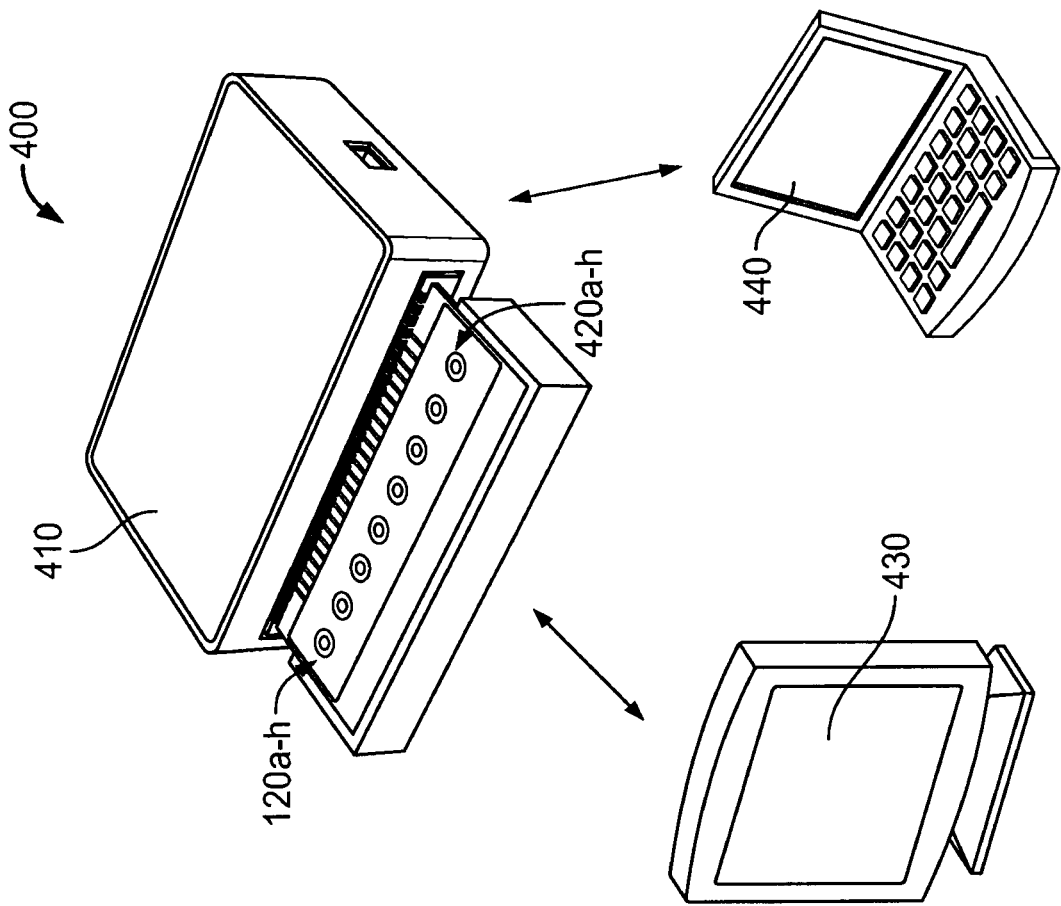
FIG. 4B
FIG. 4A

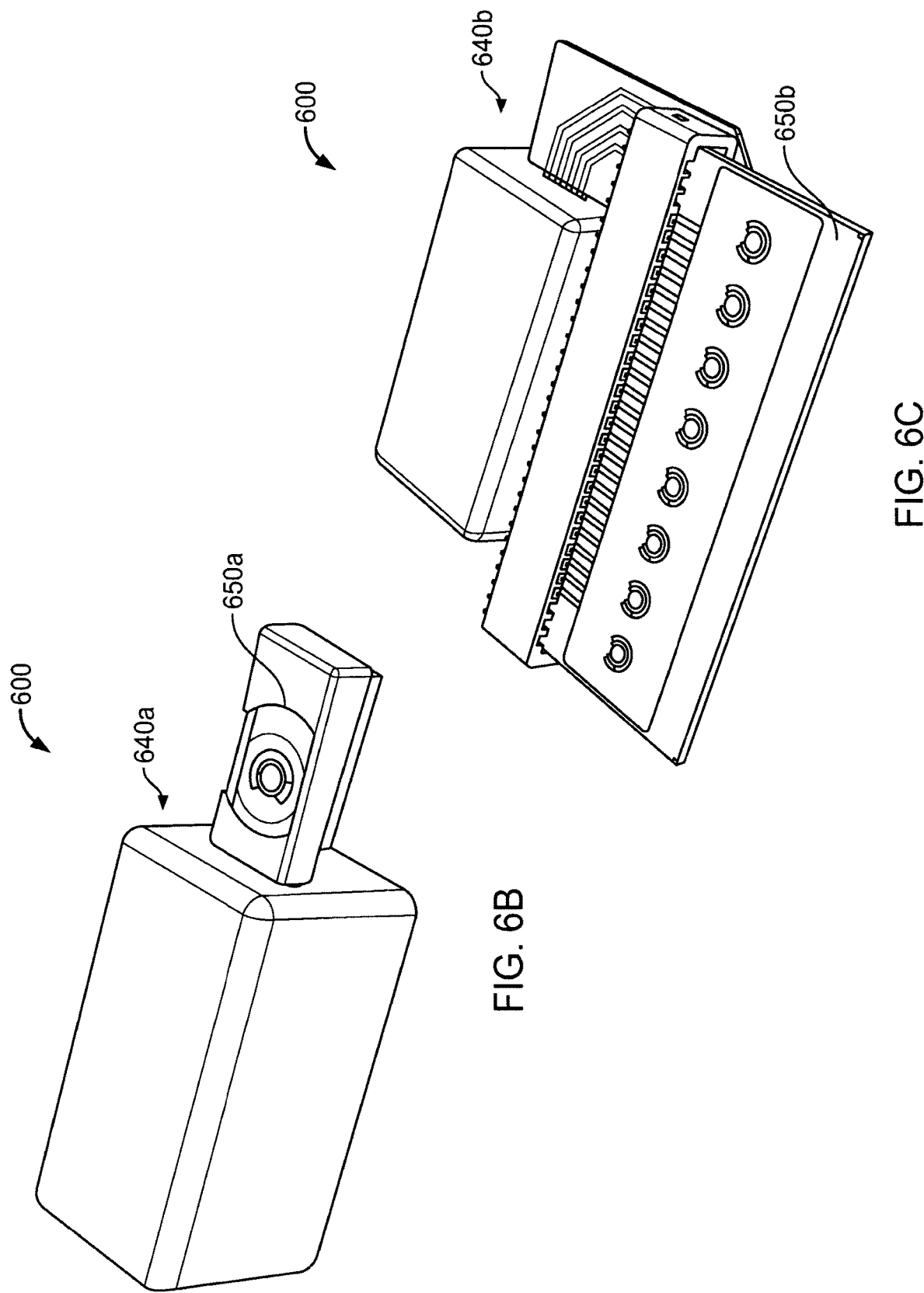

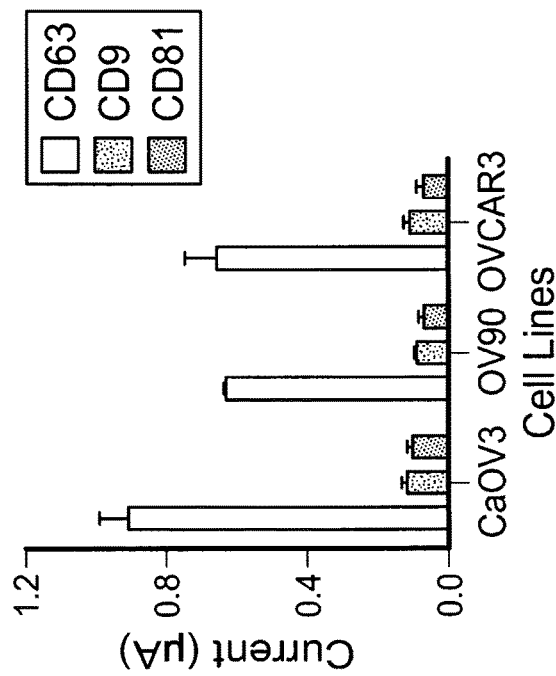
FIG. 20
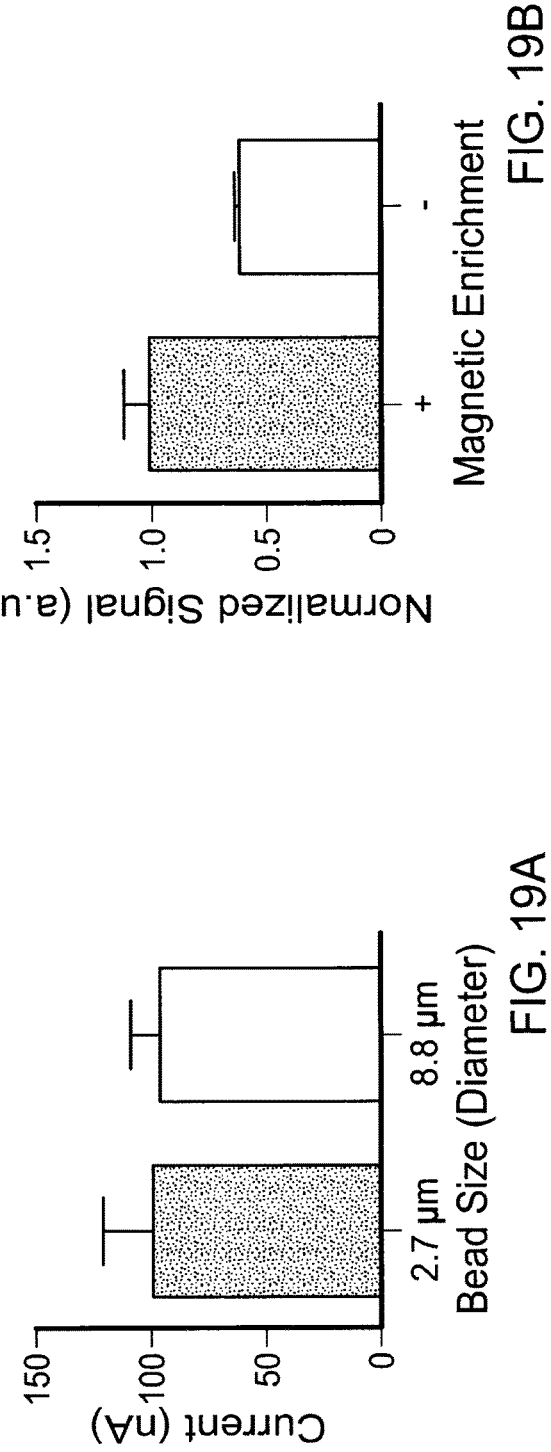
FIG. 19B
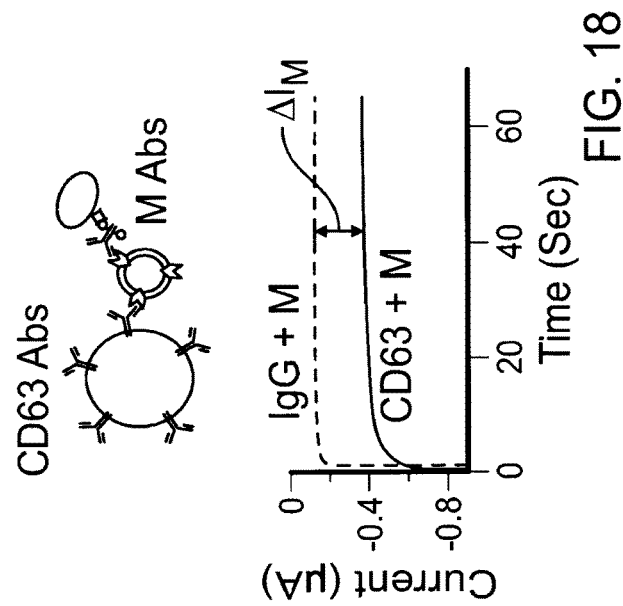
FIG. 18
FIG. 19A

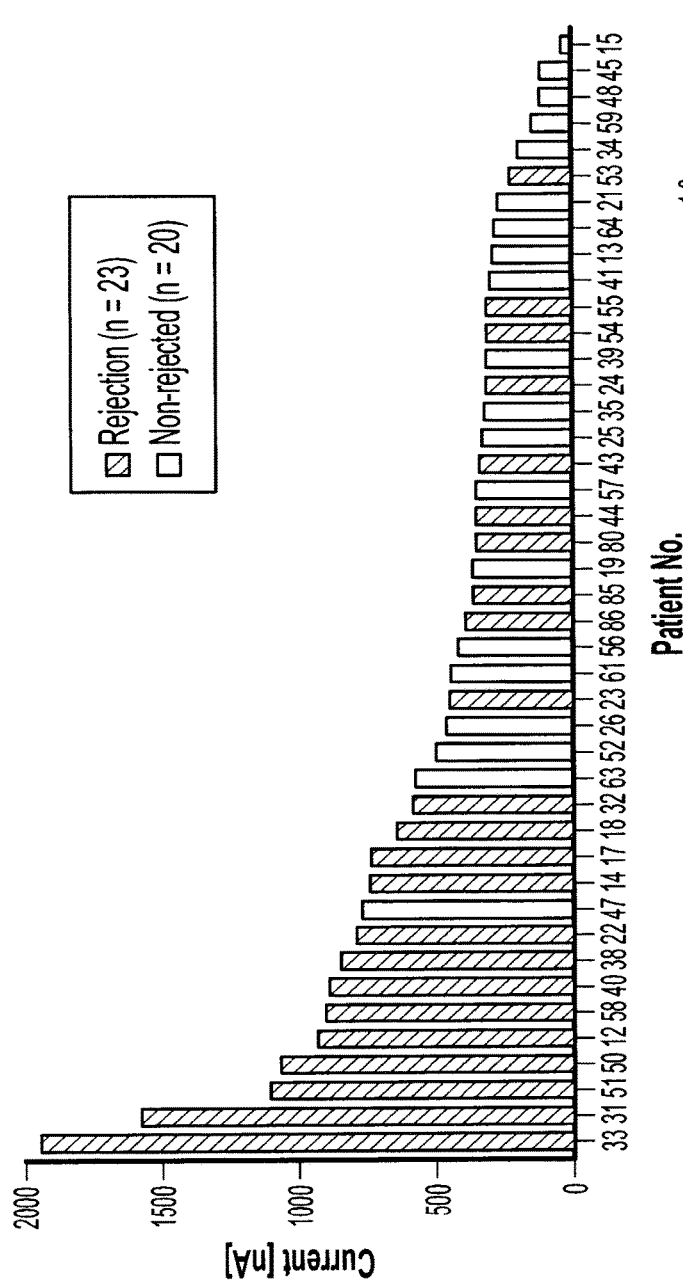
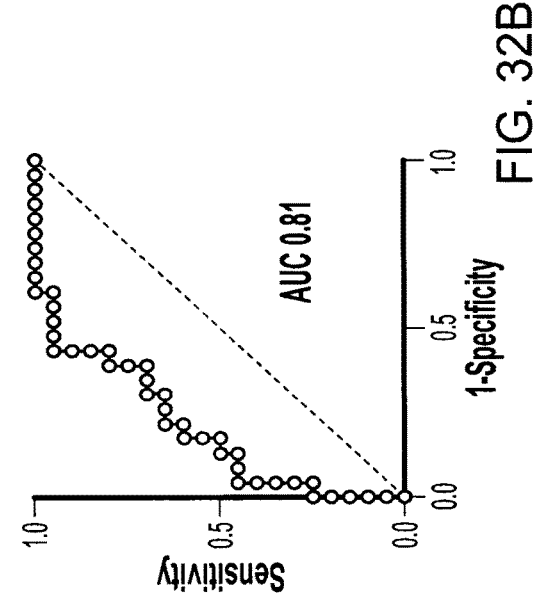
FIG. 32A
FIG. 32B

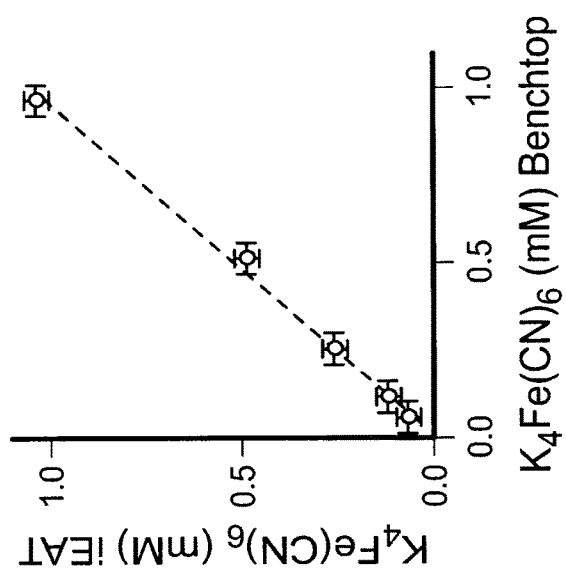
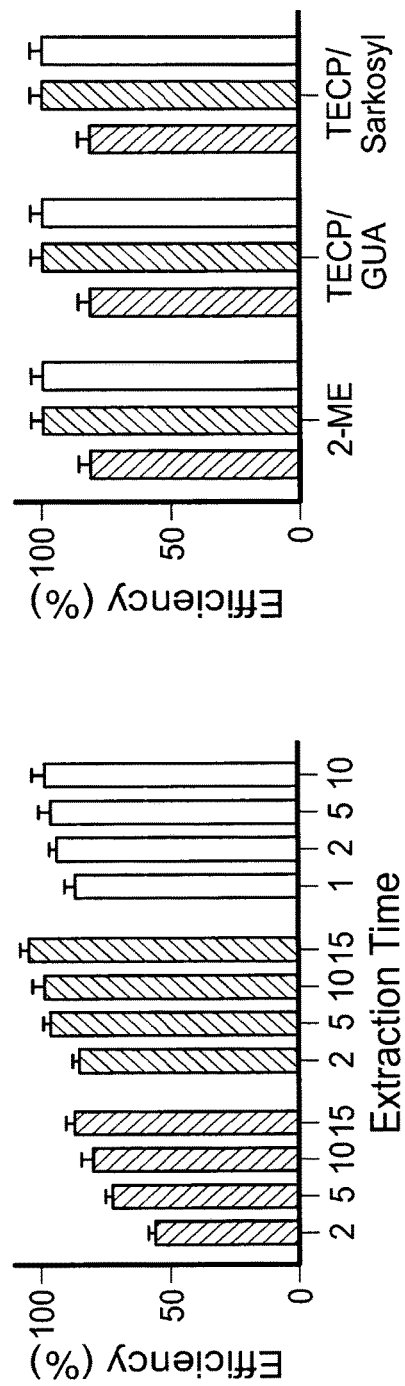
FIG. 35
FIG. 36A
FIG. 36B

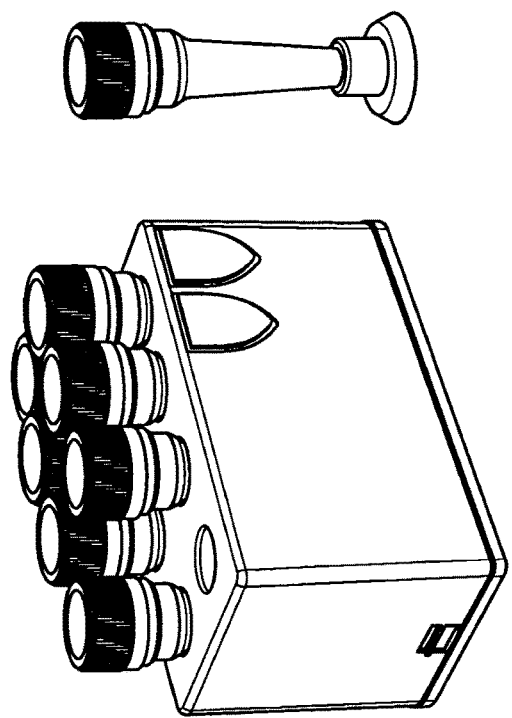
FIG. 37
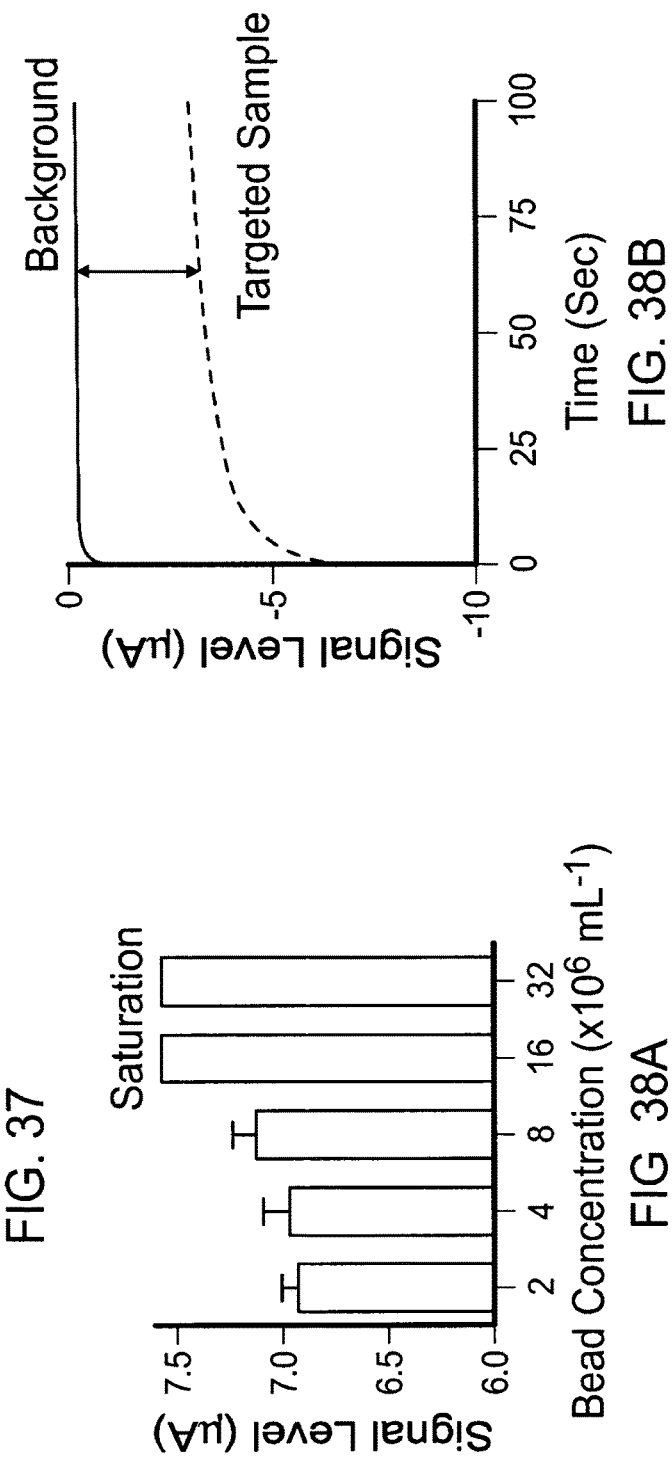
FIG. 38B
FIG. 38A

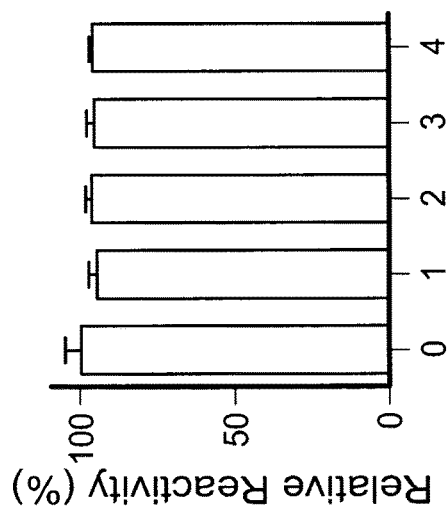
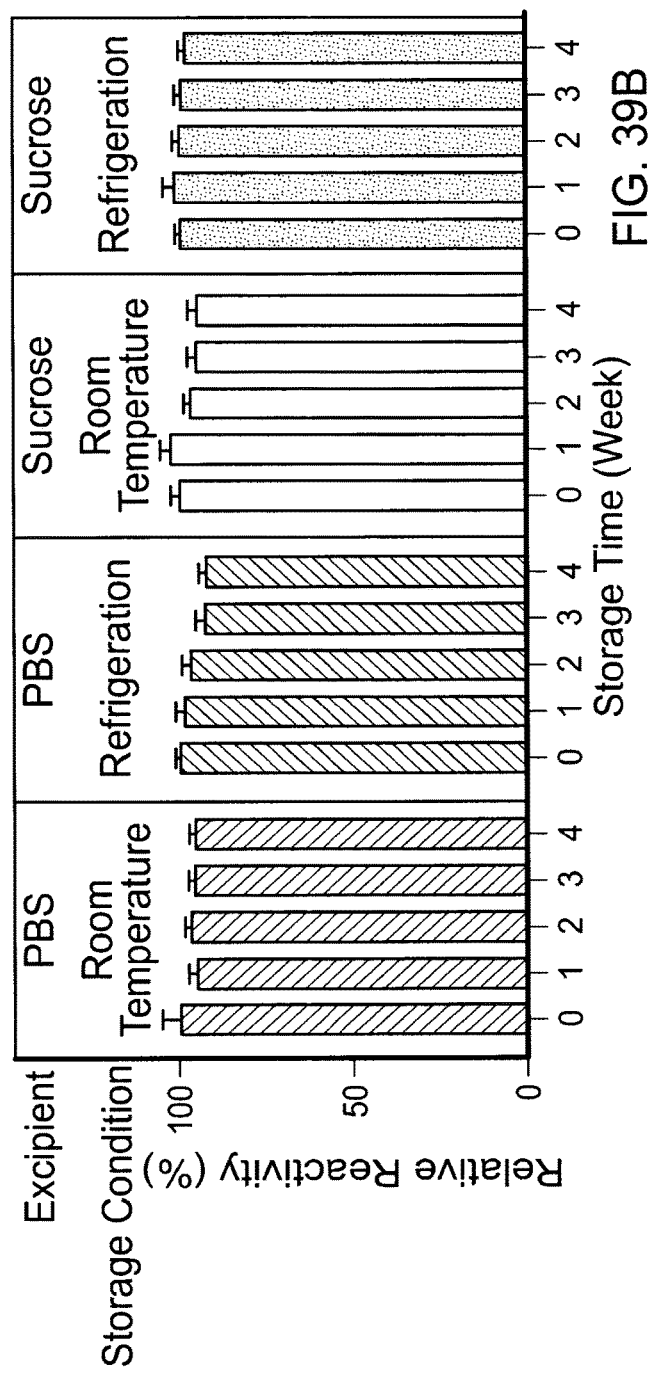

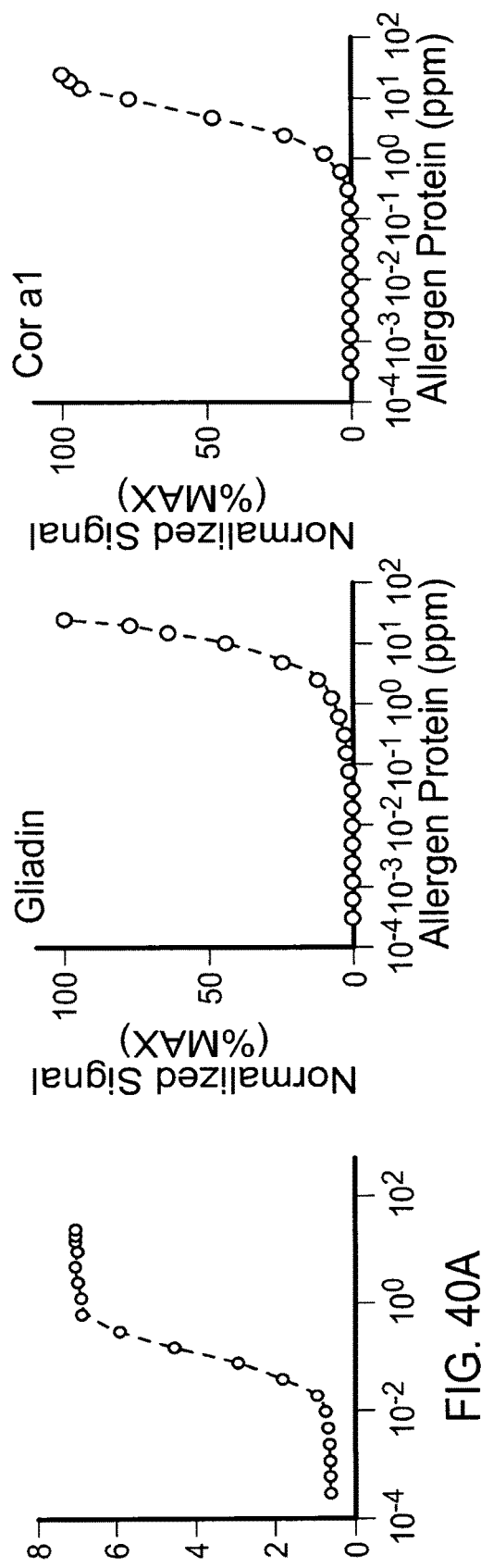
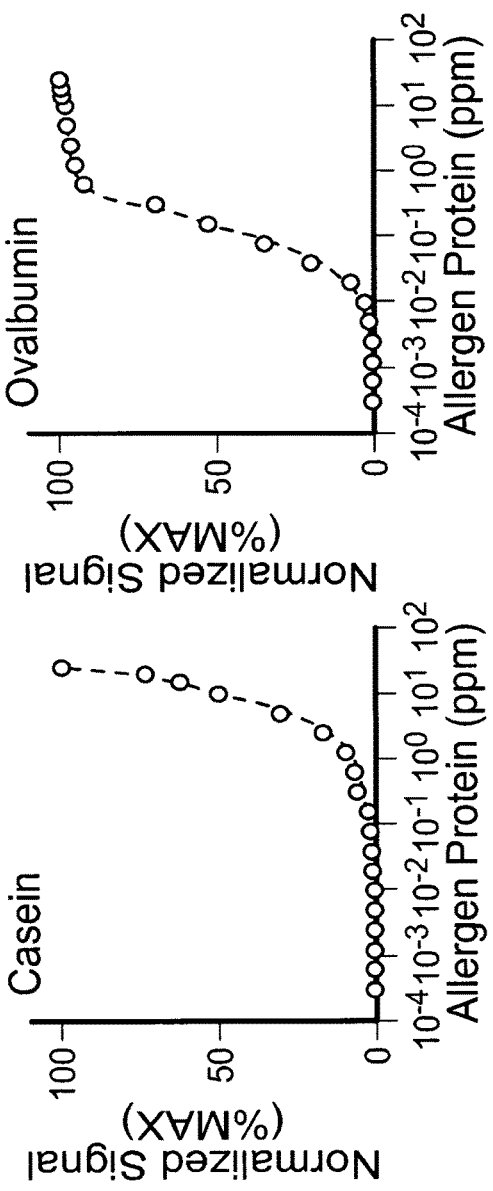
FIG. 40A
FIG. 40B

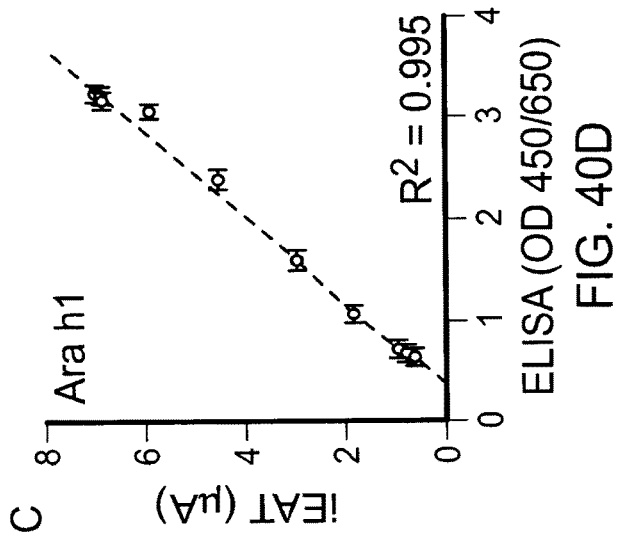
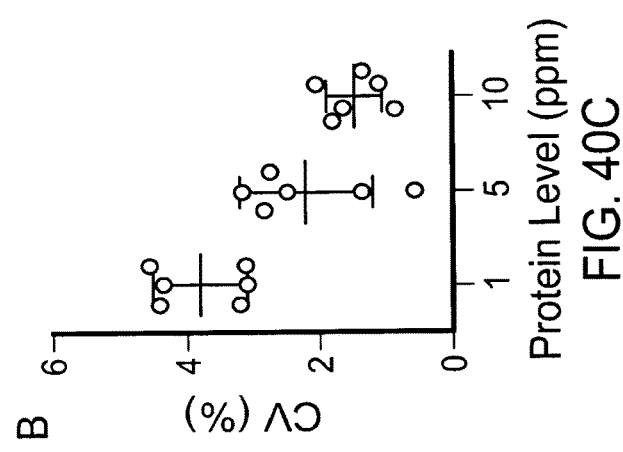
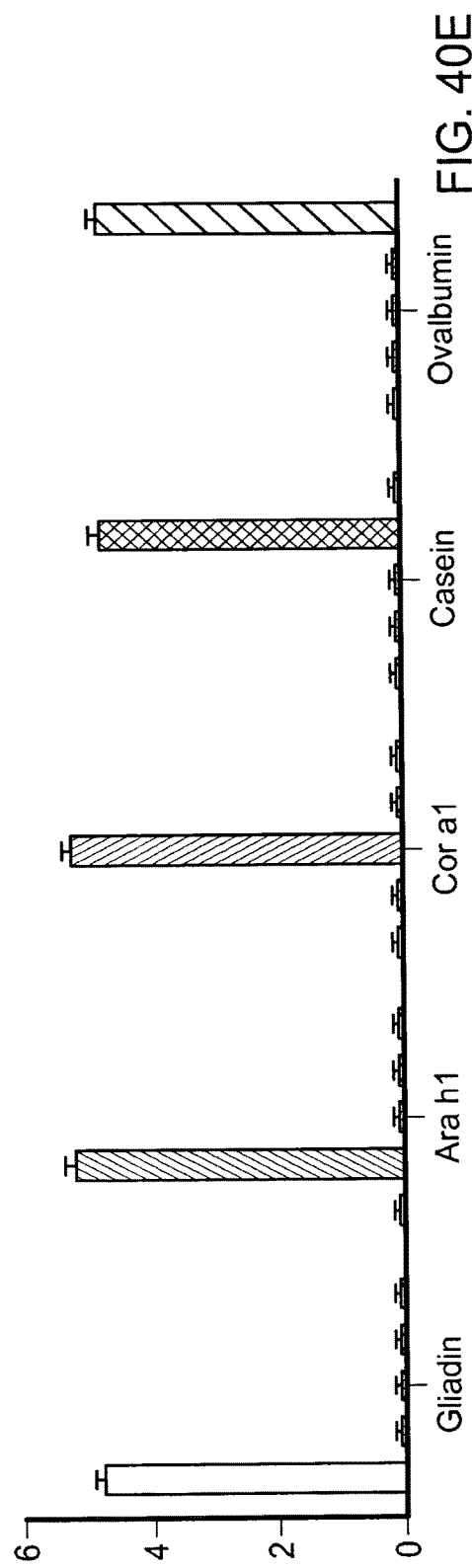
FIG. 40C
FIG. 40D
FIG. 40E

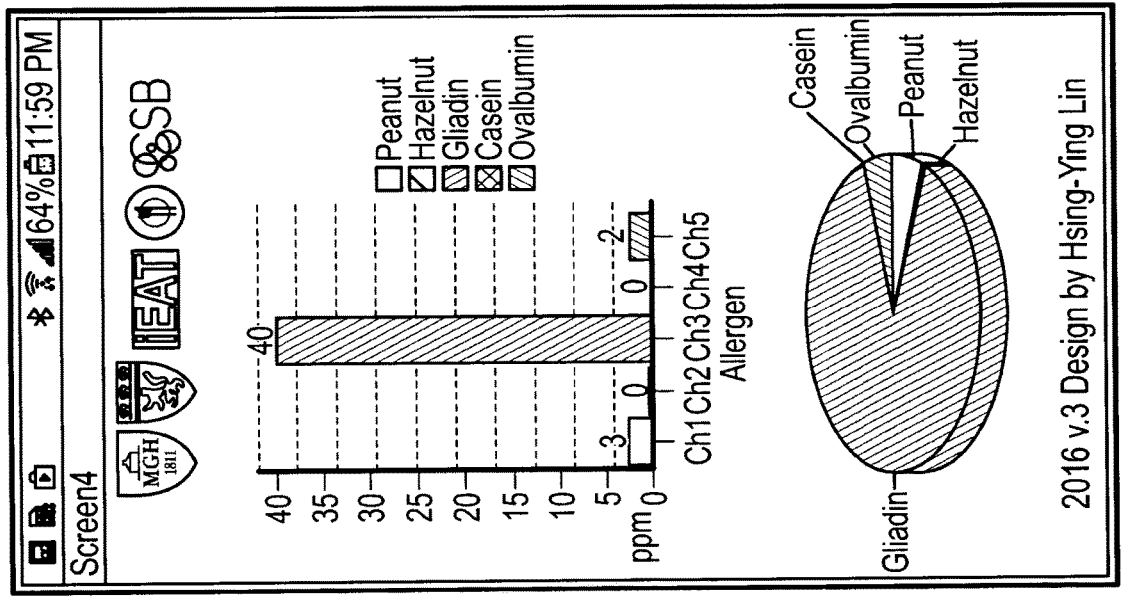
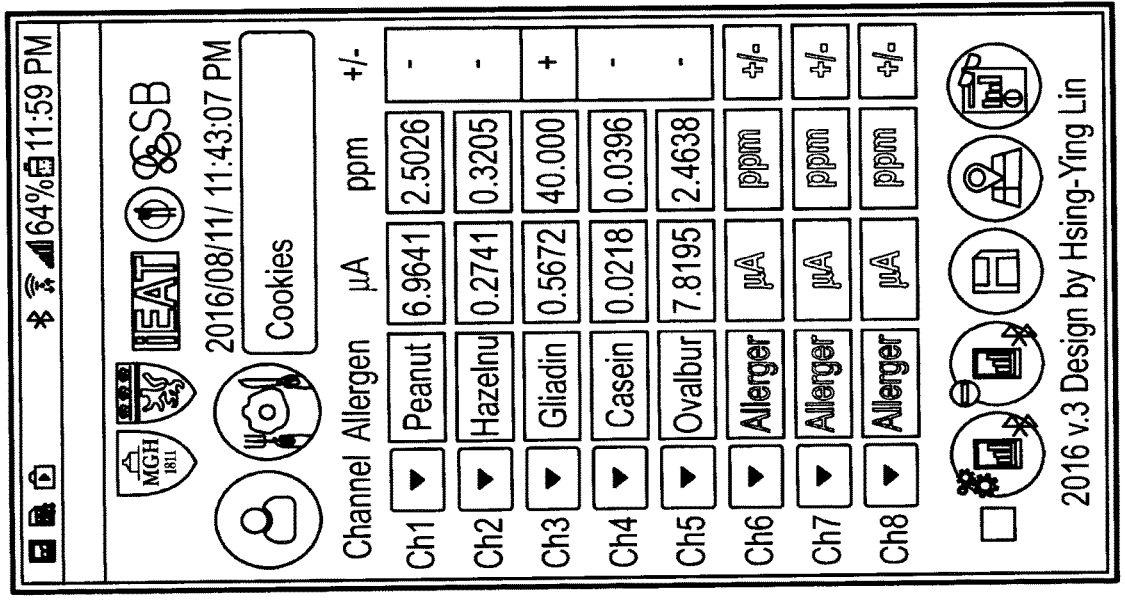
FIG. 41C

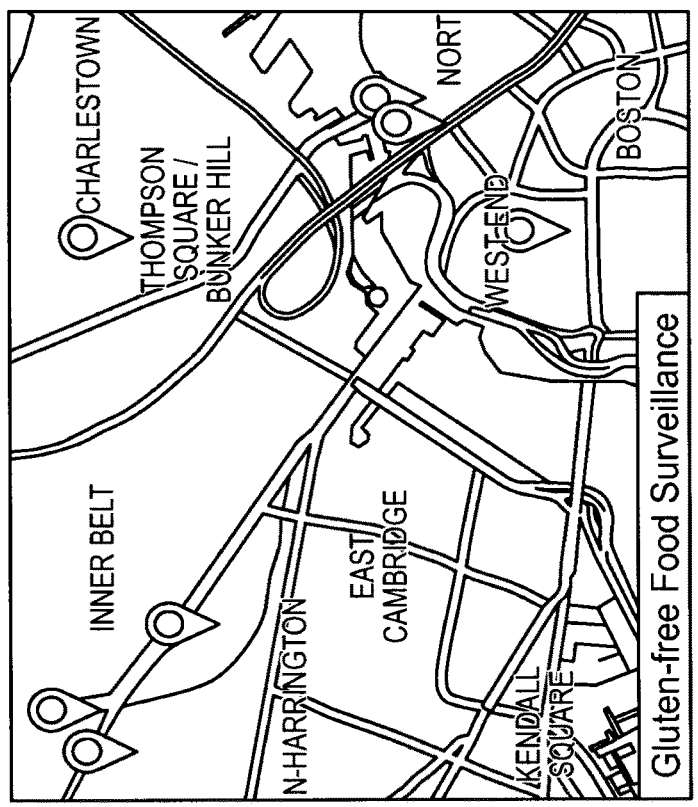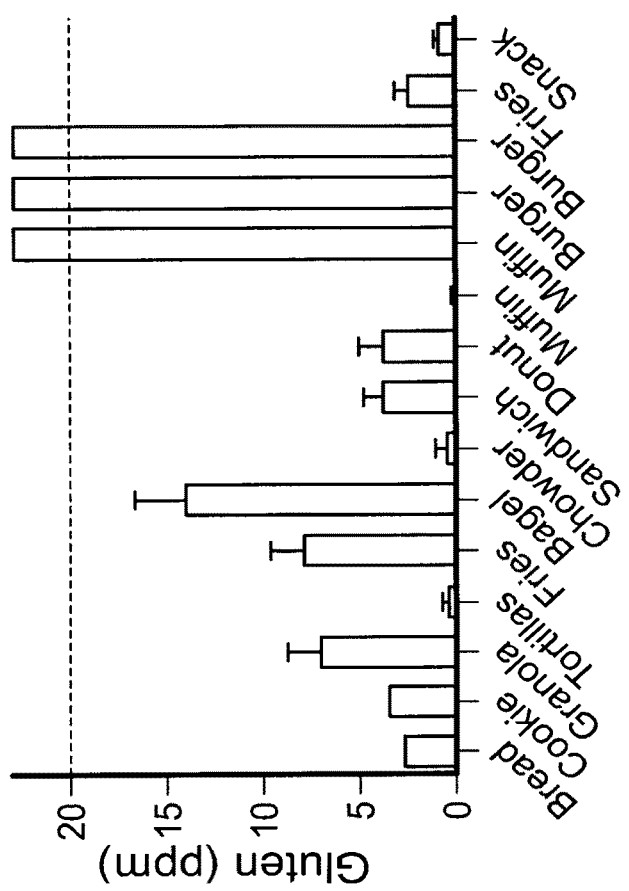
FIG. 41D

MAGNETIC ELECTROCHEMICAL SENSING

CROSS-REFERENCE TO RELATED APPLICATIONS

This application is a 371 U.S. National Phase Application of PCT/US2017/015433, filed on Jan. 27, 2017, which claims priority from U.S. Provisional Application Ser. No. 62/287,719, filed on Jan. 27, 2016, from U.S. Provisional Application Ser. No. 62/288,254, filed on Jan. 28, 2016, and from U.S. Provisional Application Ser. No. 62/339,519, filed on May 20, 2016, all of which are incorporated herein by reference in their entirety.

TECHNICAL FIELD

This disclosure relates to systems and techniques for examining analytes using magnetic electrochemical sensing.

BACKGROUND

Biological samples are often examined for the presence and prevalence of particular analytes, such as peptides, proteins, lipids metabolites, and other small molecules. In some cases, the presence and prevalence of specific analytes can provide insight into a particular biological or pathogenic process, a progression of a particular disease, or some other biological condition of a subject. In some cases, the presence and prevalence of specific analytes can provide insight into the composition of a particular substance or material.

SUMMARY

In one aspect, the present disclosure provides target analyte detection devices that include a housing containing a potentiostat and a microcontroller coupled to the potentiostat. The devices also include a substrate having a plurality of electrodes on a first surface of the substrate. A first set of electrodes of the plurality of electrodes defines a first sample detection region. The substrate can be removably attachable to the housing such that the first set of electrodes is coupled to the potentiostat upon attaching the substrate to the housing. The devices also include a magnet assembly couplable to a second surface of the substrate. The magnet assembly includes a magnet positioned in the magnet assembly such that a magnetic field from the magnet extends through the substrate and the first set of electrodes into an area above the first sample detection region upon coupling the magnet assembly to the substrate.

Implementations of this aspect can include one or more of the following features. In some implementations, the housing can contain a digital-to-analog converter (DAC) circuit. An output of the DAC can be electrically coupled to an input of the potentiostat. The housing can also contain an analog-to-digital converter (ADC) circuit. An input of the contain circuit can be coupled to an output of the potentiostat. The housing can also contain a microcontroller electrically coupled to the DAC circuit and to the ADC circuit. The microcontroller can be configured to provide a voltage signal to an input of the DAC circuit. The microcontroller can be configured to receive a measurement signal from an output of the ADC circuit.

In some implementations, the devices can include a plurality of potentiostats. The plurality of electrodes can include at least one additional set of electrodes. Each set of electrodes can be couplable to a different respective potentiostat of the plurality of potentiostats, and each set of electrodes can define a different corresponding sample detection region.

In other implementations, the devices can include a multiplexer electrically coupled to an output of each potentiostat of the plurality of potentiostats. The multiplexer can be configured to electrically couple a selected output to the input of the ADC circuit.

In certain implementations, the devices can include a well-plate arranged on a surface of the substrate, the well-plate having a plurality of wells. Each well of the plurality of wells can be arranged directly over a different corresponding sample detection region.

In some implementations, the magnet assembly can include a plurality of magnets. Each magnet of the plurality of magnets can be positioned adjacent to the substrate and aligned with a corresponding set of electrodes upon coupling the magnet assembly to the substrate such that a magnetic field extends from the magnet through the substrate and the corresponding set of electrodes into an area above a sample detection region defined by the corresponding set of electrodes.

In additional implementations, the substrate can include a card-edge connector and the housing can include a card-edge connector receptacle. In some implementations, the device can further include an electronic communication interface. In other implementations, the electronic communication interface can include at least one universal serial bus connector or a wireless transceiver. In certain implementations, the first set of electrodes can include three separate electrodes. In other implementations, a first electrode and second electrode of the three separate electrodes can be a first metal, and a third electrode of the three separate electrodes can be a second metal. In certain implementations, the first set of electrodes can consist of two separate electrodes. In some implementations, the first set of electrodes can include interdigitated electrodes.

In some implementations, the housing can further contain a power supply and a transceiver coupled to the microcontroller. In certain implementations, the device can further include a display coupled to the microcontroller.

In general, in another aspect, the present disclosure provides methods of detecting a presence of target analyte. The new methods include providing a plurality of magnetic beads to a first fluid sample. The plurality of magnetic beads includes first binding moieties that specifically bind to the target analyte. The methods also include allowing the plurality of magnetic beads to bind to the target analyte within the first fluid sample, and transferring the magnetic beads from the first fluid sample to a second fluid sample. The second fluid sample includes second binding moieties that are specific for binding to the target analyte. The second binding moieties can be bound to a reactive enzyme or other reporter groups. Transferring the magnetic beads can include immersing a sheath within the first fluid sample, placing a magnet within the sheath that is immersed within the first fluid sample, such that the magnetic beads adhere to the sheath, removing the sheath containing the magnet from the first fluid sample, and immersing the sheath containing the magnet in the second fluid sample.

The methods also include allowing the second binding moieties within the second fluid sample to bind to the target analyte bound to the first binding moieties of the magnetic bead, combining the second fluid sample including the plurality of magnetic beads and the second binding moieties with an electron mediator solution to obtain a third fluid sample, and providing the third fluid sample to a sample detection region of a substrate. The sample detection region can be or is arranged on a first electrode. The methods also include exposing the third fluid sample to a magnetic field to retain the plurality of magnetic beads within the third fluid sample next to the first electrode. The first electrode is electrically coupled to a potentiostat. The methods also include inducing an oxidation-reduction reaction between electron mediators within the third fluid sample and the reactive enzyme, and monitoring an output of the potentiostat to determine a presence of the target analyte in the third fluid sample. The output of the potentiostat is modified by the oxidation-reduction reaction.

Implementations of this aspect can include one or more of the following features. In some implementations, inducing the oxidation-reduction reaction can include applying an electrical potential to a second electrode such that the oxidation-reduction reaction occurs, wherein the second electrode is electrically coupled to the potentiostat.

In other implementations, monitoring the output of the potentiostat can include measuring a voltage or current from the first electrode. The voltage or current from the first electrode can vary as a result of the oxidation-reduction reaction. In some implementations, monitoring the output of the potentiostat can include selecting the output of the potentiostat, from a plurality of different potentiostats' outputs, providing the selected output to a microcontroller unit, and presenting the selected output on a display. In certain implementations, the reactive enzyme can include horseradish peroxidase (HRP) and the electron mediator solution comprises 3,3',5,5'-tetramethylbenzidine (TMB).

In some implementations, the target analyte can include extracellular vesicles. In some implementations, the extracellular vesicles can include exosomes. In some implementations, the target analyte can include any one of CD24, EpCAM, CA125, EGFR, HER2, MUC1, CD44, CD44v6, CEA, Mesothelin, Trop2, GPC1, WNT2, Grp94, SSTR2, EGFRv3, IDH1-R132, GPA33, KRAS, CD166, CD133, MET, B7H3, CD63, CD9, and CD81 biomarkers.

In some implementations, the methods can further include comparing the output of the potentiostat to a reference level to determine whether the output is above or below the reference level, and diagnosing the presence or absence of a cancer within a patient based on the comparison.

In certain implementations, the target analyte can include immune cell markers such as CD2, CD3, CD45, CD52, HLA-ABC, CD81, CXCL10, or CXCL9 biomarkers.

In some implementations, the methods can further include comparing the output of the potentiostat to a reference level to determine whether the output is above or below the reference level, and diagnosing whether or not a patient has rejected an organ transplant based on the comparison.

In some implementations, the first fluid sample can include blood or urine. In various implementations, the target analyte can include a protein, a cell, a peptide, a protein, a lipid, a toxin, nucleic acides, microbes, food antigens, or a metabolite.

In some implementations, the methods can further include combining a food sample with an extraction buffer to provide the first fluid sample, and incubating the food sample with the extraction buffer to extract the target analyte from the food sample.

In general, in another aspect, the present disclosure provides kits that include a sample tube, a sample tube cap, an elongated bar including a first magnet, and a target analyte detection device, e.g., as described herein. The target analyte detection device includes a housing, a potentiostat in the housing, and a first substrate include a plurality of electrodes. The plurality of electrodes includes a first set of electrodes defining a first sample detection region. The first substrate is configured to be removably attached to the housing such that the first set of electrodes couples to the potentiostat when the first substrate is attached to the housing. The target analyte detection device also includes a second magnet configured to be positioned adjacent to the first substrate such that a magnetic field from the magnet extends through the substrate and the first set of electrodes into an area above the first sample detection region.

Implementations of this aspect can include one or more of the following features. In some implementations, the sample tube cap can include an opening extending into an elongated sheath. The elongated bar can be sized to fit within the elongated sheath.

In some implementations, the kits can include an extraction buffer solution having a plurality of magnetic beads, a washing buffer solution, a target analyte buffer solution, and an oxidizing enzyme buffer solution.

In some implementations, the target analyte detection device can include a digital-to-analog converter (DAC) circuit. An output of the DAC can be electrically coupled to an input of the potentiostat. The target analyte detection device can also include an analog-to-digital converter (ADC) circuit. An input of the ADC circuit can be coupled to an output of the potentiostat. The target analyte detection device can also include a microcontroller electrically coupled to the DAC circuit and to the ADC circuit. The microcontroller can be configured to provide a voltage signal to an input of the DAC circuit. The microcontroller can be configured to receive a measurement signal from an output of the ADC circuit. In some implementations, the target analyte detection device can include a display.

In some implementations, the kits can further include a second substrate having an additional plurality of electrodes defining a second sample detection region. The second substrate can be configured to be removably attached to the housing. In other implementations, the kits can include a third magnet. The third magnet can be configured to be removably attached to the second substrate.

One or more of the implementations described can provide various benefits. For example, implementations of a magnetic electrochemical sensing system can be used to non-invasively examine biological samples for the presence and prevalence of particular analytes, such as peptides, proteins, lipids metabolites, and other small molecules. In some cases, this information can provide insight into a particular biological or pathogenic process, a particular progression of a particular disease, or some other biological condition. In some cases, this information can provide insight into the composition of a particular substance.

In some cases, samples can be analyzed without the need to conduct extensive processing techniques (e.g., filtration or centrifugation), which may require specialized equipment. Thus, users can analyze samples more easily and/or in a more cost effective manner. In some cases, users can examine each sample quickly, such that many samples can be efficiently examined for the presence of one analyte or multiple different analytes. In some cases, lay users can conduct an examination themselves without the assistance of an experienced technician, and without the need for expensive equipment.

Further, in some cases, cell-specific extracellular vesicles (e.g., exosomes, microvesicles, membrane particles, and apoptotic blebs or vesicles) can be isolated directly from complex media without need for extensive filtration or centrifugation. Further, the assay can achieve high detection sensitivity through magnetic enrichment and enzymatic amplification. Further still, through the electrical detection scheme, sensors can be miniaturized and expanded for parallel measurements.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

"Target analyte" refers to a single target analyte of a particular type or a plurality of target analytes of the same type unless otherwise stated.

"Specific binding" refers to the forming of a bond between a binding moiety and an analyte of a particular type unless otherwise stated.

The details of one or more embodiments are set forth in the accompanying drawings and the description below. Other features and advantages will be apparent from the description and drawings, and from the claims.

BRIEF DESCRIPTION OF THE DRAWINGS

FIGS. 4A and 4B are diagrams of another example of an instrument for examining analytes.

FIG. 6A-6C are diagrams of another example of an instrument for examining analytes.

FIG. 18 is a schematic diagram of the electrochemical measurement in the iMEX assay.

FIG. 19A shows the effect of magnetic bead size on the measured current.

FIG. 19B shows the effect of magnetic enrichment on the measured signal.

FIG. 20 shows a signal comparison of three tetraspanin markers (CD63, CD9, and CD81) in cancer extracellular vesicles.

FIG. 32A shows the measured current when EVs with CD3 expression were detected with iMEX assay in a validation set.

FIG. 32B shows a ROC curve used to determine the sensitivity, specificity and accuracy of CD3 marker in the validation set.

FIG. 35 shows a comparison benchmark between the iEAT performance against commercial equipment (SP-200, Bio-Logic).

FIG. 36A shows an example of an Ara h1 extraction with 2-ME buffer.

FIGS. 36B and 36C show the performance of three extraction buffers for five tested antigens.

FIG. 37 shows an example of a heating device.

FIG. 38A shows current measurements for a peanut allergen titration.

FIG. 38B shows dynamic current responses after a reduction potential was applied to a sample.

FIGS. 39A and 39B show the activity of lyophilized reagents after storage.

FIGS. 40A and 40B show generated response curves for various allergens.

FIG. 40C shows intra-assay variations, estimated by measuring three different concentrations of standard.

FIG. 40D shows a comparison between iEAT results and ELISA measurements.

FIG. 40E shows a comparison of signal responses between various target and non-target samples.

FIG. 41C shows example graphical user interfaces of a smartphone application for interacting with the iEAT system.

FIG. 41D shows profiling results obtained using the iEAT system (left), and an example graphical user interface of a smartphone application for interacting with the iEAT system.

DETAILED DESCRIPTION

Systems and techniques for examining analytes using magnetic electrochemical sensing are described herein. One or more of the implementations described herein can be used to identify analytes such as cells, extracellular vesicles (EVs) such as microvesicles, membrane particles, apoptotic blebs or vesicles or exosomes (e.g., transmembrane and cytosolic proteins, mRNA, DNA, and microRNA), peptides, proteins, lipids, metabolites, and other molecules, either free-floating (e.g., in a serum or a solution) or expressed on the surface of a biological structure (e.g., on the surface of an extracellular vesicle or a cell).

In an example of an implementation, a sample is collected from a subject (e.g., a sample of biological fluid, such as blood or urine). The sample is processed using magnetic separation, such that particular analytes of interest (e.g., analytes indicative of a particular biological or pathogenic process, a particular progression of a particular disease, or some other biological condition) are isolated and/or concentrated near a sample probe of a measurement instrument. The presence and/or prevalence of these analytes in the sample are subsequently investigated using the measurement instrument via electrochemical detection. The resulting information can be used to provide more effective care to the subject (e.g., by enabling caretakers to make diagnoses and/or administer treatment in a more informed manner).

In another example of an implementation, a sample is collected from a substance. The sample is processed using magnetic separation, such that particular analytes of interest (e.g., analytes indicative of a particular material or antigen) are isolated and/or concentrated near a sample probe of a measurement instrument. The presence and/or prevalence of these analytes in the sample are subsequently investigated using the measurement instrument via electrochemical detection. The resulting information can be used to provide insight into the composition of the substance. As an example, samples of a food product can be analyzed for the presence of particular allergens, such that a consumer can make more informed choices regarding his diet.

In some cases, samples can be analyzed without the need to conduct extensive processing techniques (e.g., filtration or centrifugation), which may require specialized equipment. Thus, users can analyze samples more easily and/or in a more cost effective manner. In some cases, users can examine each sample quickly, such that many samples can be efficiently examined for the presence of one analyte or multiple different analytes. In some cases, lay users can conduct an examination themselves without the assistance of an experienced technician, and without the need for expensive equipment.

Figure 1:
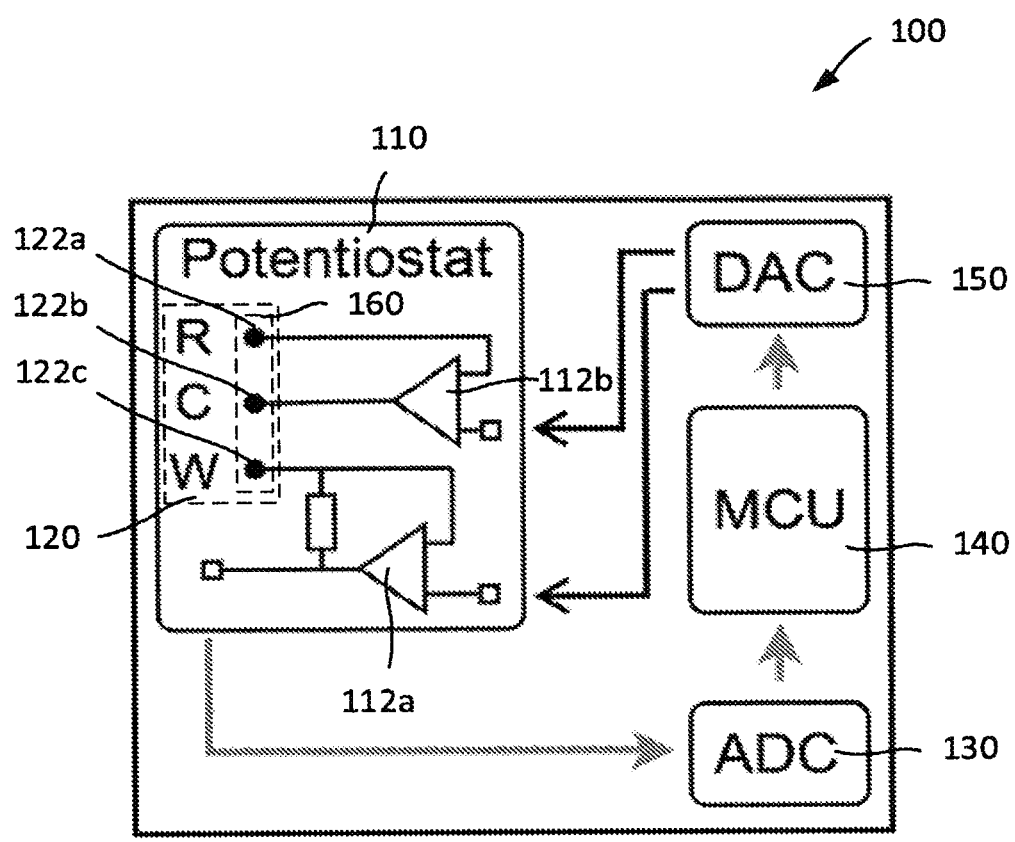
FIG. 1 is a schematic diagram of an example of a magnetic electrochemical sensing system for examining analytes.

An example of a system 100 for examining analytes is schematically shown in FIG. 1. The system 100 includes a potentiostat 110 electrically coupled to a probe 120. The system 100 also includes an analog-to-digital converter (ADC) 130, a microcontroller unit (MCU) 140, a digital-to-analog converter (DAC) 150, and a magnet assembly 160.

The probe 120 includes three electrodes: a "reference" electrode 122a, a "counter" electrode 122b, and a "working" electrode 122c. During operation of the system 100, each of these electrodes 122a-c are placed into contact with a fluid sample to be analyzed. The magnet assembly 160 (e.g., placed adjacent to the probe 120) attracts magnetically labeled particles in the fluid sample to the electrodes 122a-c (e.g., by inducing a magnetic field that extends through the electrodes). In some cases, the surfaces or one or more of the electrodes 122a-c can be collectively referred to as a sample detection region.

The potentiostat 110 is electrically coupled to each of the electrodes 122a-c, and is configured, during operation, to maintain a pre-defined potential difference between the working electrode 122c and the reference electrode 122a. Further, the potentiostat 110 is configured to measure a current induced from the working electrode 122c across the counter electrode 122b.

As shown in FIG. 1, the potentiostat 110 includes two operational amplifiers 112a and 112b. The first operational amplifier 112a is electrically coupled to the working electrode 122c, and is configured to maintain the pre-defined potential difference between the working electrode 122c and the reference electrode 122a (e.g., by applying a potential to the working electrode 122c as a bias relative to the potential of the reference electrode 122a). In some cases, the potential can be between approximately −1.65 V and approximately 1.65 V. In some cases, the potential can be approximately −0.1 V. The second operational amplifier 112b is electrically coupled to the reference electrode 122a and the counter electrode 122b, and is configured as a trans-impedance amplifier to convert a current induced from the working electrode 122c across counter electrode 122b to a voltage signal.

The electrodes 122a-c can be made of various materials. In some cases, the working electrode 122c and the counter electrode 122b can be made, either partially or entirely, of a first material (e.g., gold), and the reference electrode 122a can be made, either partially or entirely, of a second material (e.g., silver or silver chloride). In some cases, different materials can be used for some or all of the electrodes 122a-c. In some cases, different materials may increase the signal level by increasing the effective surface area of electrodes.

The potentiostat 110 is electrically coupled to the ADC 130, such that the voltage signal (indicative of the current from the working electrode 122c across counter electrode 122b) is transmitted to the ADC 130. The ADC 130 digitizes the voltage signal (e.g., into a digital signal representing the voltage signal), and transmits the digitized voltage signal to the MCU 140 for processing.

The MCU 140 processes the digitalized voltage signal. In some cases, the MCU 140 can determine particular characteristics of a sample based on the digitalized voltage signals. For example, based on the digitized voltage signal, the MCU 140 can determine whether a particular analyte is present in the sample. As another example, based on the digitized voltage signal, the MCU can determine the absolute concentration and/or relative concentration of the analyte in the sample.

The MCU 140 is also configured to control the operation of the potentiostat 110 via a DAC 150. For example, the MCU 140 can transmit digital control signals to the DAC 150, and the DAC 150 can convert the digital control signals into corresponding analog signals. These analog signals can be used to control the operation of the potentiostat 110. As an example, the MCU 140, via the DAC 150, can increase and/or decrease the potential of the working electrode 122c relative to the reference electrode 122a, and control the sampling of current from the working electrode 122c across counter electrode 122b by applying analog signals to the inputs of the operational amplifiers 112a and 112b.

Although a three electrode implementation is described with respect to FIG. 1, it is understood that other configurations can be used to measure an induced current within a sample. For example, configures such as dual-working electrode configurations (e.g., a interdigitated electrode array (IDA)) or two-electrode configurations (e.g., excluding a counter electrode) can be used.

Figure 2:
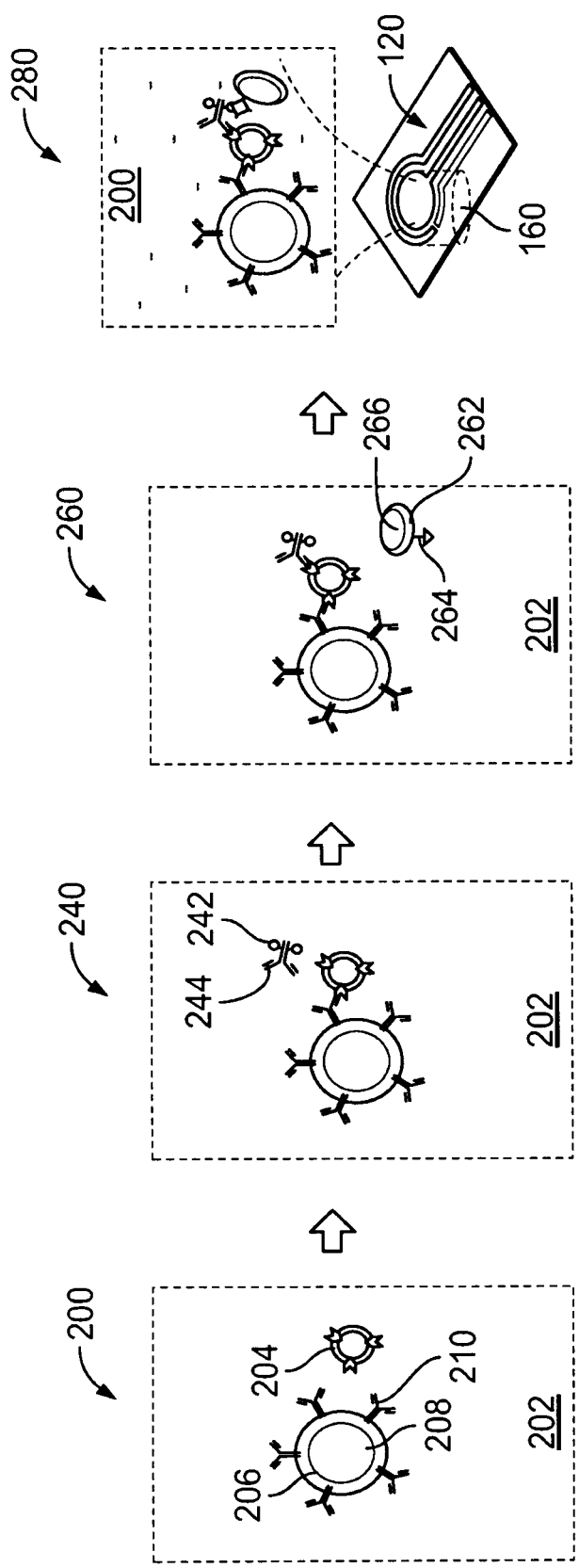
FIG. 2 is a diagram of an example of the usage of a magnetic electrochemical sensing system.

An example usage of the system 100 is shown in FIG. 2. In this example, the system 100 is used to analyze a fluid sample 202 for the presence of an analyte 204.

As shown in panel 200, the fluid sample 202 (containing the analyte 204) is mixed with a solution containing magnetic beads 206. Each magnetic bead 206 includes a magnetic core 208, and one or more binding moieties 210 specific to the analyte 204 coated onto the surface of the magnetic core 208.

Upon mixing, the analyte 204 is captured by the magnetic bead 206 due to the interaction between the binding moiety 210 and the analyte 204. The sample 202 can be washed to remove unbound analytes 204 (e.g., by magnetically collecting the magnetic beads 206, and transferring the collected magnetic beads 206 to a fresh sample buffer).

As shown in panel 240, the sample 202 is mixed with a solution containing secondary molecules 242. Each secondary molecule 242 includes a binding moiety 244 specific to the analyte 204. Upon mixing, the secondary molecule 242 is also captured by the magnetic bead 206 due to the interaction between the binding moiety 244 and the analyte 204. The sample 202 can be washed to remove unbound secondary molecules 242.

As shown in panel 260, the sample 202 is mixed with a solution containing tertiary molecules 262. Each tertiary molecule 262 includes a binding moiety 264 specific to the secondary molecule 242, and reactive enzyme 266. Example reactive enzymes 266 include an oxidizing enzyme, such as horseradish peroxidase (HRP), alkaline phosphatase, or beta-galactosidase). Upon mixing, the tertiary molecule 262 is also captured by the magnetic bead 206 due to the interaction between the binding moiety 264 and the secondary molecule 242. The sample 202 can be washed to remove unbound tertiary molecules 262.

As shown in panel 280, the sample 202 is mixed with an electron mediator solution, and is applied to the probe 120. Different electron mediator solutions can be used, depending on the reactive enzyme 266. For example, if the reactive enzyme 266 includes HRP, the electron mediator solution can include water-soluble substrates such as ABTS (2,2'-Azinobis [3-ethylbenzothiazoline-6-sulfonic acid]-diammonium salt), OPD (o-phenylenediamine dihydrochloride), and/or TMB (3,3',5,5'-tetramethylbenzidine). As another example, if the reactive enzyme 266 includes alkaline phosphatase, the electron mediator solution can include water-soluble substrates such as PNPP (p-nitrophenyl phosphate). As another example, if the reactive enzyme 266 includes beta-galactosidase, the electron mediator solution can include water-soluble substrates such as ONPG (o-nitrophenyl-β-D-galactopyranoside), Nap-Gal (Naphthol-AS-B1-beta-D-galactopyranosidase), and/or MUm-Gal (4-Methylumbelliferyl-beta-D-galactopyranosidase).

Due to a magnetic field induced by the magnet assembly 160 underneath the probe 120, the magnetic bead 206 is attracted towards the probe 120. Further, due to the potential induced across the working electrode 122c and reference electrode 122a of the probe 120, an oxidation-reduction reaction is induced between the electron mediators and the oxidizing enzyme. As a result, a current is induced from the working electrode 122c across counter electrode 122b of the probe 120. In turn, this current is converted into a voltage signal by the operational amplifier 112a, the voltage signal is digitized by the ADC 130, and the digitized voltage signal in interpreted by the MCU 140.

In general, the current induced in the probe 120 can correlate with the presence and/or concentration of the analyte 204 in the sample 202. For example, if the sample 202 contains a relatively high concentration of the analyte 204, a greater number of analytes 204 will be captured by the magnetic beads 206. In turn, a greater number of secondary molecules 242 and tertiary molecules 262 will also be captured by the magnetic bead 206, and brought into proximity with the probe 120. This results in a greater number of oxidizing enzymes available to react with the electron mediating solution. Accordingly, the oxidation-reduction reaction results in a relatively higher current across the counter electrode 122b.

In contrast, if the sample 202 contains a relatively low concentration of the analyte 204, a smaller number of analytes 204 will be captured by the magnetic beads 206. In turn, a smaller number of secondary molecules 242 and tertiary molecules 262 will also be captured by the magnetic bead 206, and brought into proximity with the probe 120. This results in a smaller number of oxidizing enzymes available to react with the electron mediating solution. Accordingly, the oxidation-reduction reaction results in a relatively lower current across the counter electrode 122b.

Further, if the sample 202 does not contain any analyte 202, substantially no analytes will be captured by the magnetic beads 204. In turn, substantially no secondary molecules 242 and tertiary molecules 262 will be captured by the magnetic beads. Thus, substantially no oxidizing enzymes will be available to react with the electron mediation solution. Accordingly, substantially no current will be induced across the counter electrode 122b.

In some cases, the MCU 140 can estimate an absolute concentration and/or relative concentration of the analyte 204 based on the induced current. For example, in some implementations, the correlation between induced current and the analyte concentration can be empirically determined (e.g., by obtaining samples having known concentrations of an analyte, measuring the induced current that results from the analysis process, and deriving a function that describes the relationship between the concentration and the induced current). Subsequently, the concentration of an unknown sample can be estimated by calibrating an observed current measurement according to the determined correlation. In some cases, the correlation between induced current and the analyte concentration can differ, depending on the analyte, the magnetic beads, the secondary and tertiary molecules, and/or other parameters. Thus, different correlations can be determined for each set of parameters, and can be selectively applied as appropriate to interpret a current measurement.

In general, a magnetic bead 206 include one or more inner magnetic cores and an outer coating, e.g., a capping polymer. The magnetic cores can be monometallic (e.g., Fe, Ni, Co), bimetallic (e.g., FePt, SmCo, FePd, FeAu) or can be made of ferrites (e.g., $Fe_2O_3$, $Fe_3O_4$, $MnFe_2O_4$, $NiFe_2O_4$, $CoFe_2O_4$). The magnetic particles can be nanometers or micrometers in size, and can be diamagnetic, ferromagnetic, paramagnetic, or superparamagnetic, in which size corresponds to an average diameter or average length. For example, the magnetic particles can have a size of approximately 10 μm, approximately 1 μm, approximately 500 nm, approximately 300 nm, or approximately 100 nm. In some cases, magnetic particles having a size of approximately 10 μm can be beneficial in reducing the degree of sedimentation during an assay. Other particle sizes are possible as well. The outer coating of a particle can increase its water-solubility and stability and also can provide sites for further surface treatment with binding moieties.

In general, a binding moiety is a molecule, synthetic or natural, that specifically binds or otherwise links to, e.g., covalently or non-covalently binds to or hybridizes with, a target molecule, or with another binding moiety (or, in certain embodiments, with an aggregation inducing molecule). For example, the binding moiety can be a synthetic oligonucleotide that hybridizes to a specific complementary nucleic acid target. The binding moiety can also be an antibody directed toward an antigen or any protein-protein interaction. Also, the binding moiety can be a polysaccharide that binds to a corresponding target. In certain embodiments, the binding moieties can be designed or selected to serve, when bound to another binding moiety, as substrates for a target molecule such as enzyme in solution. Binding moieties include, for example, oligonucleotides, polypeptides, antibodies, and polysaccharides. As an example, streptavidin has four sites (binding moieties) per molecule that will be recognized by biotin. For any given analyte, e.g., a specific type of cell having a specific surface marker, there are typically many known binding moieties that are known to those of skill in the relevant fields.

Figure 3:
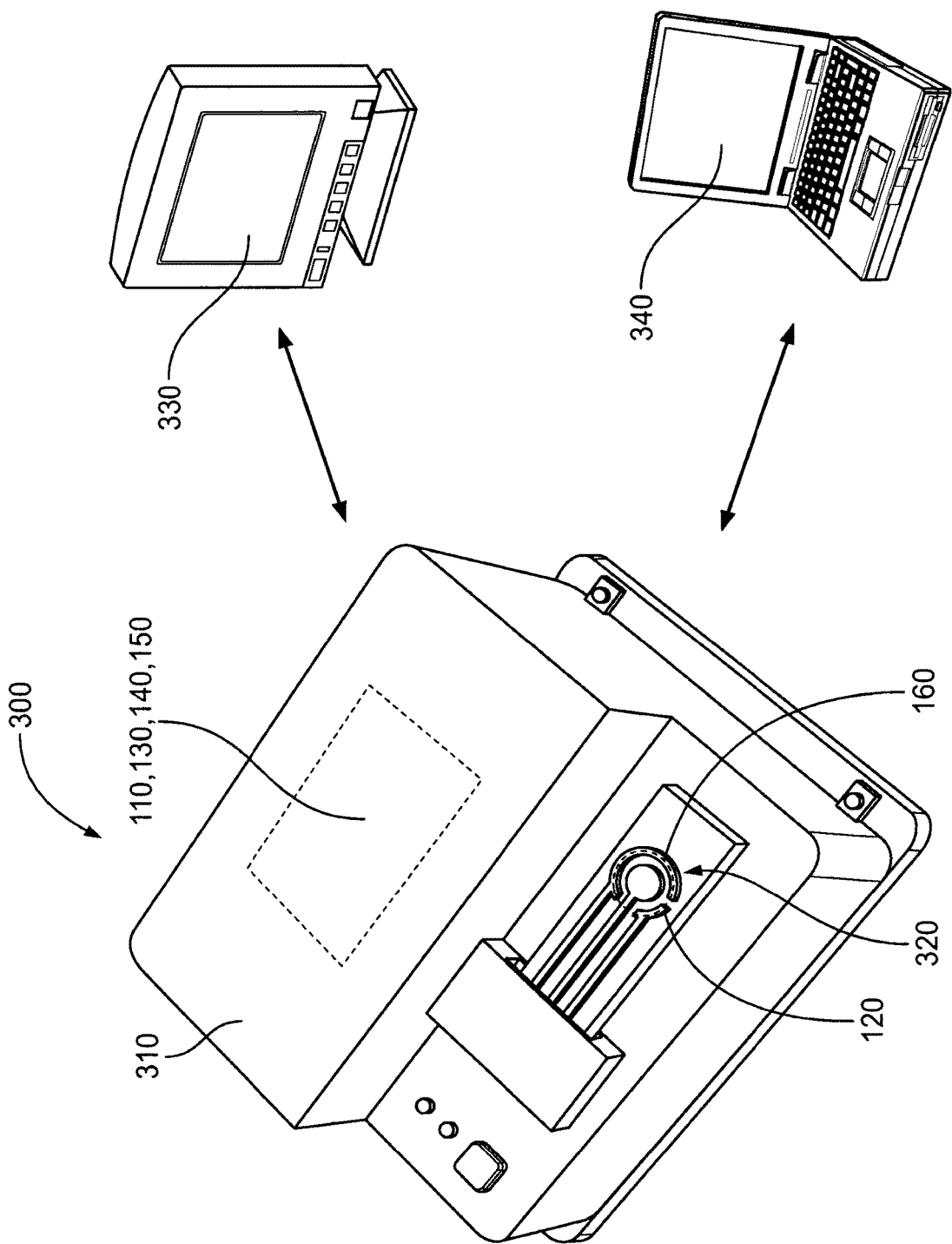
FIG. 3 is a diagram of another example of an instrument for examining analytes.

In some cases, the system can be implemented as an analytical instrument. As an example, FIG. 3 shows an instrument 300 for examining analytes using magnetic electrochemical sensing. The instrument 300 includes a housing 310 enclosing the potentiostat 110, ADC 130, MCU 140, and DAC 150 shown in FIG. 1. The instrument 300 also includes a well 320 exposed along the exterior of the housing 300, with the probe 120 positioned along the bottom of the well 320, and the magnet assembly 160 positioned beneath the probe 120. This configuration enables a user to apply a fluid sample (e.g., a sample that has been treated in accordance with the process described with respect to FIG. 2) to the well 320 such that it is rests atop the probe 120, and ascertain the presence and/or prevalence of a particular analyte in the fluid sample using the instrument 300. In some cases, the instrument 300 can output information regarding the analyzed fluid sample onto a display device 330 (e.g., a display screen or monitor) and/or output the information to a computing device 340 for further analysis (e.g., a computer, a smartphone, a server system, or other computing device).

In the example shown in FIG. 3, an instrument includes a single well with a single probe for analyzing a single sample at a time. However, in some cases, an instrument can include multiple different wells and probes, such that multiple samples can be analyzed simultaneously or sequentially. This can be useful, for example, as it enables a user to process a number of samples in a more efficient manner.

As an example, FIGS. 4A and 4B show an instrument 400 in an assembled view and an exploded view, respectively. As shown in FIGS. 4A and 4B, the instrument 400 includes a housing 410, several wells 420*a-h* exposed along the exterior of the housing 400, and a magnet assembly 160*a-h* positioned beneath each well 410*a-h*. Further, the instrument 400 includes several potentiostats 110*a-h*, each electrically coupled to a respective probe 120*a-h* positioned along the bottom of a corresponding well 420*a-h*. In a similar manner as described with respect to FIG. 3, a user can apply one or more fluid samples (e.g., samples that have been treated in accordance with the process described with respect to FIG. 2) to one or more of the wells 420*a-h*, and ascertain the presence and/or prevalence of particular analytes in the fluid samples using the instrument 400. Similarly, the instrument 400 can output information regarding the analyzed fluid sample onto a display device 430 (e.g., a display screen or monitor) and/or output the information to a computing device 440 for further analysis (e.g., a computer, a smartphone, a server system, or other computing device).

In some cases, the magnetic assembly 160*a-h* can each include one or more individual magnets corresponding to each well 420*a-h* (e.g., an embedded magnet under each well 420*a-h*. In some cases, the magnetic assembly 160*a-h* can include one or more magnets that extend between multiple different wells 420*a-h*).

In some cases, the instrument 400 can include a multiplexer to electrically couple the outputs of the potentiostats to an MCU, such that the MCU can selectively retrieve signals from each of the potentiostats, and selectively determine the properties of each of the samples in the wells.

Figure 4C:
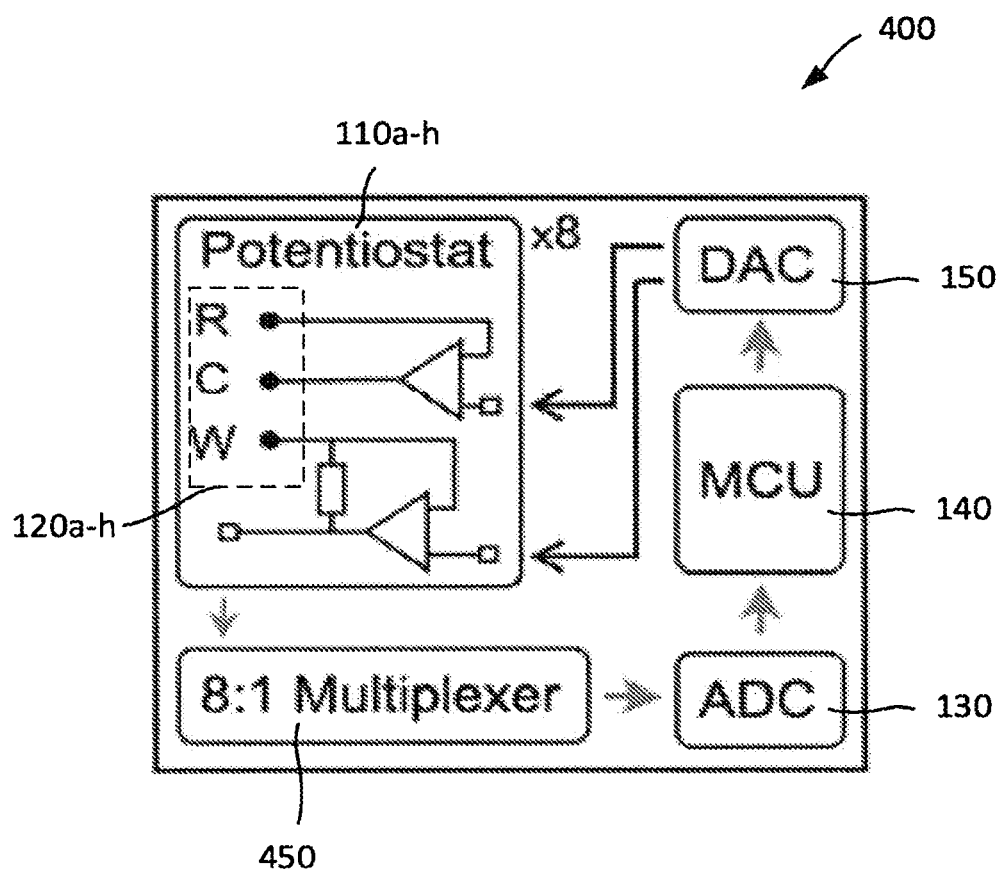
FIG. 4C is a schematic diagram of the instrument shown in FIGS. 4A and 4B.

As an example, the instrument 400 is shown schematically in FIG. 4C. The instrument 400 includes several potentiostats 110*a-h* (e.g., 8 total as indicated by the "x8" label in FIG. 4C), each electrically coupled to a respective probe 120*a-h*. The instrument 400 also includes an ADC 130, a MCU 140, a DAC 150, and a magnet assembly 160*a-h*. Each of these components can operate similarly as described with respect to FIG. 1.

In this example, however, the instrument 400 includes a multiplexer 450 electrically coupling the outputs of the potentiostats 110*a-h* to the MCU 140 (via the ADC 130). The multiplexer 450 selects voltage signals from one of the potentiostats 110*a-h*, and forwards the signal to the ADC 130 and the MCU 140. Thus, a single ADC 130 and MCU 140 can be configured to selectively retrieve signals from multiple different probes 120*a-h*, and selectively determine the properties of each of the samples in the wells. In some cases, the multiplexer 450 can be controlled by a user (e.g., through a switch, dial, button, touchscreen, or other control mechanism). In some cases, the multiplexer 450 can be controlled by the MCU 140 (e.g., through a control signal transmitted from the MCU 140 to the multiplexer 450 indicating a particular selected well). This can be useful, for example, as it enables the MCU 140 to automatically select wells for analysis (e.g., to automatically collect measurements from the wells in a sequential manner, or according to some other pattern).

Although the instrument 400 shown in FIG. 4 includes eight wells (and eight corresponding probes and potentiostats), this is merely an illustrative example. In practice, a device can include any number of wells, probes, and potentiostats (e.g., one, two, three, four, five, or more).

Further, in some cases, a multiplexer can be used to electrically couple the outputs of multiple different probes to a common potentiostat. This can be useful, for example, as it enables a single potentiostat to measure the properties of multiple different samples, which may decrease the complexity and/or cost of producing the instrument.

Figure 5B:
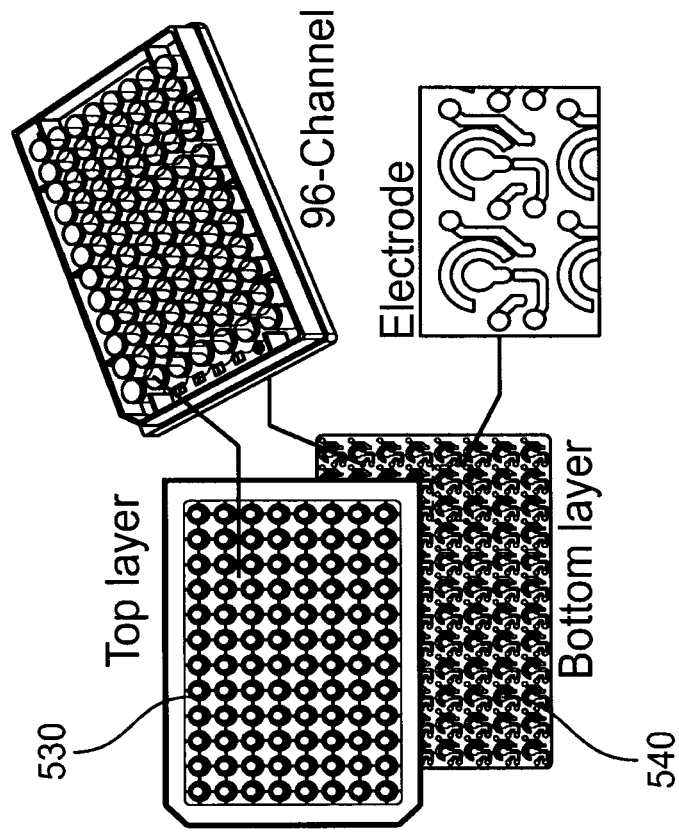
FIGS. 5A and 5B are diagrams of another example of an instrument for examining analytes.
Figure 5A:
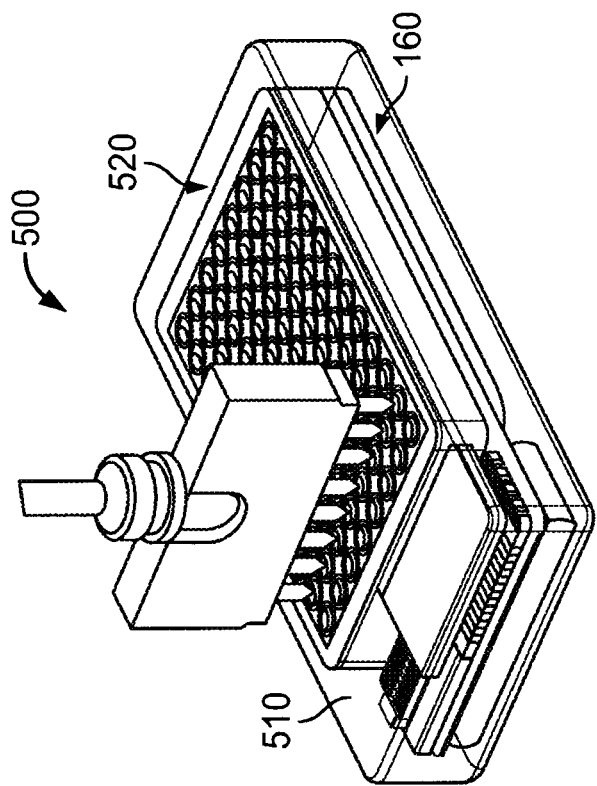
Figure 5C:
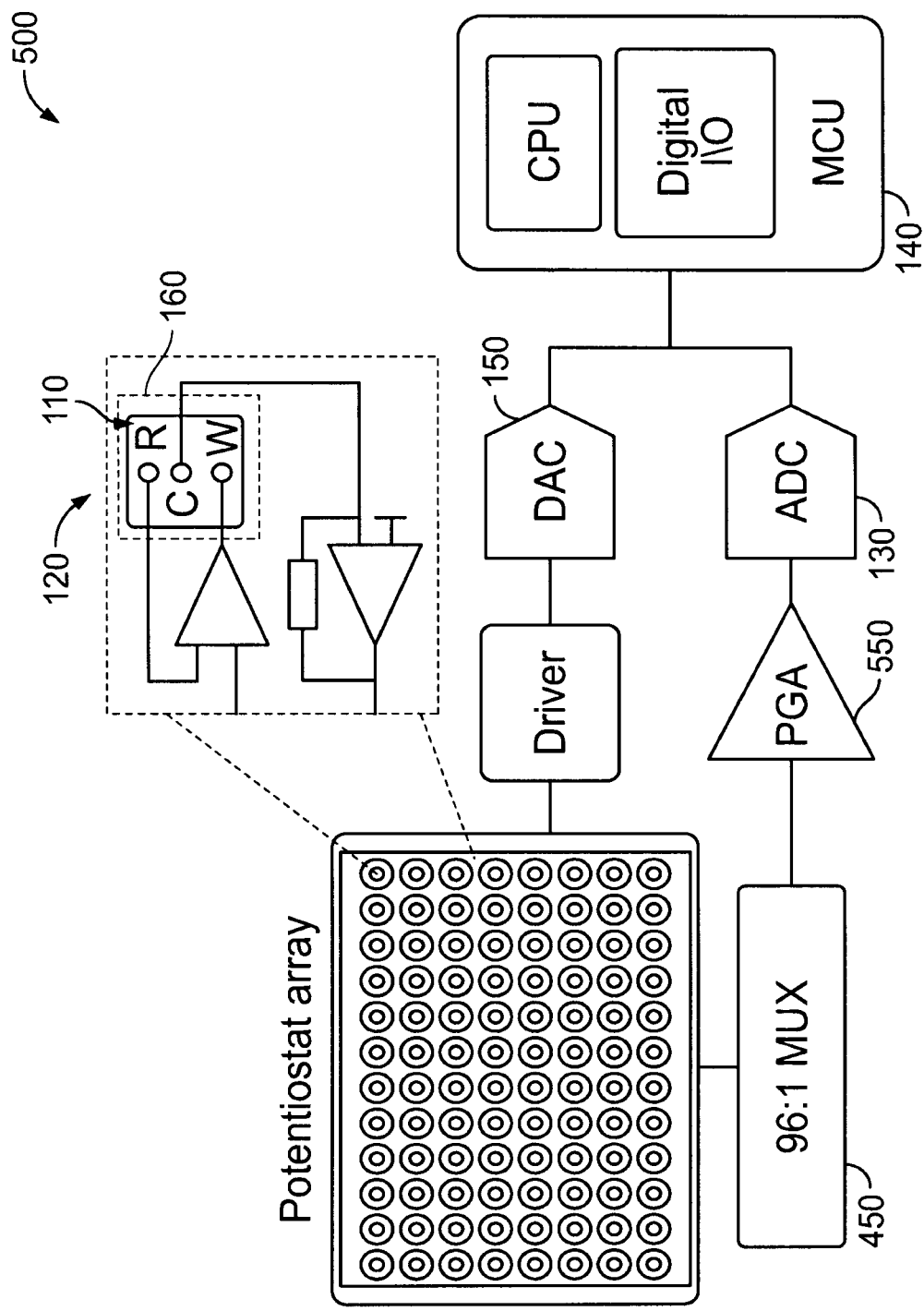
FIG. 5C is a schematic diagram of the instrument shown in FIGS. 5A and 5B.

Another example of an instrument 500 is shown in FIGS. 5A-C. The instrument 500 includes a housing 510, multiple wells 520 exposed along the exterior of the housing 510, and a magnet assembly 160 positioned beneath each well 520. Further, the instrument 500 includes several potentiostats 110, each electrically coupled to a respective probe 120 positioned along the bottom of a corresponding well 520.

The wells 520 can have a similar arrangement and similar dimensions as a standardized 96 well plate (e.g., a 96 well plate manufactured according to specifications established by the American National Standards Institute, ANSI, and/or the Society for Laboratory Automation and Screening, SLAS). This can be useful, for example, as it enables a user to use commonly available equipment (e.g., a standardized multi-channel pipette) to load and unload samples from the instrument 500.

As shown in FIG. 5B, the wells 520 and the electrodes of the potentiostats 110 can be implemented using a series of layers. For instance, the wells 520 can be provided in a top layer 530, and the electrodes of the potentiostats 110 can be provided on a bottom layer 540 (e.g., a substrate, such as a printed circuit board). The top layer 530 can be positioned above the bottom layer 540, such that each of the wells 520 is aligned with a corresponding electrode below. This can be useful, for example, as the instrument 500 may be manufactured more easily (e.g., as multiple sets of electrodes can be manufactured using a single PCB fabrication process).

In some cases, the electrodes of the potentiostats 110 can be formed on a substrate, such as a ceramic substrate, a glass substrate, a rigid plastic substrate, a paper substrate, a flexible polymer substrate (e.g., PDMS), a silicon substrate, and/or a PCB. In some cases, the magnet assembly can include one or more magnets positioned relative to the substrate such that a magnetic field from the magnet extends through the substrate (e.g., to attract magnetic beads to the substrate and the electrodes formed thereon). In some cases, the magnet assembly also can be formed on a substrate (e.g., the same substrate as one or more electrodes, or a separate substrate).

The instrument 500 is shown schematically in FIG. 5C. In a similar manner as described with respect to FIG. 4C, the instrument 500 includes several potentiostats 110, each electrically coupled to a respective probe 120. The instrument 500 also includes an ADC 130, a MCU 140, a DAC 150, and a magnet assembly 160. Similarly, the instrument 500 includes a multiplexer 450 electrically coupling the outputs of the potentiostats 110 to the MCU 140 (via the ADC 130). The multiplexer 450 selects voltage signals from one of the potentiostats 110, and forwards the signal to the ADC 130 and the MCU 140. Thus, a single ADC 130 and MCU 140 can be configured to selectively retrieve signals from multiple different probes 120, and selectively determine the properties of each of the samples in the wells.

The instrument 500 also includes a programmable gain amplifier (PGA) 550 electrically coupled between the multiplexer 450 and the ADC 130. The PGA 500 can be configured to automatically change the amplification gain of signals from the multiplexer 450, and to maximize or otherwise increase the detection dynamic range of the instrument 500.

The instrument 500 also includes a driver 560 electrically coupled between the DAC 150 and the potentiostats 110. The driver 560 can be configured to deliver current to the electrodes of the potentiostats based on signals received from the DAC 150. This can be beneficial, for example, as some DAC might be incapable or otherwise unsuitable for delivering current to a large number of devices.

Figure 6A:
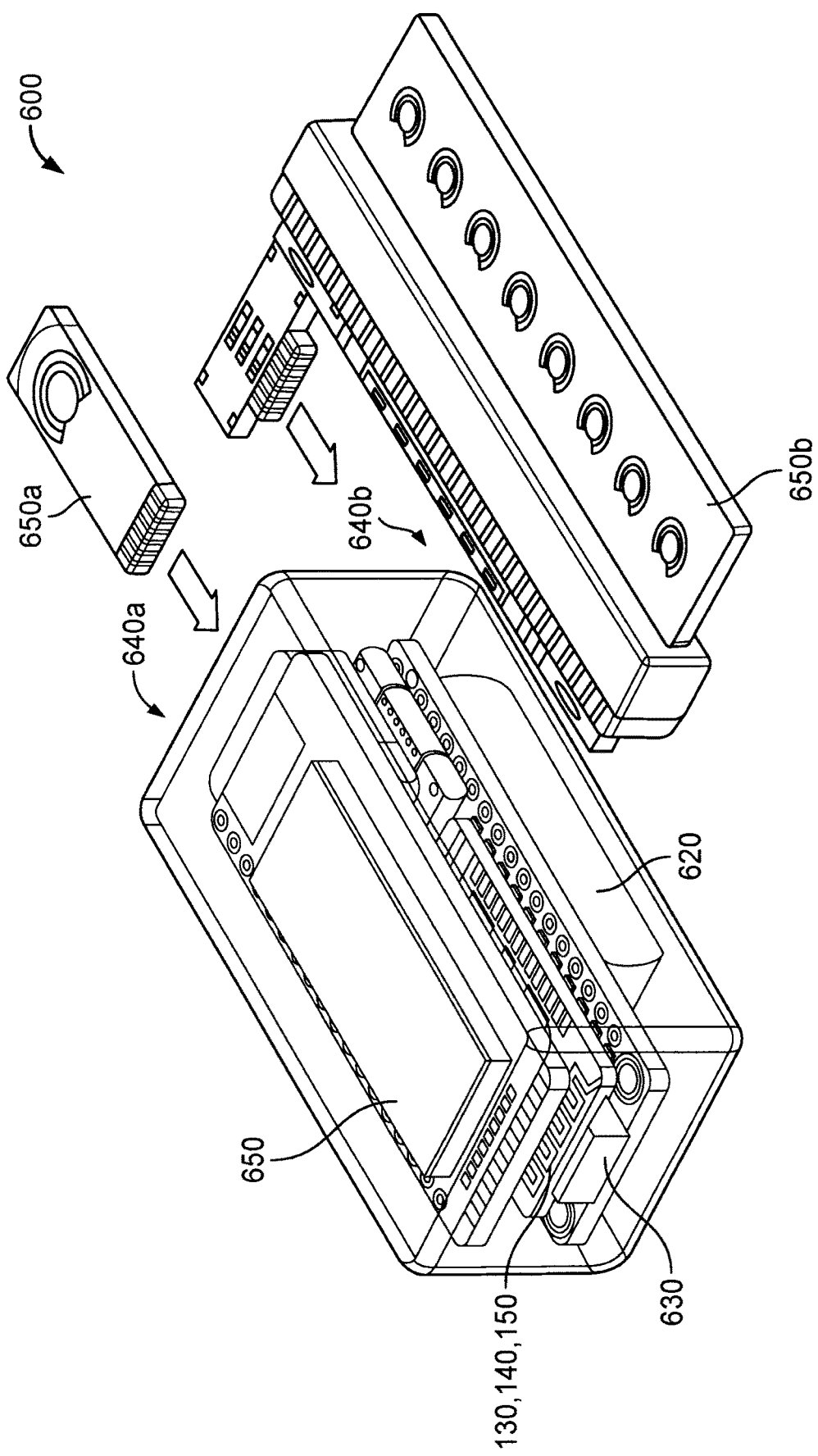

In some cases, the system can be implemented as a portable device. As an example, FIG. 6A shows a portable device 600 for examining analytes using magnetic electrochemical sensing. The device 600 includes a housing 610 enclosing an ADC 130, an MCU 140, and a DAC 150. The device 600 also includes a battery module 620, a communications interface 630, sample interfaces 640a and 640b, and a display device 650.

In general, the potentiostat 110, the ADC 130, the MCU 140, and the DAC 150 can function similarly as those described with respect to FIG. 1. For example, the ADC 130 can receive voltage signals from the potentiostat 110 corresponding to a current induced from the working electrode 122c across counter electrode 122b, digitize the voltage signal, and transmit the digitized signal to the MCU 140 for processing. Similarly, the MCU 140 can process the digitized voltage signal to determine the presence and/or prevalence of a particular analyte, and control the operation of the potentiostat via the DAC 150.

In this example, the device 600 does not include sample probe within the housing 610. Instead, the device 600 includes two sample interfaces 640a and 640b (e.g., communications ports or connectors), through which a user can insert a sample card containing one or more probes (and one or more corresponding wells and magnet assemblies).

For example, as shown in FIG. 6B, a user can insert a sample card 650a having a single probe (and a single corresponding well and magnet assembly) into the sample interface 640a, and the probe can be electrically coupled to a corresponding potentiostat within the housing 610. The sample card 650a can couple to the sample interface 640a, for example, via a card edge connector (e.g., a pin header, receptacle, or socket) included as a part of the substrate or positioned on the substrate of the sample card 650a. This enables the substrate to be removably attachable to the rest of the device 600 (e.g., the housing and/or other portions of the device 600) such that the electrodes are coupled to the potentiostat upon attaching the substrate to the device 600 (e.g., the housing).

As another example, as shown in FIG. 6C, a user can insert a sample card 650b having multiple probes (and multiple corresponding wells and magnet assemblies) into the sample interface 640b, and each of the probe can be electrically coupled to a corresponding potentiostat within the housing 610. Similarly, the sample card 650b can couple to the sample interface 640b, for example, via a card edge connector (e.g., a pin header, receptacle, or socket) included as a part of the substrate or positioned on the substrate of the sample card 650b. Similarly, this enables the substrate to be removably attachable to the rest of the device 600 (e.g., the housing and/or other portions of the device 600) such that the electrodes are coupled to the potentiostat upon attaching the substrate to the device 600 (e.g., the housing).

This can be useful, for example, as it enables a user to customize the device 600 according to his needs. Further, this enables a user to partially disassemble the device 600, which can facilitate maintenance, and may be more convenient for storage or transport. In some cases, one or more potentiostats can also be included on the sample cards (e.g., instead of being included within the housing 610).

Figure 6E:
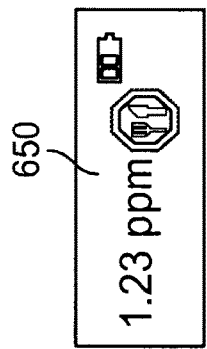
FIGS. 6E and 6F are diagrams of an example of a display device.
Figure 6F:
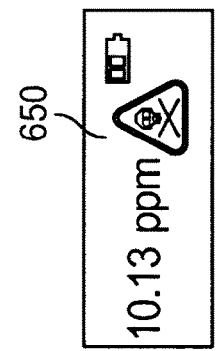
Figure 6D:
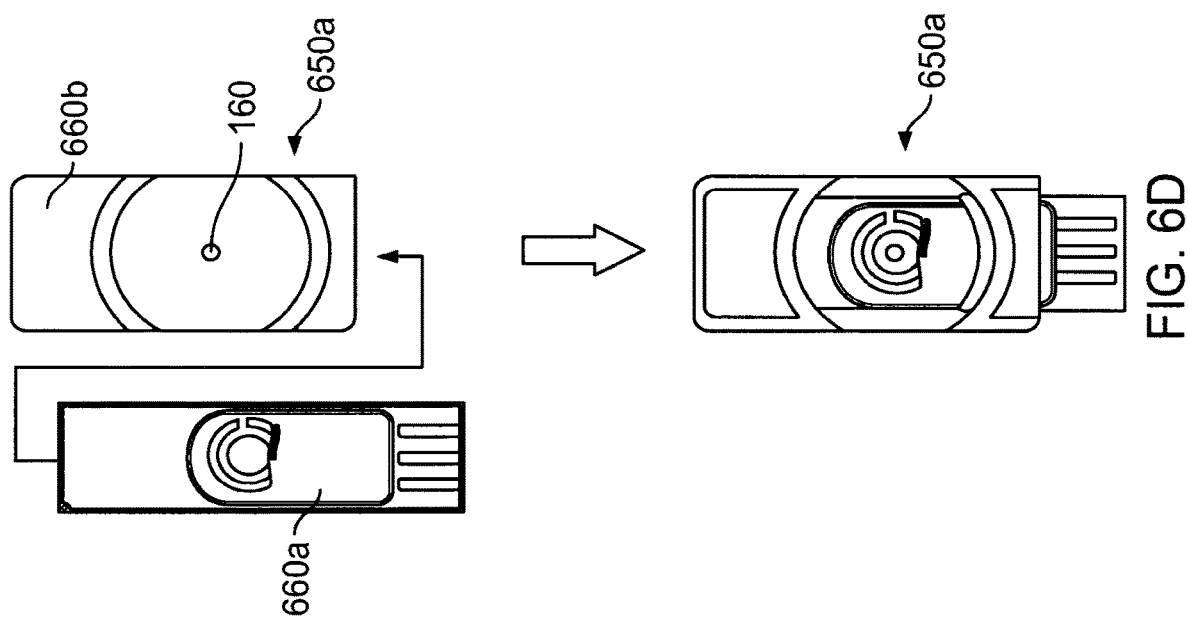
FIG. 6D is a diagram of an example of a sample card.

In some cases, a sample card can be constructed from multiple detachable parts. For example, as shown in FIG. 6D, the sample card 650a can have an electrode portion 660a, and a sleeve portion 660b containing the magnet assembly 160. The electrode portion 660a can be inserted into the sleeve portion 660b, such that the electrodes are positioned above the magnet assembly (e.g., such that one or more magnets of the magnet assembly are positioned beneath each of the electrode locations). Further, the electrode portion 660a can be separated from the sleeve portion 660b, which allows the electrode portion 660a and/or the sleeve portion 660b portion to be separately replaced (e.g., to separate a substrate having the electrodes from the magnet assembly).

In some cases, the sample interface 640a and sample interface 640b can each include a receptacle with pins or other electrical contacts arranged to electrically connect to corresponding electrodes of the card edge connector.

In some cases, the device can be configured to automatically select between sample cards inserted into the sample interfaces and/or between probes on the sample cards using the pins of the sample interfaces 640a and 650b. For example, the sample interfaces 640a and 650b can each include a pin for detecting the presence of a sample card (e.g., a pin that receives a signal from a sample card when the sample card is inserted), and a pin for selecting one or more of the probes on a sample card (e.g., a pin that transmits a signal identifying a particular probe to the inserted sample card).

The communications interface 630 enables the device 600 to communicate with other computing devices (e.g., transmit measurement data to other computing devices and/or receive commands from other computing devices). For example, the communications interface 630 can be a communications port or connector (e.g., an electronic communication interface, such as a universal serial bus, USB, connector, plug, socket, or receptacle) that provides a communications channel between the device 600 and another computing device. In some cases, the communications interface 630 can be a wireless communications interface (e.g., a wireless transceiver, such as a Wi-Fi or Bluetooth transceiver) that enables the device 600 to communicate wirelessly to other computing devices.

The display device 650 visually presents information to a user. In some cases, the display device 650 can be a liquid crystal display (LCD), a light emitting diode (LED) display, or an organic light emitting diode (OLED) display. In some implementation's, the display device 650 can display the result of the analysis conducted by the MCU 140 (e.g., display whether a particular analyte is present in the sample and/or information regarding the prevalence of the analyte in the sample. As an example, FIG. 6E shows the display device 650 indicating a first concentration of an analyte in a sample (e.g., a relatively safe amount of a particular analyte), and FIG. 6F shows the display device 650 indicate a second concentration of an analyte in a sample (e.g., a relatively dangerous amount of a particular analyte).

In some cases, one or more of the systems described herein can be controlled via a computing device, such as a computer, a smartphone, a server system, or other computing device. For instance, the device 600 can establish a communications channel with a computing device via the communications interface 630, and use the channel to transmit measurement data to the computing device and receive commands from the computing device.

In some cases, the computing device can execute a control application associated with the magnetic electrochemical sensing system. The control application can provide various functions related to the operation of the system. For example, the control application can present the user with a user interface presenting various options and commands for operating the system, and receive inputs from the user selecting particular options and commands. Further, the control application can process measurement data received from the system (e.g., converting digitized voltage signals into an indication of a current measurement, determining whether a particular analyte is present based on the current, and/or determine a concentration of a particular analyte based on the current).

Figure 7C:
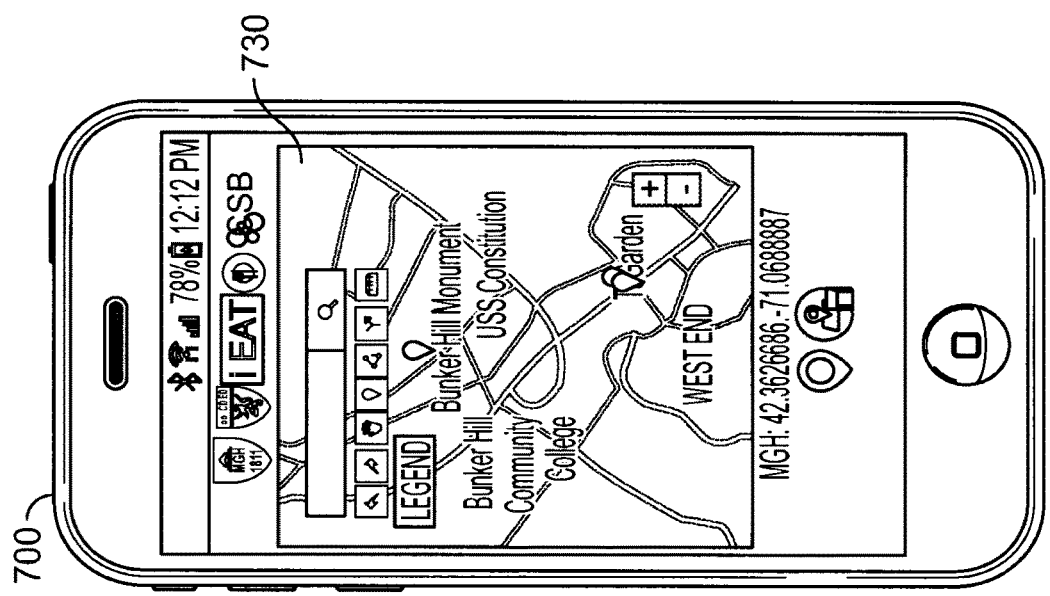
FIGS. 7A-7C are diagrams of an example of graphical user interfaces (GUIs) of a control application.
Figure 7B:
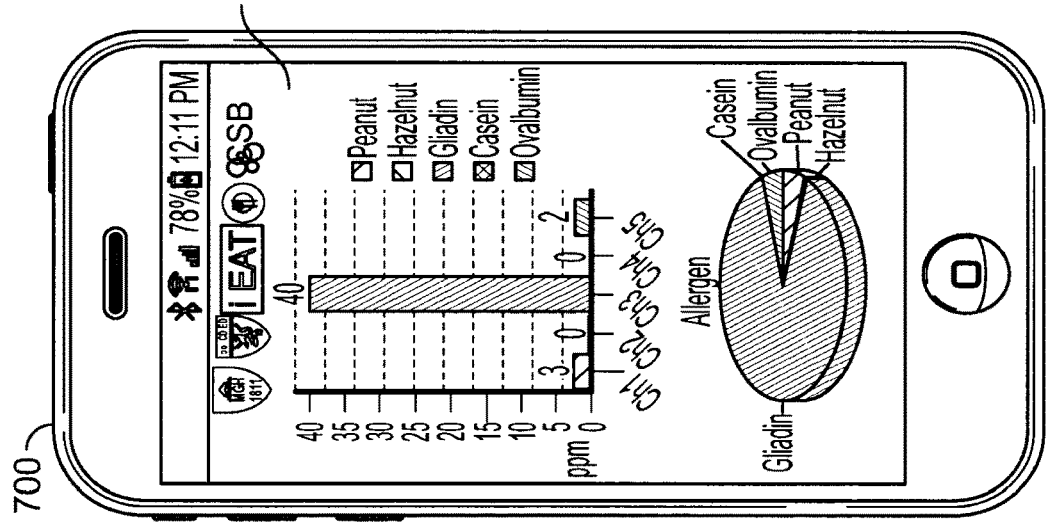
Figure 7A:
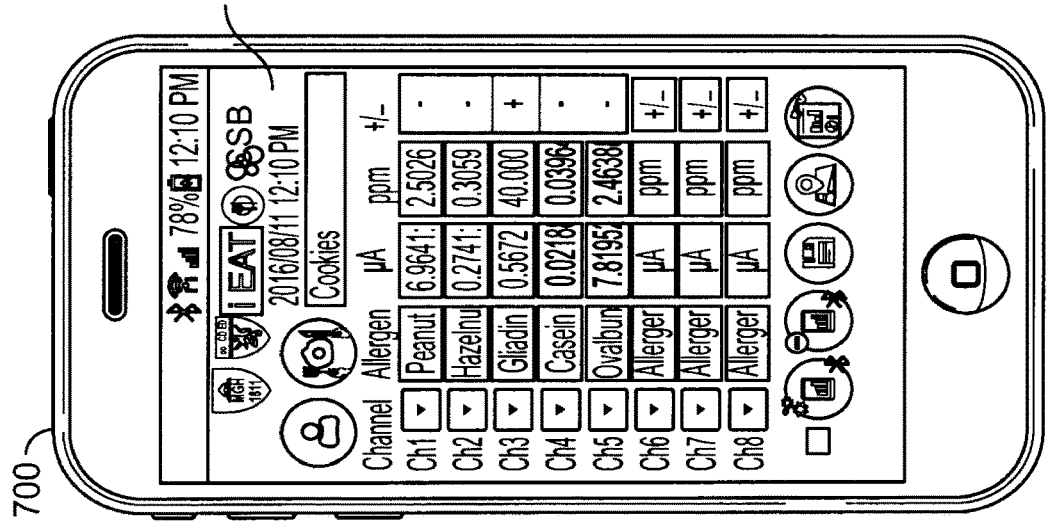

To illustrate, FIG. 7A shows a smartphone 700 executing a control application associated with the magnetic electrochemical sensing system. The control application presents a graphical user interface (GUI) 710 to the user, presenting various options for configuring the system (e.g., an option to select a particular sample or "channel" for measurement, and an option to enter a particular analyte to be analyzed). Further, the GUI 710 displays the measurement information associated with each of the selected wells (e.g., an indication of the current measured in a selected sample, and an indication of the corresponding analyte concentration based on the measurement). Further, the GUI 710 can display a warning or notification to the user (e.g., if the concentration of a particular analyte is sufficiently high, so as to be potentially unsafe, or if the concentration of a particular analyte exceeds a particular threshold or reference value).

As another example, as shown in FIG. 7B, the control application can present a GUI 720 to a user that presents more detailed information regarding a particular sample. For example, if a user used the system to analyze a particular substance (e.g., a food) with respect to several different analytes (e.g., allergens), the GUI 720 can summarize the results of these analyses, and visually present the results to the user (e.g., in the form of a chart displaying the concentration of each allergen relative to each other). This enables the user to quickly identify the presence and prevalence of certain analytes in the sample.

As another example, as shown in FIG. 7C, the control application can present a GUI 730 to a user that presents geographical information regarding the samples. For example, the GUI 730 can display a geographical map, and display points of interest identifying the location in which certain samples were collected. This enables the user to quickly identify the source of particular samples, such as that he can retrieve and/or avoid those locations in the future. For example, a user can input the location of various stores and restaurants from which he obtained food samples, and associate the results of the sample analyses with each appropriate location. If the sample from a particular location contained a high concentration of a particular allergen, the GUI 730 can visually indicate this to the user (e.g., using a color coded icon), such that the user can avoid that location in the future. If the sample from a particular location contained a low concentration of a particular allergen, the GUI 730 can visually indicate this to the user (e.g., using a differently colored icon), such that the user can readily identify that location for future visits.

In some cases, the magnetic electrochemical sensing system can be provided as a part of an analysis kit. In addition to the sensing system, the kit can include materials that facilitate preparation of samples for analysis.

Figure 8:
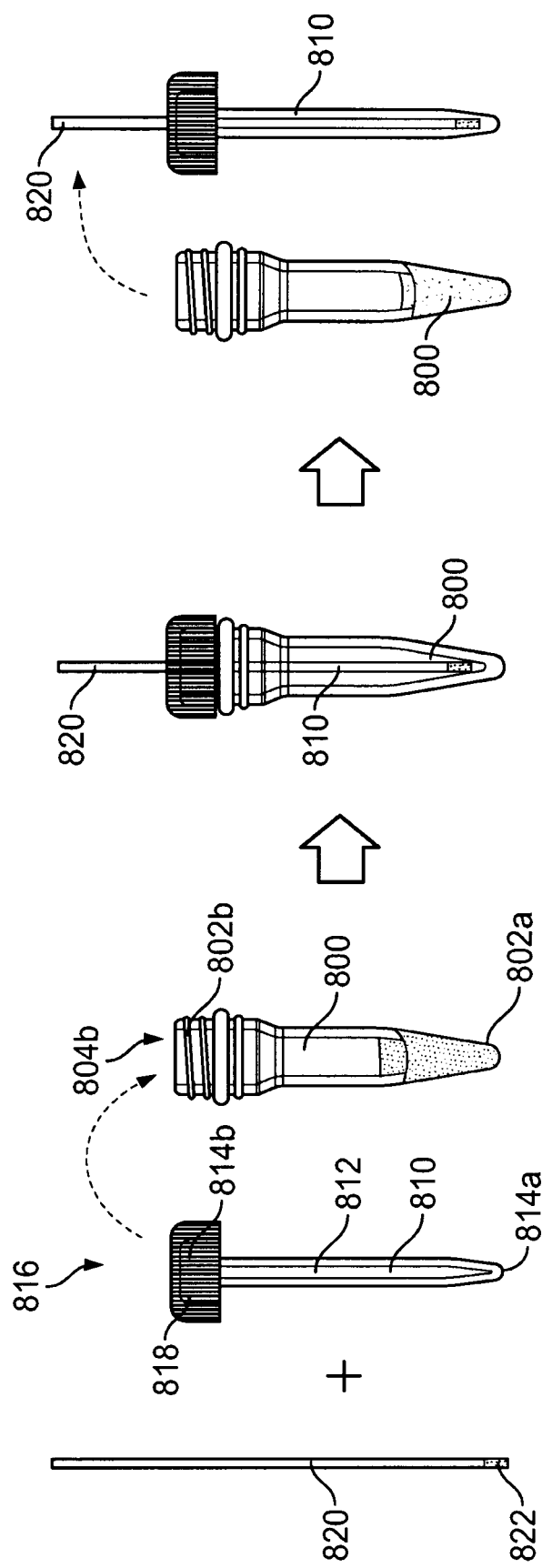
FIG. 8 is a diagram of an example of a sample processing tools.

For instance, as shown in FIG. 8, a kit can include sample processing tools, such as sample tubes 800, sleeves 810, and magnetic bars 820.

The sample tube 800 is configured to receive a fluid sample to be analyzed using the sensing system, such as any of the sensing systems described herein. The sample tube 800 is sealed on a first end 802a, and defines an aperture 804b on a second end 802b through which a sample can be deposited.

The sleeve 810 defines an elongated channel 812. The channel 812 is sealed on a first end 814a, and defines an aperture 816 on a second end 814b. The channel 812 is dimensioned to accept the magnetic bar 820 inserted through the aperture 816 (e.g., the channel 812 has a diameter that is slightly larger than a diameter of the magnetic bar 820). The sleeve 810 also includes a cap 818 configured to physically couple to the sample tube 800 (e.g., through screw threads on each).

The magnetic bar 820 includes a magnet 822 positioned on its tip, and is configured to insert into the sleeve 810 via the aperture 816.

The sample tubes 800, the sleeves 810, and the magnetic bar 820 can be used to process samples for analysis by the sensing system (e.g., by collecting magnetic beads from a sample tube, transferring the collected magnetic beads to another sample tube).

Figure 9:
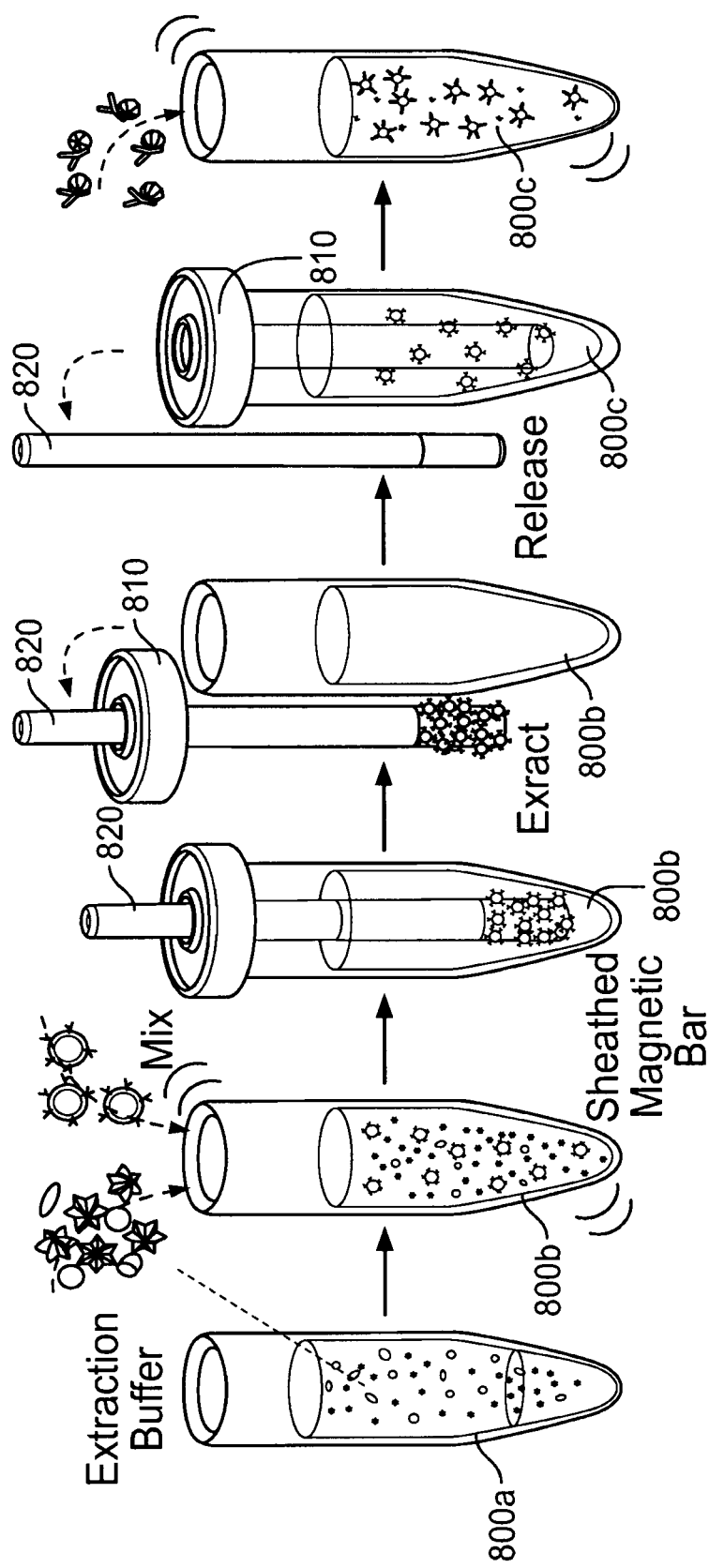
FIG. 9 is a diagram of an example of usage of the sample processing tools shown in FIG. 8.

As an example, as shown in FIG. 9, a user can insert a sample to be analyzed (e.g., a portion of a food product) into a first sample tube 800a containing an extraction buffer. The extraction buffer is used to extract target anaytes (e.g., proteins) for subsequent analysis (e.g., by solubilizing protein and/or peptides into buffer). Various substances can be used as an extraction buffer, including 2-mercaptoethanol, tris-(2-carboxyethyl)phosphine augmented with guanidine (TECP/GUA), TECP with N-lauroylsarcosine, phosphate buffered saline (PBS) buffer, Tris-HCl buffer, and/or ethanol (e.g., 60% ethanol). As an example, a 2-mercaptoethanol buffer solution can increase the protein extractability of certain samples (e.g., heated or unheated food products), and can be suitable for reducing protein disulfide bonds and cleaving intermolecular disulfide bonds (e.g., those between subunits) to allow the subunits of a protein to separate, such that that each peptide migrates into buffer solution. As another example, odor-free tris-(2-carboxyethyl)phosphine can be used for the reduction of protein and peptide disulfides. As yet another example, guanidine hydrochloride is a strong chaotropic agent, and can be useful for the denaturation and subsequent refolding of proteins. This strong denaturant can solubilize insoluble or denatured proteins. As yet another example, N-Lauroylsarcosine is an anionic surfactant, can be used for solubilization and separation of proteins and peptides. In some cases, cocktail extraction buffer solutions (e.g., an extraction buffer solution containing multiple different types of constituent buffer solutions) can be used for extraction. This can be benefical, for example, as it enables extraction in a wide variety of use cases, simplifies the extraction process, and/or enhances the user experience.

The user subsequently transfers the extracted material from the first sample tube 800a to a second sample tube 800b containing a sample buffer (e.g., PBS or PBS containing 1% bovine serum albumin, BSA). The user also adds a solution containing magnetic beads into the sample tube 800b (e.g., magnetic beads coated with binding moieties specific to a particular analyte of interest, such as a particular allergen). The user mixes the contents of the second sample tube 800b (e.g., by sealing the second sample tube 800b with a cap and sleeve 810, and shaking the second sample tube 800b.

The user separates the magnetic beads (and captured analytes) by inserting a magnetic bar 820 into the sleeve 810. The magnet 822 from bar 820 attracts the magnetic beads to the periphery of the sleeve 810, such they are retained. The user subsequently extracts the sleeve 810 with the magnetic bar 820 still inserted, thereby removing the magnetic beads (and captured analytes) from the second sample tube 800b.

The user inserts the sleeve 810 (with the magnetic bar 820 still inserted) into a third sample tube 800c containing an electron mediator solution (e.g., a solution containing TMB, ARTS, OPD, PNPP, ONPG, Nap-Gal, and/or MUm-Gal). The user subsequently removes the magnetic bar 820 from the sleeve 810. This causes the magnetic beads to release from the sleeve 810 and disperse into the third sample tube 800c. In this manner, the user can selectively remove the magnetic beads (and any molecules bond to the magnetic beads) from one sample tube, transfer them to another sample tube without the need for additional filtration or centrifugation equipment.

The user also adds a solution containing second molecules (e.g., binding moieties) specific to the analyte and tertiary molecules specific to the second molecules and having a reactive enzyme (e.g., the secondary molecules 242 and tertiary molecules 262 described with respect to FIG. 2) into the third sample tube 800c. These secondary molecules 242 and tertiary molecules 262 become bound to the magnetic beads. The user shakes the third sample tube 800c, and transfers the contents of the third sample tube 800c to the sensing device for analysis (e.g., by depositing the contents of the third sample tube 800c onto the probe of the potentiostat).

In some cases, the kit can also include a heating device, for example as shown in FIG. 37. A heating device can be configured to heat sample tubes during the extraction process (e.g., by heating the sample tube and its contents for around 2 minutes at around 60° C.) to speed up the extraction process. In some cases, other heating devices (e.g., a microwave, oven, or heat lamp) can be used to heat a sample tube and its contents during the extraction process.

As described herein, due to a magnetic field induced by the magnet assembly underneath the probe, the magnetic beads are attracted towards the probe. Further, due to the potential induced across the working electrode and reference electrode of the probe, an oxidation-reduction reaction is induced between the electron mediators and the oxidizing enzyme. As a result, a current is induced from the working electrode across counter electrode of the probe. In turn, this current is converted into a voltage signal by the operational amplifier, the voltage signal is digitized by the ADC, and the digitized voltage signal in interpreted by the MCU.

In some implementations, a user can wash the samples between some or all of the steps described herein. For example, when transferring a sample between sample tubes, a user can use the sleeve 810 and the magnetic bar 820 to collect magnetic beads (and any bound molecules) from a tube, and transfer the magnetic beads to a sample tube containing a wash buffer. The user can remove the magnetic bar 820 to disperse the samples into the wash buffer. The user can subsequently reinsert the magnetic bar 820 into the sleeve 810 to recollect the magnetic beads, and continue with the sample preparation process. In this manner, the user can wash the magnetic beads (e.g., to remove unbound molecules) between some or all of the processing steps described herein.

Some implementations of subject matter and operations described in this specification can be implemented in digital electronic circuitry, or in computer software, firmware, or hardware, including the structures disclosed in this specification and their structural equivalents, or in combinations of one or more of them. For example, in some implementations, the systems 100, 300, 400, 500, 600, and 700, can be implemented, at least in part, using digital electronic circuitry, or in computer software, firmware, or hardware, or in combinations of one or more of them. In some implementations, a potentiostat (e.g., the potentiostat 110), an ADC (e.g., the ADC 130), an MCU (e.g., the MCU 140) and/or a DAC (e.g., a DAC 150), and/or a digital-to-analog converter (DAC) 150 can be implemented, at least in part, using digital electronic circuitry, or in computer software, firmware, or hardware, or in combinations of one or more of them.

Some implementations described in this specification can be implemented as one or more groups or modules of digital electronic circuitry, computer software, firmware, or hardware, or in combinations of one or more of them. Although different modules can be used, each module need not be distinct, and multiple modules can be implemented on the same digital electronic circuitry, computer software, firmware, or hardware, or combination thereof.

Some implementations described in this specification can be implemented as one or more computer programs, i.e., one or more modules of computer program instructions, encoded on computer storage medium for execution by, or to control the operation of, data processing apparatus. For example, the control application described herein with respect to FIG. 7 may be implemented as a computer program. A computer storage medium can be, or can be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Some of the processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and processors of any kind of digital computer. Generally, a processor will receive instructions and data from a read only memory or a random access memory or both. A computer includes a processor for performing actions in accordance with instructions and one or more memory devices for storing instructions and data. A computer may also include, or be operatively coupled to receive data from or transfer data to, or both, one or more mass storage devices for storing data, e.g., magnetic, magneto optical disks, or optical disks. However, a computer need not have such devices. Devices suitable for storing computer program instructions and data include all forms of non-volatile memory, media and memory devices, including by way of example semiconductor memory devices (e.g., EPROM, EEPROM, flash memory devices, and others), magnetic disks (e.g., internal hard disks, removable disks, and others), magneto optical disks, and CD ROM and DVD-ROM disks. The processor and the memory can be supplemented by, or incorporated in, special purpose logic circuitry.

To provide for interaction with a user, operations can be implemented on a computer having a display device (e.g., a monitor, or another type of display device) for displaying information to the user and a keyboard and a pointing device (e.g., a mouse, a trackball, a tablet, a touch sensitive screen, or another type of pointing device) by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

A computer system may include a single computing device, or multiple computers that operate in proximity or generally remote from each other and typically interact through a communication network. Examples of communication networks include a local area network ("LAN") and a wide area network ("WAN"), an inter-network (e.g., the Internet), a network comprising a satellite link, and peer-to-peer networks (e.g., ad hoc peer-to-peer networks). A relationship of client and server may arise by virtue of computer programs running on the respective computers and having a client-server relationship to each other.

Figure 10:
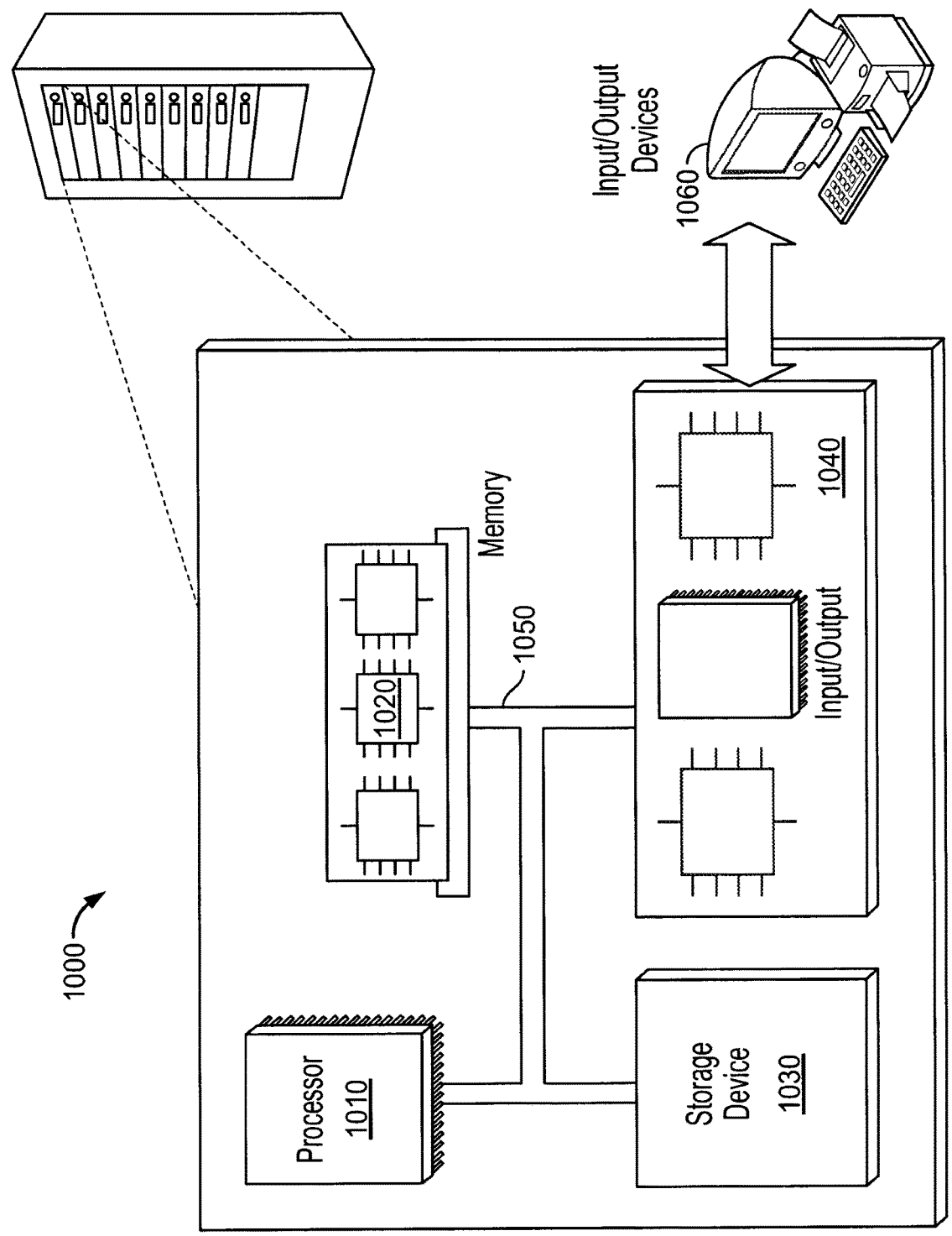
FIG. 10 is a diagram of an example of a computer system.

FIG. 10 shows an example computer system 1000 that includes a processor 1010, a memory 1020, a storage device 1030 and an input/output device 1040. Each of the components 1010, 1020, 1030 and 1040 can be interconnected, for example, by a system bus 1050. The processor 1010 is capable of processing instructions for execution within the system 1000. In some implementations, the processor 1010 is a single-threaded processor, a multi-threaded processor, or another type of processor. The processor 1010 is capable of processing instructions stored in the memory 1020 or on the storage device 1030. The memory 1020 and the storage device 1030 can store information within the system 1000.

The input/output device 1040 provides input/output operations for the system 1000. In some implementations, the input/output device 1040 can include one or more of a network interface devices, e.g., an Ethernet card, a serial communication device, e.g., an RS-232 port, and/or a wireless interface device, e.g., an 802.11 card, a 3G wireless modem, a 4G wireless modem, etc. In some implementations, the input/output device can include driver devices configured to receive input data and send output data to other input/output devices, e.g., keyboard, printer and display devices 1060. In some implementations, mobile computing devices, mobile communication devices, and other devices can be used.

Figure 42:
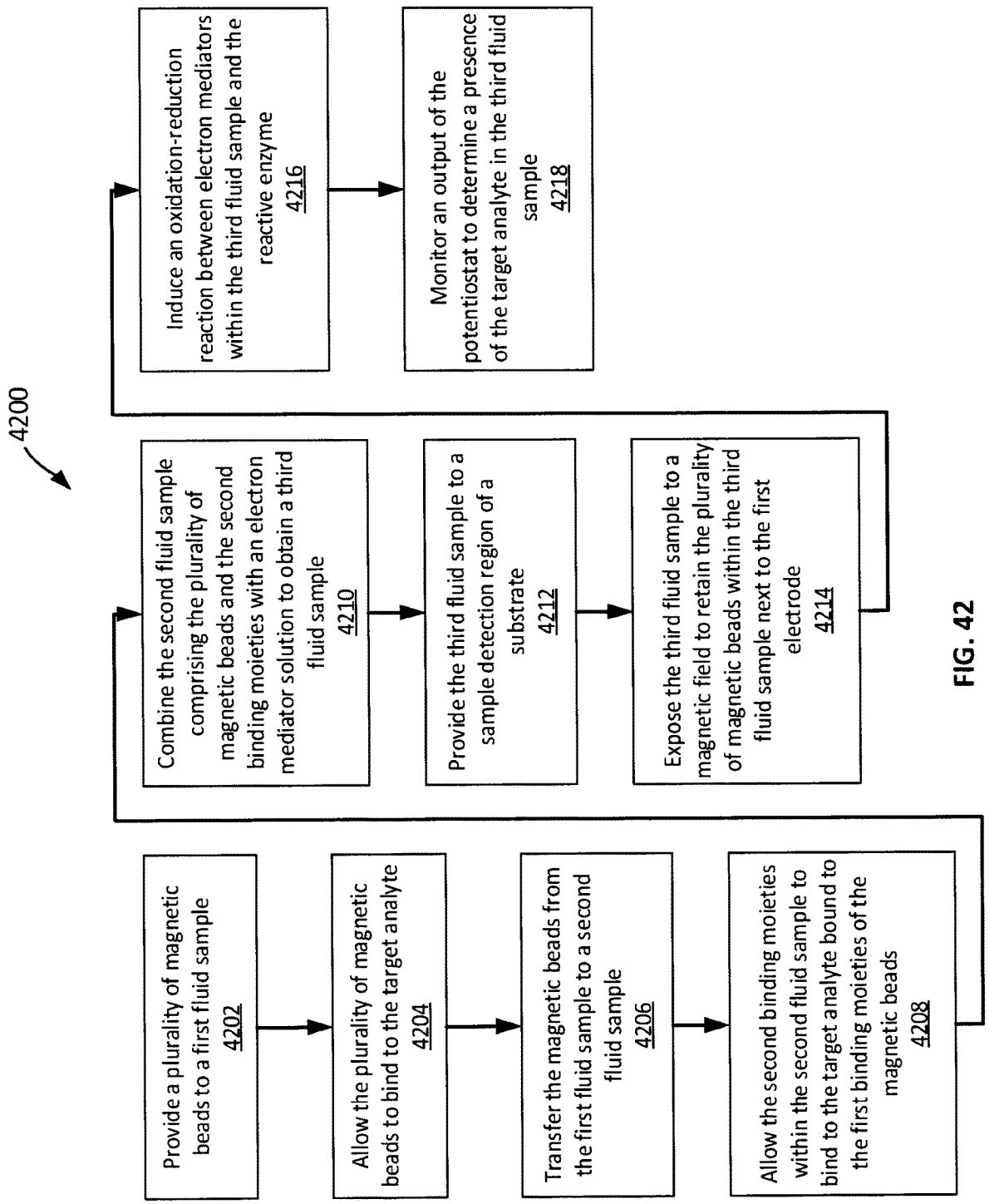
FIG. 42 is a flow chart diagram of an example of a process of detecting a presence of target analytes.

An example process 4200 of detecting a presence of a target analyte in a fluid sample is shown in FIG. 42.

In the process 4200, a plurality of magnetic beads is provided to a first fluid sample (4202). The plurality of magnetic beads includes first binding moieties specific for binding to the target analyte.

The plurality of magnetic beads are allowed to bind to the target analyte within the first fluid sample (4204).

The magnetic beads are transferred from the first fluid sample to a second fluid sample (4206). The second fluid sample include second binding moieties that are specific for binding to the target analyte, and the second binding moieties are bound to a reactive enzyme. Transferring the magnetic beads includes immersing a sheath within the first fluid sample, placing a magnet within the sheath that is immersed within the first fluid sample, such that the magnetic beads adhere to the sheath, removing the sheath containing the magnet from the first fluid sample, and immersing the sheath containing the magnet in the second fluid sample.

The second binding moieties within the second fluid sample are allowed to bind to the target analyte bound to the first binding moieities of the magnetic beads (4208).

The second fluid sample including the plurality of magnetic beads and the second binding moieties are combined with an electron mediator solution to obtain a third fluid sample (4210).

The third fluid sample is provided to a sample detection region of a substrate (4212). The sample detection region is arranged on a first electrode.

The third fluid sample is exposed to a magnetic field to retain the plurality of magnetic beads within the third fluid sample next to the first electrode (4214). The first electrode is electrically coupled to a potentiostat.

An oxidation-reduction reaction between electron mediators is induced within the third fluid sample and the reactive enzyme (4216).

An output of the potentiostat is monitored to determine a presence of the target analyte in the third fluid sample (4218). The output of the potentiostat is modified by the oxidation-reduction reaction.

The process 4200 can be performed, at least in part, using one or more of the devices and kits described herein. In some cases, the process 4200 can be performed to identify analyte such as cells, extracellular vesicles such as microvesicles, membrane particles, apoptotic blebs or vesicles or exosomes (e.g., transmembrane and cytosolic proteins, mRNA, DNA, and microRNA), peptides, proteins, lipids, metabolites, and other molecules, either free-floating (e.g., in a serum or a solution) or expressed on the surface of a biological structure (e.g., on the surface of an extracellular vesicle or a cell). In some cases, the process 4200 can be used to provide more effective care to a patient (e.g., by enabling caretakers to make diagnoses and/or administer treatment in a more informed manner). In some cases, the process 4200 can be performed to provide insight into the composition of the substance (e.g., a food product).

Examples of Applications of the New Detector Devices

The implementations described herein can be used in a variety of different applications, including the detection and quantification of various peptides, proteins, lipids metabolites, and other molecules, either free-floating (e.g., in a serum or a solution) or expressed on the surface of a biological structure (e.g., on the surface of an extracellular vesicle or a cell). In some cases, the detection and quantification of molecules can provide insight into a particular biological or pathogenic process, a particular progression of a particular disease, or some other biological condition.

Examples of various applications are discussed in more detail below and in the Examples section.

Extracellular Vesicle Screening—Cancer Diagnostics

As an example, magnetic electrochemical sensing can be used to detect the presence of biomarkers of cancer on extracellular vesicles.

Growing evidence has positioned extracellular vesicles (EVs) as an effective readout of cancer management. Exosomes, for example, have emerged as a potent biomarker. Exosomes are nanoscale vesicles actively secreted by cells. These vesicles carry molecular constituents of their originating cells, including transmembrane and cytosolic proteins, mRNA, DNA, and microRNA, and can thus serve as cellular surrogates. Combined with their relative abundance and ubiquitous presence in bodily fluids (e.g. serum, ascites, urine, CSF), exosomes can offer unique advantages for longitudinal monitoring. Exosome analyses are minimally invasive and afford relatively unbiased readouts of the entire tumor burden, less affected by the scarcity of the samples or intra-tumoral heterogeneity.

Electrochemical sensing can be an effective detection modality that is easily applicable to clinical settings. Electrochemical sensing could achieve high sensitivity through signal amplification with redox-active reporters. As described herein, a sensing system can measure electrical currents induced by the redox-active reporters, and can be realized as a compact and low-power portable device.

As described herein, implementations of the sensing system provide various benefits. For example, cell-specific exosomes can be isolated directly from complex media without need for extensive filtration or centrifugation. Further, the assay can achieve high detection sensitivity through magnetic enrichment and enzymatic amplification. Further still, through the electrical detection scheme, sensors can be miniaturized and expanded for parallel measurements.

As an example, ovarian cancer exosomes are often enriched with CD63. Thus, implementations of the sensing system can be used to profile CD63 expressing EV populations (e.g., exosomes) as a means of diagnosing ovarian cancer.

For instance, magnetic beads can be conjugated to antibodies specific against CD63. These magnetic beads can be mixed with a biological sample containing exosomes (e.g., plasma), such that exosomes expressing CD63 can be magnetically captured. In turn, the sample can be treated with secondary molecules specific to CD63 expressing exosomes (e.g., a labeling ligand, such as biotinylated antibodies specific against CD63), and treated with tertiary molecule specific to the secondary molecules and having an oxidizing enzyme (e.g., a streptavidin-HRP). The sample can then be combined with an electron mediator solution (e.g., a solution containing 3,3',5,5'-tetramethylbenzidine, TMB).

The sample can be subsequently analyzed using the sensing systems described herein. As the CD63 expressing exosomes have been captured by the magnetic beads, they are concentrated near the electrodes of the sensing system. Further, due to the potential induced across the electrodes (e.g., the working electrode and the reference electrode), an oxidation-reduction reaction is induced between the electron mediators and the oxidizing enzyme. As a result, a current is induced across one of the electrode (e.g., the counter electrode), correlating with the presence and prevalence of CD63 expressing exosomes. In turn, this current can be measured by an MCU or other computing device, and the resulting information can be used for investigative or diagnostic purposes. For example, a relatively high current can correspond to a relatively high concentration of CD63 expressing exosomes, and may be an indicator of ovarian cancer in a patient.

In some cases, the output of a potentiostat can be compared to a threshold or reference level, and the presence or absence of a cancer within a patient can be diagnosed based on the comparison. For example, if the output of a potentiostat is sufficiently high (e.g., a current that exceeds a reference or threshold level), a diagnosis regarding the presence of a cancer can be rendered. However, if the output of the potentiostat is relatively low (e.g., a current that does not exceed the reference or threshold level), a diagnosis regarding the absence of a cancer can be rendered. In some cases, an instrument can render a diagnosis automatically or semi-automatically based on the measurements.

Although the detection of exosomes expressing CD63 in blood is described above, this is merely an example. In practice, implementations of the sensing system can be used to detect any biomarker (e.g., biomarkers associated with different biological or pathogenic processes, diseases, or other biological conditions), either free-floating (e.g., free-floating in plasma, urine, or any other biological sample) or expressed on the surface of a biological structure (e.g., on the surface of an extracellular vesicle or a cell). As an example, in some implementations, the sensing system can be used to detect one or more of the following biomarkers: CD2, CD3, CD45, CD52, HLA-ABC, CD81, CXCL10, or CXCL9, or any other immune cell markers. As another example, in some implementations, the sensing system can be used to detect one or more of the following biomarkers: CD24, EpCAM, CA125, EGFR, HER2, MUC1, CD44, CD44v6, CEA, Mesothelin, Trop2, GPC1, WNT2, Grp94, SSTR2, EGFRv3, IDH1-R132, GPA33, KRAS, CD166, CD133, MET, B7H3, CD63, CD9, or CD81.

Extracellular Vesicle Screening—Organ Rejection Testing

As another example, magnetic electrochemical sensing can be used to detect transplanted organ rejection in a patient.

For instance, in patients experiencing transplanted kidney rejection, CD3 expressing EVs are often found in the patient's urine. Thus, implementations of the sensing system can be used to profile CD3 expressing EV populations (e.g., exosomes) as a means of detecting transplanted kidney rejection at the early stages of rejection.

For instance, magnetic beads can be conjugated to antibodies specific against CD3. These magnetic beads can be mixed with a biological sample containing exosomes (e.g., urine), such that exosomes expressing CD3 can be magnetically captured. In turn, the sample can be treated with secondary molecules specific to CD3 expressing exosomes (e.g., a labeling ligand, such as biotinylated antibodies specific against CD3), and treated with tertiary molecule specific to the secondary molecules and having an oxidizing enzyme (e.g., a streptavidin-HRP). The sample can then be combined with an electron mediator solution (e.g., a solution containing 3,3',5,5'-tetramethylbenzidine, TMB).

The sample can be subsequently analyzed using the sensing systems described herein, and the resulting information can be used for investigative or diagnostic purposes. For example, a relatively high current can correspond to a relatively high concentration of CD3 expressing exosomes, and may be an indicator of kidney rejection by a patient. In some cases, a patient can be regularly screened after a kidney transplant, such that a kidney rejection is quickly detected at an early stage. As the monitoring process is non-invasive, the monitoring process can be repeated with minimal risk to the patient and in a cost-effective manner.

In some cases, the output of a potentiostat can be compared to a threshold or reference level, and a determination regarding whether or not a patient has rejected an organ transplant can be diagnosed based on the comparison. For example, if the output of a potentiostat is sufficiently high (e.g., a current that exceeds a reference or threshold level), a determination that the patient has rejected the organ can be made. However, if the output of the potentiostat is relatively low (e.g., a current that does not exceed the reference or threshold level), a determination that the patient has not rejected the organ can be made. In some cases, an instrument can make a determination automatically or semi-automatically based on the measurements.

Although the detection of exosomes expressing CD3 in urine is described above, this is merely an illustrate example. As described herein, implementations of the sensing system can be used to detect any biomarker, either free-floating or expressed on the surface of a biological structure, to probe transplanted kidney rejection, or the rejection of other transplanted organs.

Food Testing

As another example, magnetic electrochemical sensing can be used to detect the presence of allergens in food products.

More than 50 million Americans have a food reaction of some kind. Further, even trace amounts of food antigens can trigger acute anaphylaxis, a potentially life-threatening hypersensitivity reaction requiring epinephrine injection. Although the results of immunotherapeutic trials have been encouraging, the primary approach continues to rely on food avoidance. The Food Allergen Labeling and Consumer Protection Act (FALCPA) mandates food labeling to inform customers about allergenic substances in products. Even so, mislabeling or cross-contamination in manufacturing continue to pose regulatory challenges. Furthermore, FALCPA only oversees packaged food, not food served in restaurants. Food labeling outside the US is less strict, and food allergies often affect travelers. Thus, the ability to rapidly test foods for common allergens could provide significant benefits to consumers.

As an example, consumers can be provided with an examination kit having a magnetic electrochemical sensing system and a sample preparation system, such as the kit described herein with respect to FIGS. 6-9. Consumers can use the kit to prepare a sample of a food product for examination, extract food antigens of interest from the sample (e.g., allergens that the user might be allergic to, such wheat, peanut, hazelnut, milk, and egg whites) using antigen-specific magnetic beads, and concentrate the antigens onto the electrodes of a sensing system. Consumers can then analyze the sample using the sensing system (e.g., using secondary molecules, tertiary molecules, and an electron mediating solution) to ascertain the presence and/or prevalence of the antigen in the food product, such that they can make more informed decisions regarding their diet.

In some cases, consumers can also be provided with a control application for a computing device (e.g., a smartphone) that enables the consumer to control the sensing system and/or review measurement information from the sensing system. For example, the control application can be used to customize the sensing application for a specific allergen (e.g., by calibrating measurements to a particular allergen and its corresponding sample preparation process). As another example, the control application can be used to record measurements for future review. As another example, the control application can be used to track the source of particular food products, such that a user can later visit a particular location again (e.g., to obtain food products that do not contain a particular allergen) or avoid a particular location in the future (e.g., to avoid obtaining food products that contain a particular allergen).

In some cases, the output of a potentiostat can be compared to a threshold or reference level, and a determination regarding whether a particular allergen is present in a food product based on the comparison. For example, if the output of a potentiostat is sufficiently high (e.g., a current that exceeds a reference or threshold level), a determination that the food product contains a particular allergen (e.g., to a sufficient degree to cause or potentially cause allergic reactions) can be made. However, if the output of the potentiostat is relatively low (e.g., a current that does not exceed the reference or threshold level), a determination that the food product do not contain a particular allergen (e.g., to a degree that does not cause or is unlikely to cause allergic reactions) can be made. In some cases, an instrument can make a determination automatically or semi-automatically based on the measurements.

Although example allergens are described above, these are merely illustrative examples. In practice, implementations of the sensing system can be used to detect any allergen using appropriate allergen-specific magnetic beads.

EXAMPLES

The invention is further described in the following examples, which do not limit the scope of the invention described in the claims.

Example 1—Cancer Diagnostics

The purpose of this example was to demonstrate the use of magnetic electrochemical sensing to screen exosomes for biomarkers correlated with the progression of ovarian cancer, such as CD63.

Device Summary

Figure 11:
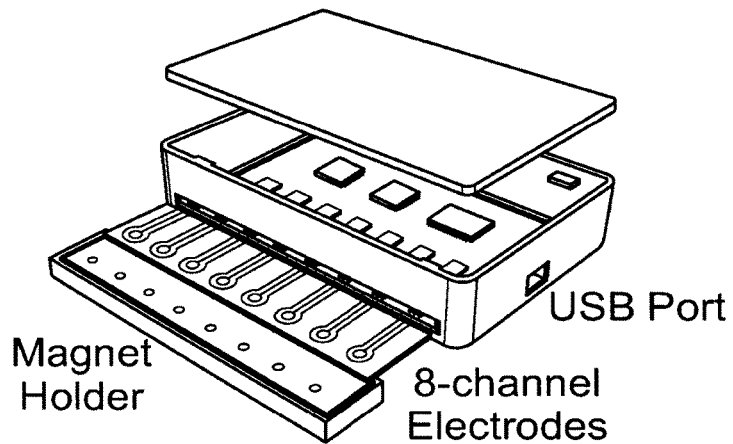
FIG. 11 is a diagram of an example of a miniaturized magnetic electrochemical sensing system (integrated magnetic-electrochemical exosome system, iMEX).

A miniaturized magnetic electrochemical sensing system (integrated magnetic-electrochemical exosome system, referred to herein as "iMEX"), was constructed having eight independent channels (see FIG. 11). Each channel was equipped with a potentiostat capable of measuring a wide range of current ($\pm 7.5$ µA). The sensor can simultaneously measure signals from eight electrodes. Small cylindrical magnets were located below the electrodes to concentrate immunomagnetically captured exosomes.

Figure 12A:
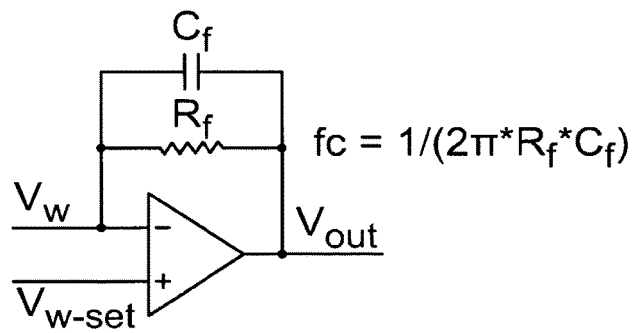
FIG. 12A is a schematic diagram of an example of a low-pass filter.
Figure 12B:
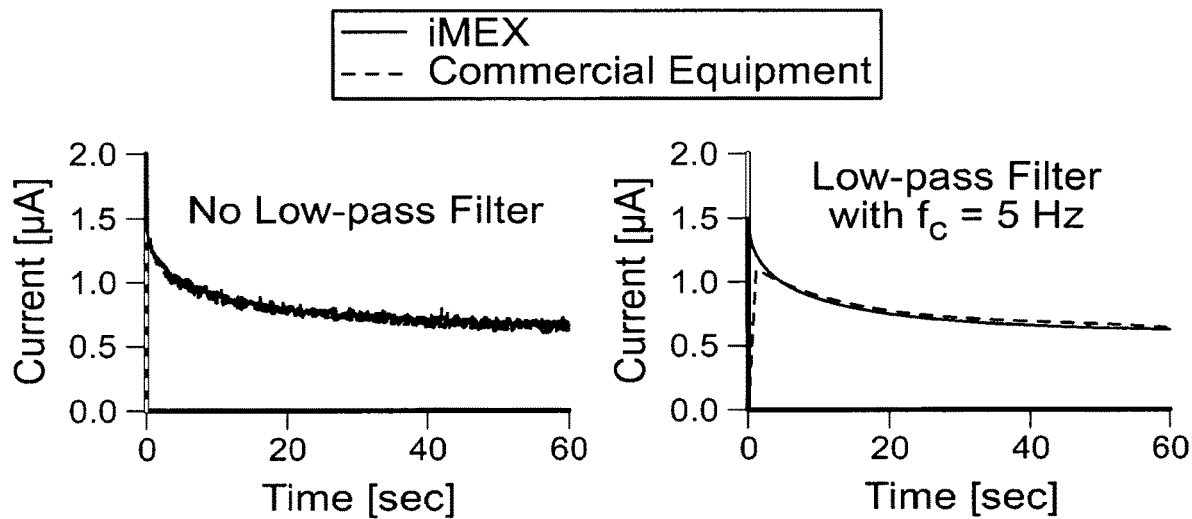
FIG. 12B shows a comparison of the measurement results between the iMEX sensor and a commercial system (SP200, Bio-Logic).

The input signal was conditioned by a low-pass filter (cut-off frequency, 5 Hz) to suppress high frequency noise. The circuit schematic of the low-pass filter embedded in each potentiostat. Vw-set was connected to the digital-to-analog converter for potential control, Vw was connected to a working electrode, and Vout was connected to the analog-to-digital converter for signal digitization (see FIG. 12A). The cut-off frequency of the low-pass filter was set to 5 Hz (Rf=300 k$\Omega$, Cf=0.1 µF). A comparison of the measurement results between the iMEX sensor and a commercial equipment (SP200, Bio-Logic) is shown in FIG. 12B. The potential of 200 mV (versus Ag/AgCl reference electrode) was applied in the solution of 0.2 mM ferrocyanide (in 0.1 M KCl). The current levels measured with the iMEX sensor and the commercial equipment showed a good match. With the low-pass filter, the noise levels decreased significantly.

Figure 13A:
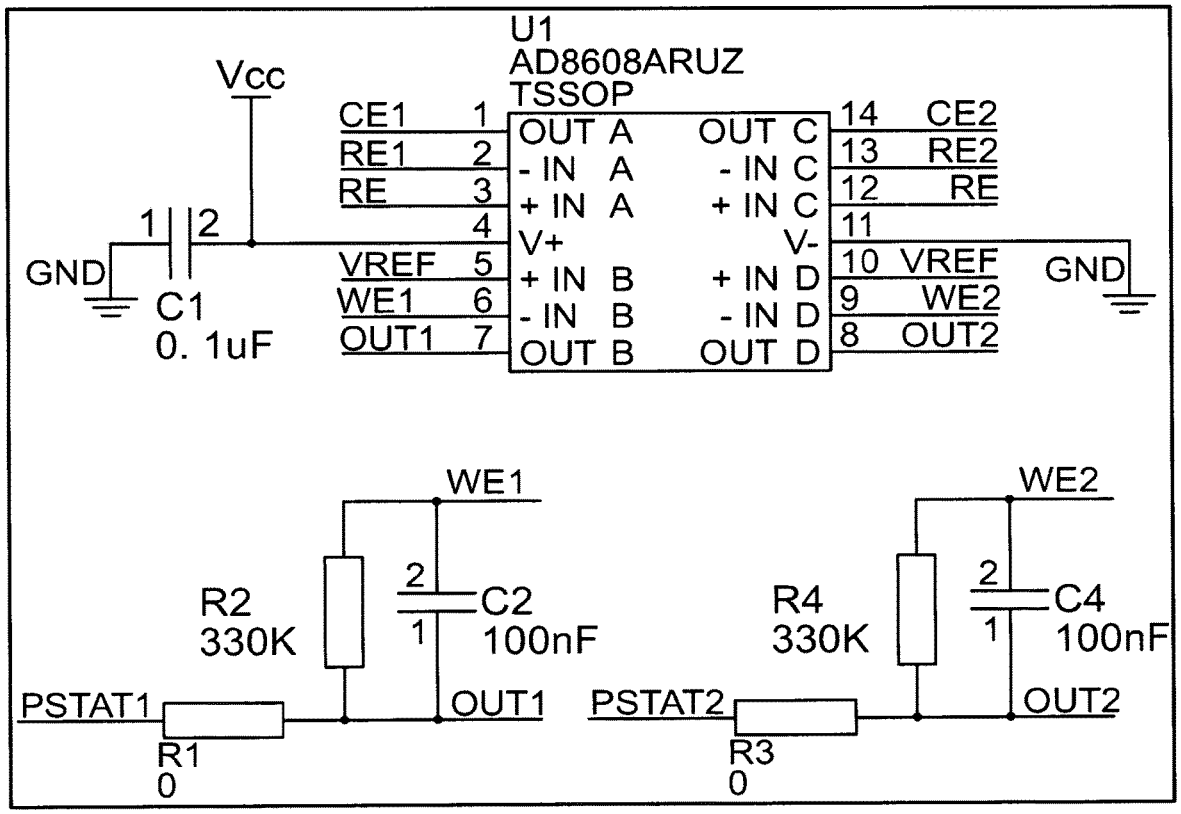
FIGS. 13A-13D are circuit diagrams of the iMEX system.
Figure 13B:
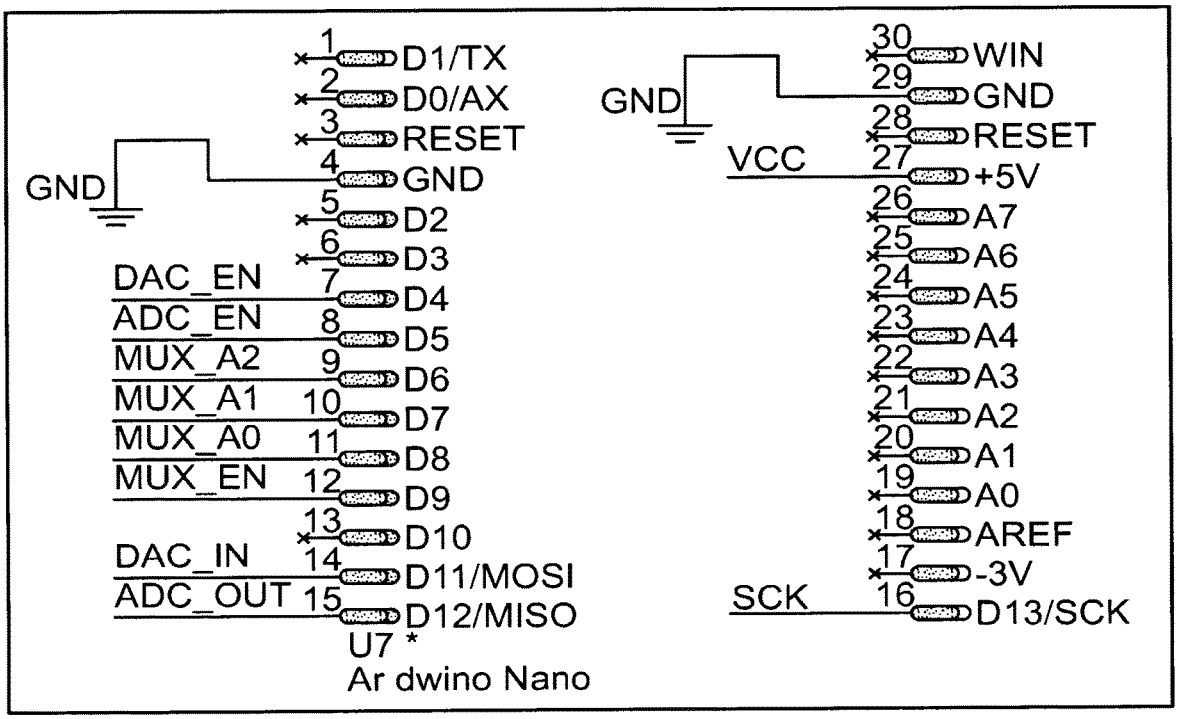
Figure 13C:
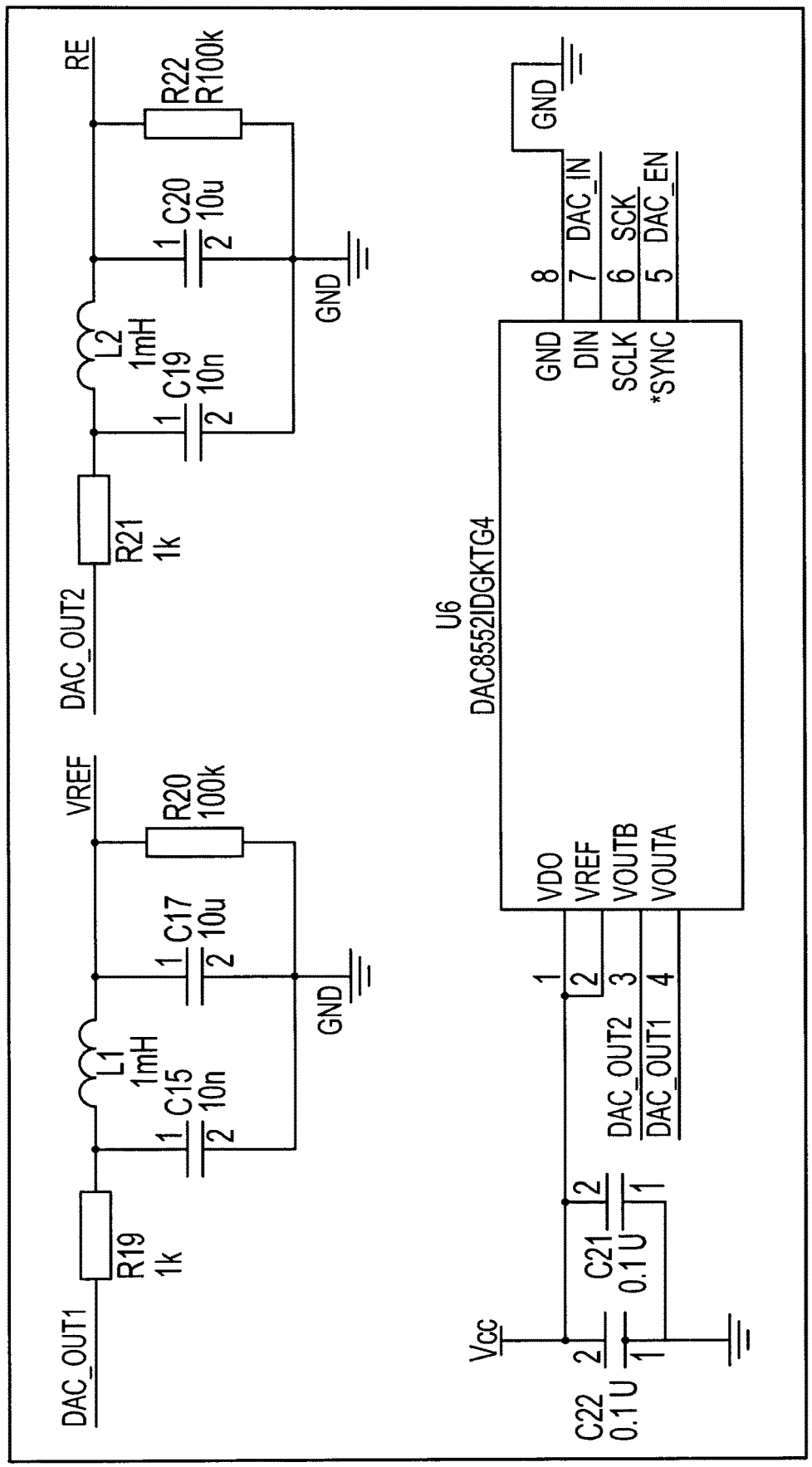
Figure 13D:
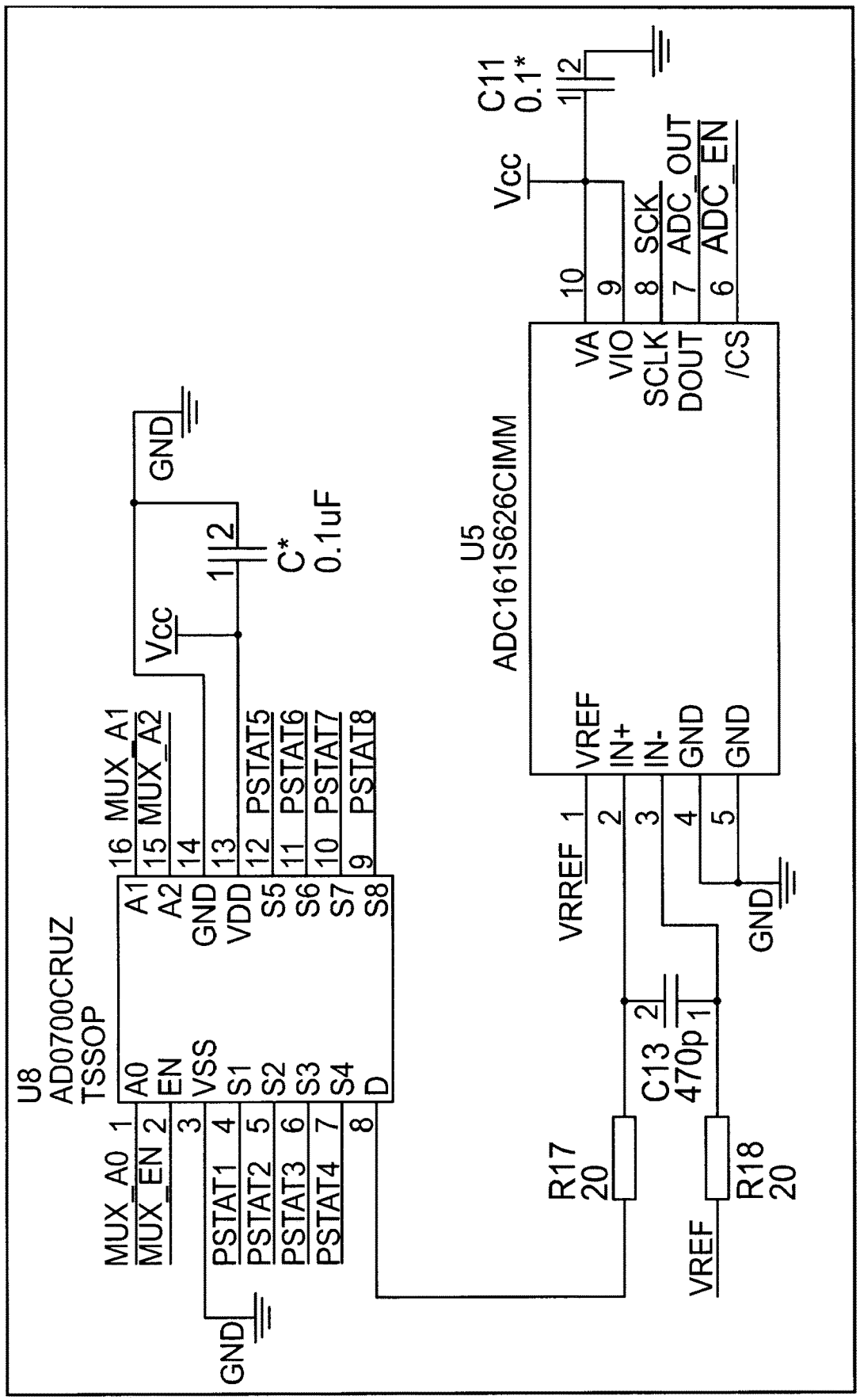

The eight potentiostats were connected to a digital-to-analog converter for potential control, an analog-to-digital converter for signal digitization, a multiplexer for channel selection, and a micro-controller unit for system operation (see FIGS. 4C and 13A-D). The sensor system had eight potentiostats, an 8-to-1 multiplexer, an analog-to-digital converter (ADC), a digital-to-analog converter (DAC), and a micro-controller unit (MCU). Each potentiostat had three electrodes: reference (R), counter (C), and working (W). As shown in FIG. 13B, the system included two potentiostats (AD8608, Analog Devices). The parallel circuit of R2 and C2 (or R4 and C4) formed a transimpedance amplifier with a low-pass filter with a cut-off frequency, 5 Hz. As shown in FIG. 13C, a microcontroller unit (Arduino Nano, Arduino) was used for the serial communication with external devices over USB. As shown in FIG. 13D, the system also included digital-toanalog converter unit (DAC8552, Texas Instruments). One output was connected to the analogto-digital converter unit (DAC_OUT1), and the other was connected to all the potentiostats (DAC_OUT2). Each output port was connected to a low-pass filter (L1, C15, C17, R20 for DAC_OUT1, and L2, C19, C20, R22 for DAC_OUT2) to minimize the noise. As shown in FIG. 13E, the sytem also included a 8-channel multiplexer (ADG708, Analog Devices) and analog-to-digital converter unit (ADC161S626, Texas Instruments). The multiplexer was controlled through its three address ports (MUX_A0-MUX_A2) by the micro-controller unit.

Figure 14:
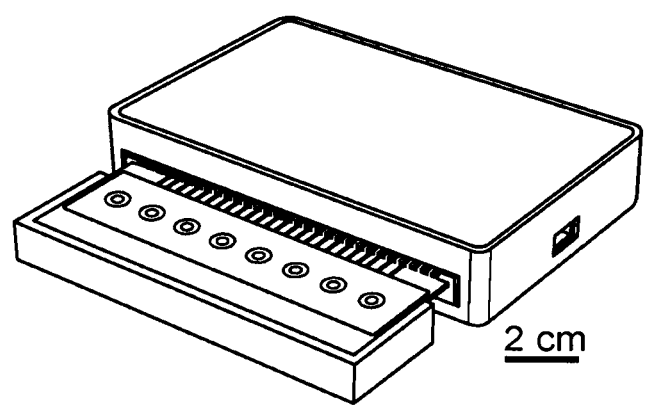
FIG. 14 is a diagram the packaged iMEX system.

As shown in FIG. 14, we packaged the device as a handheld unit. The device had a small form factor ($9\times6\times2$ cm$^3$). A card-edge connector was used for the quick attachment of the electrode cartridge. A magnet holder, containing 8 cylindrical magnets, was placed underneath the electrode cartridge. These magnets were used to concentrate magnetic beads to the sensor surface. The iMEX effectively provided a simultaneous readout from all electrodes through rapid polling of each channel (50 msec per channel).

Figure 15:
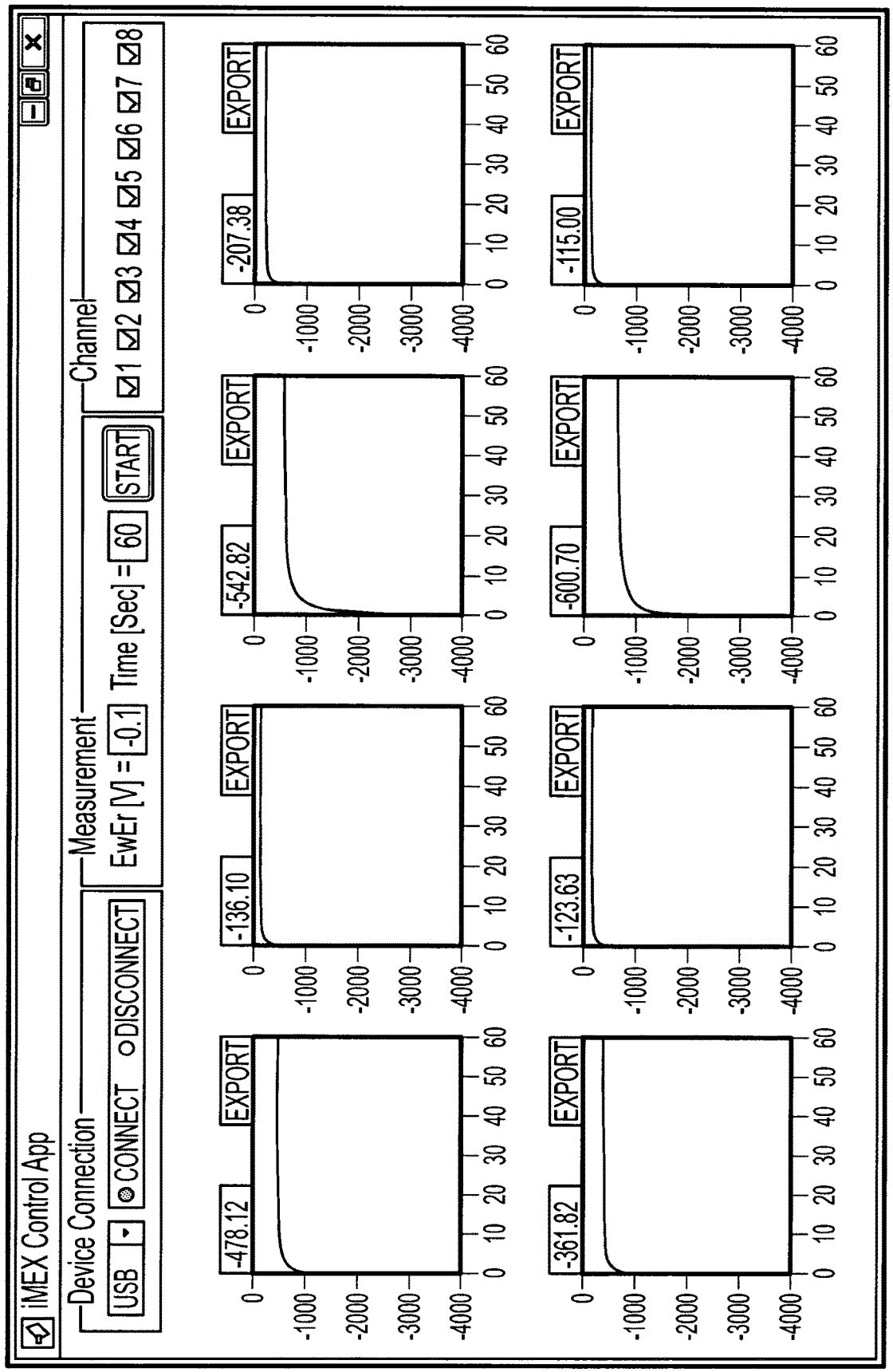
FIG. 15 is a diagram of an example graphical user interface for customized software to interact with the iMEX system.

All data were monitored and analyzed by custom-designed software. The iMEX sensor was controlled via a computer through an USB interface. The currents generated from electrochemical reactions were monitored on the selected channels. After 60 seconds, the averaged level of the currents over the range of 40-45 seconds was displayed (see FIG. 15).

Assay Scheme

Figure 16:
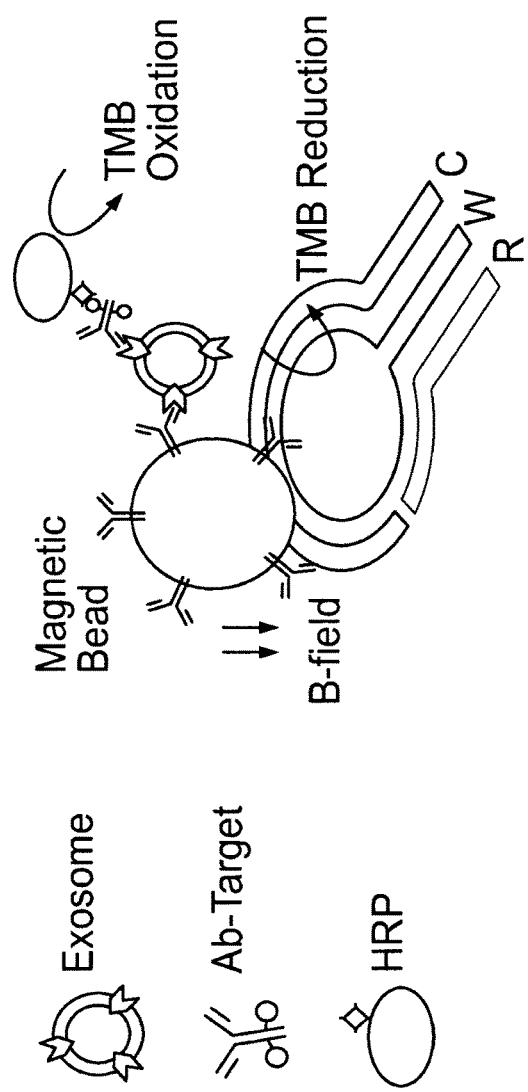
FIG. 16 is a schematic diagram of an iMEX assay.
Figure 17:
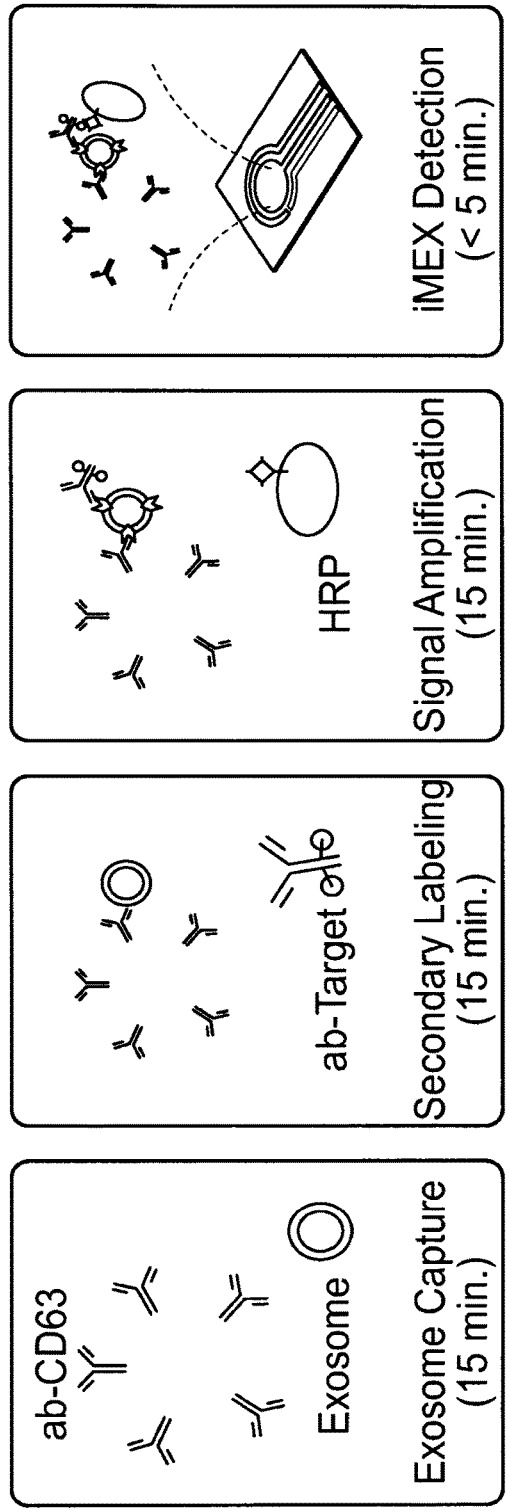
FIG. 17 is another schematic diagram of an iMEX assay.

FIG. 16 summarizes the iMEX assay scheme. Exosomes were first captured onto immunomagnetic beads. Secondary antibodies with an oxidizing enzyme (horseradish peroxidase; HRP) were then used, followed by mixing the beads with chromogenic electron-mediators (3,3',5,5'-tetramethylbenzidine; TMB) which generated electrical current when HRP is encountered. The assay scheme is shown in greater detail in FIG. 17. Magnetic beads conjugated with antibodies against CD63 were loaded in bodily fluids (or PBS) for exosome separation. Captured exosomes were labeled with antibodies against target protein markers (e.g. EpCAM or HER2). The antibodies were conjugated with biotin. HRP enzymes conjugated with streptavidin were mixed with the beads. Each step was followed by a one-minute magnetic washing step. The total assay was conducted within 1 hour at room temperature.

Using magnetic beads significantly simplified the assay procedures: excess agents (e.g. antibodies, enzymes) were removed via magnetic washing, and captured exosomes were magnetically concentrated on the electrodes to improve the detection sensitivity.

We applied the chronoamperometry method for signal detection: the electrical current generated from TMB reduction was monitored while a reduction potential (−100 mV versus Ag/AgCl reference electrode) was applied to a working electrode. The current level (I) reached a plateau within 1 minute after the reduction potential was applied (see FIG. 18). The current difference between the CD63-bead and IgG-bead samples ($\Delta I_M$) was used as a representative value of a target protein marker. Abs, antibodies. M, marker. We averaged the current level (I) from 40 to 45 seconds as a representative value.

To capture exosomes, we used magnetic beads that were coated with antibodies against tetraspanin, transmembrane proteins enriched in exosomes. We first compared signal levels with differently sized beads (diameters, 2.7 µm and 8.8 µm). When the total surface area of beads was matched to capture similar amount of exosomes, the measured signal levels were nearly identical (see FIG. 19A). iMEX assays were conducted with magnetic beads of different sizes (2.7 and 8.8 µm in diameter). The bead concentrations were $6 \times 10^{7/mL}$ and $6 \times 10^6$/mL, respectively, to provide the same capturing area. Exosomes were collected from OV90 cell culture and diluted in PBS with a concentration of $8 \times 10^8$/mL. This result can be explained with diffusivity in porous media: The effective diffusivity ($D_e$) for stacked beads can be expressed as $D_e = D_0 \cdot \varepsilon^m$, where $D_0$ is the diffusivity in free media, and E is the porosity of the structure. In case of uniformly sized beads, both $\varepsilon (\leq 0.47)$ and m ($=3/2$) are bead-size independent; the iMEX signals are thus expected to remain constant. We opted to use 2.7-µm beads; bigger beads tended to sediment, requiring frequent shaking of samples. Compared to the no-enrichment scheme, magnetic enrichment led to ~72% increase in the analytical signal (see FIG. 19B). iMEX assays were conducted with and without magnetic enrichment. For the magnetic enrichment, a small coinshaped permanent magnet was placed at the back of a working electrode. All measurements were performed in duplicate, and the data are displayed as mean±standard deviation (SD).

We next tested three representative tetraspanin proteins (CD63, CD9, CD81) as a target; these markers are reportedly enriched in exosomes. We prepared 2.7-µm magnetic beads specific to each marker. When applied to exosomes from different cell lines, CD63-based capture showed consistently high signal. FIG. 20 shows a signal comparison of three tetraspanin markers (CD63, CD9, and CD81) in cancer exosomes. Signals from CD63 were much higher than those from other markers in exosomes collected from ovarian cancer cell lines (CaOV3, OV90, and OVCAR3). We thus opted to use CD63 as a marker for exosome enrichment.

For each target marker (M), we prepared a pair of magnetic beads: one conjugated with antibodies against CD63 (CD63-beads) and the other with antibodies against iso-type matched IgG (IgG-beads). Exosomes were mixed with each bead-type and subsequently labeled with antibodies against a target marker; the net signal difference $\Delta I_M$ ($=I_{CD63+M} - I_{IgG+M}$; see FIG. 18) was then obtained. We used $\Delta I_{CD63}$ to estimate the total exosome load, and defined a normalized metric $\tau_M$ ($=\Delta I_M/\Delta I_{CD63}$) as the expression level of a target marker (M). Note that such scaling would compensate for variations in exosome numbers among samples.

iMEX Validation

Figure 21:
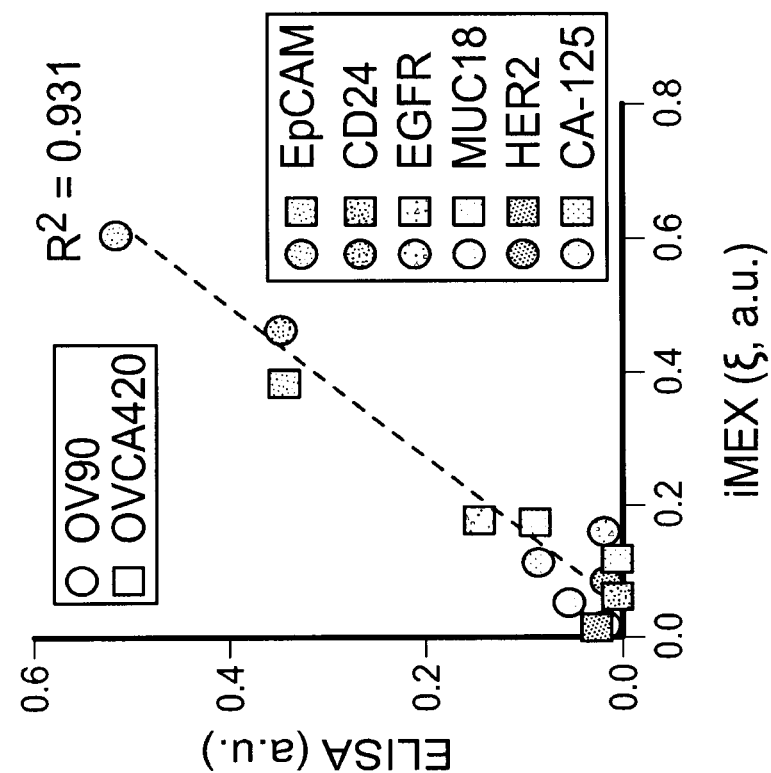
FIG. 21 shows a comparison between iMEX and ELISA. Six surface proteins were profiled in two ovarian cancer cell lines (OV90 and OVCA420).

We applied the developed iMEX protocol to profile exosomes for transmembrane proteins. For this validation study, we harvested exosomes from cell culture (OV90, OVCA420) through a conventional method, and spiked them into phosphate buffered saline (PBS) solution (~$10^9$ exosomes/mL). Samples were aliquoted, and processed by iMEX and enzyme-linked immunosorbent assays (ELISA). Comparative analysis showed high correlation between two methods (see FIG. 21; $R^2 = 0.931$), confirming iMEX's analytical capacity. The iMEX assay, however, was faster (1 hr) and consumed smaller amounts of samples (10 µL) than ELISA (5 hr, 100 µL).

Figure 22:
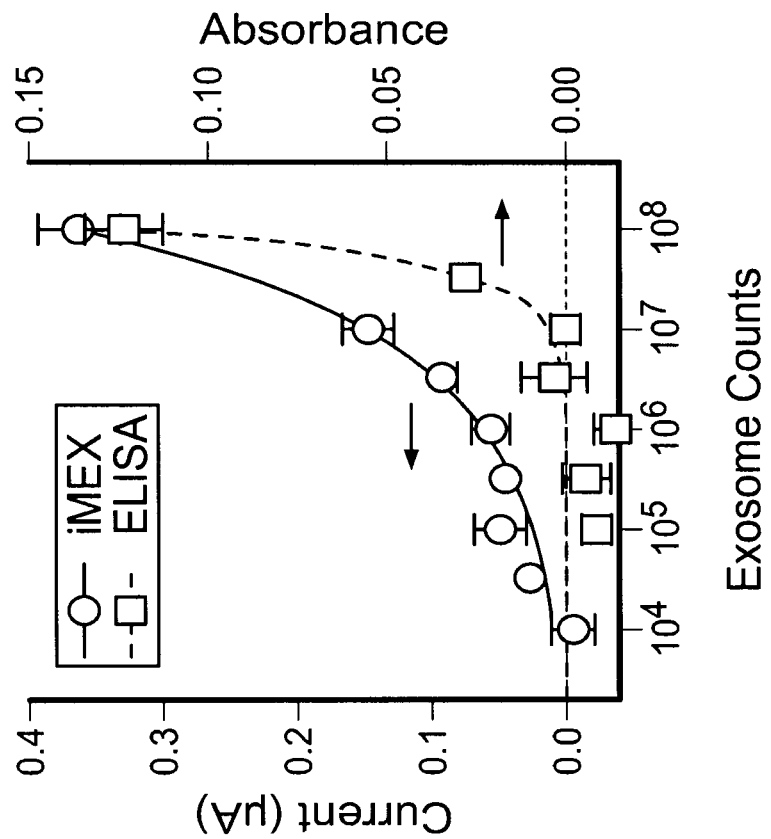
FIG. 22 shows a comparison between iMEX and ELISA assays when varying numbers of extracellular vesicles were spiked into human plasma.

We further tested iMEX for detecting exosomes in biofluids. Cancer exosomes were collected from cell culture (OV90), and varying numbers of exosomes were spiked into undiluted human plasma. Titration experiments established the limit of detection (LOD) of $3 \times 10^4$ exosomes, with the dynamic ranges spanning four orders of magnitude (see FIG. 22). Similar measurements with ELISA required more than $10^7$ exosomes for reliable detection. Using matched controls (IgG-beads) was important to compensate for background signals from sample-dependent, non-specific exosome binding. The detection limits were $3 \times 10^4$ (iMEX) and $3 \times 10^7$ (ELISA). All measurements were performed in triplicate, and the data are displayed as mean±SD.

Profiling of Protein Markers in Cell Derived Exosomes

Figure 23:
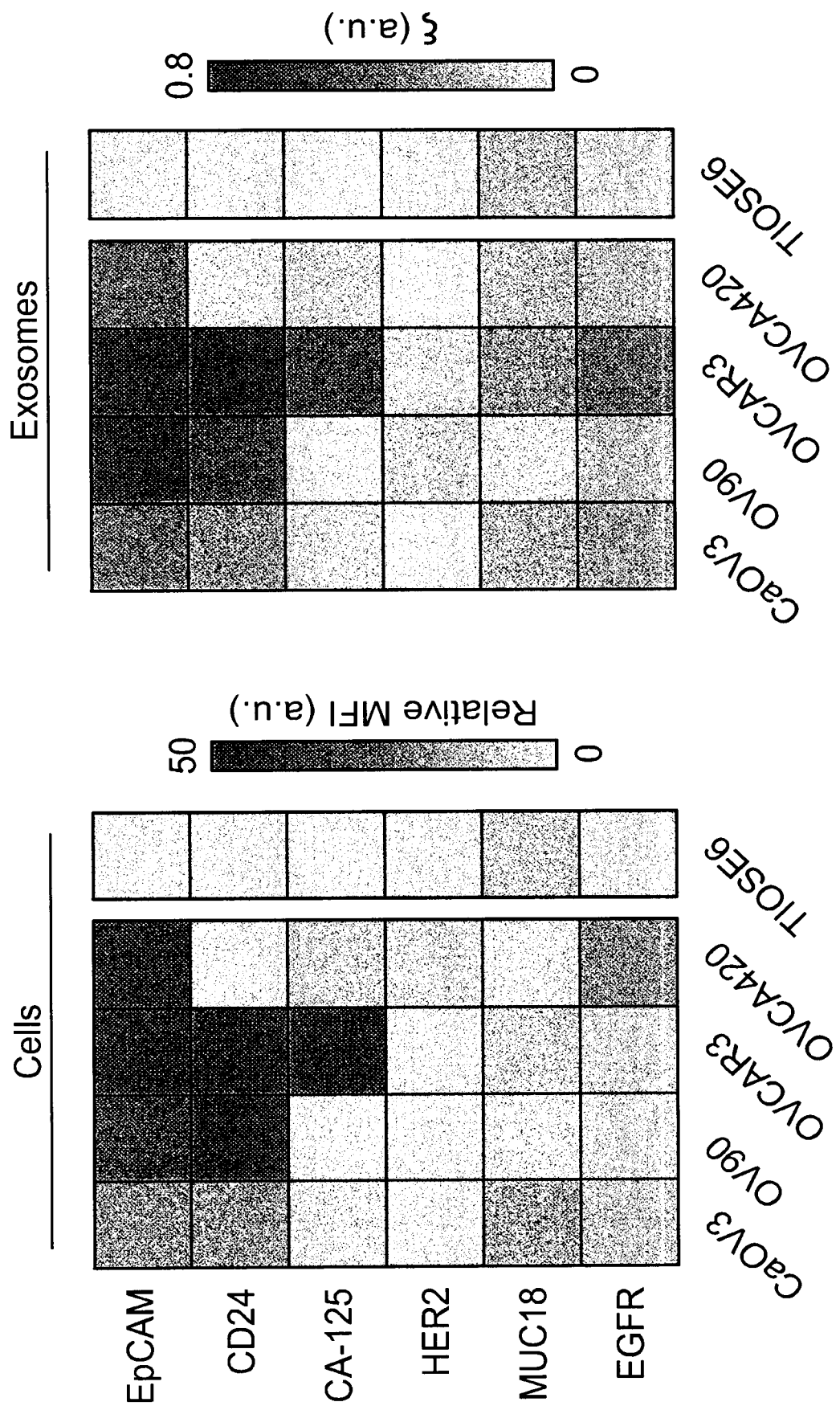
FIG. 23 shows the profiling of surface proteins in ovarian cancer cells and their secreting extracellular vesicles.

We applied the iMEX to screen exosomal surface markers from a panel of ovarian cancer cell lines. Because iMEX enriches CD63-positive (CD63+) exosomes and labels them for target proteins, we were able to examine how closely CD63+ exosomes reflect their cells of origin. We chose six representative surface markers based on prior studies: epithelial cell adhesion molecule (EpCAM), CD24, cancer antigen 125 (CA125), human epidermal growth factor 2 (HER2), mucin 18 (MUC18), and epidermal growth factor receptor 2 (EGFR). The cellular expression levels of these markers were measured with flow cytometry; exosomes were harvested from the conditioned cell-culture media, and profiled with iMEX. The molecular profiles of cells and CD63+ exosomes were highly correlated (see FIG. 23, showing mean fluorescence intensities (MFI), with darker regions indicate higher MFI and lighter regions indicating lower MFI), which supported the use of exosomes as cellular surrogates. Four ovarian cancer cell lines (CaOV3, OV90, OVCAR3, and OVCA420) and one normal cell line (TIOSE6) were screened for six putative cancer markers (via flow cytometry, FIG. 23, left panel). Cell-derived exosomes were immunomagnetically captured (CD63-specific) and assayed by iMEX (FIG. 23, right panel). The profiling data showed a good match between cells and CD63-positive exosomes. The iMEX assay was in duplicate, and the mean values are displayed.

Clinical: Direct Analyses of Plasma from Patients with Ovarian Cancer

Figure 24:
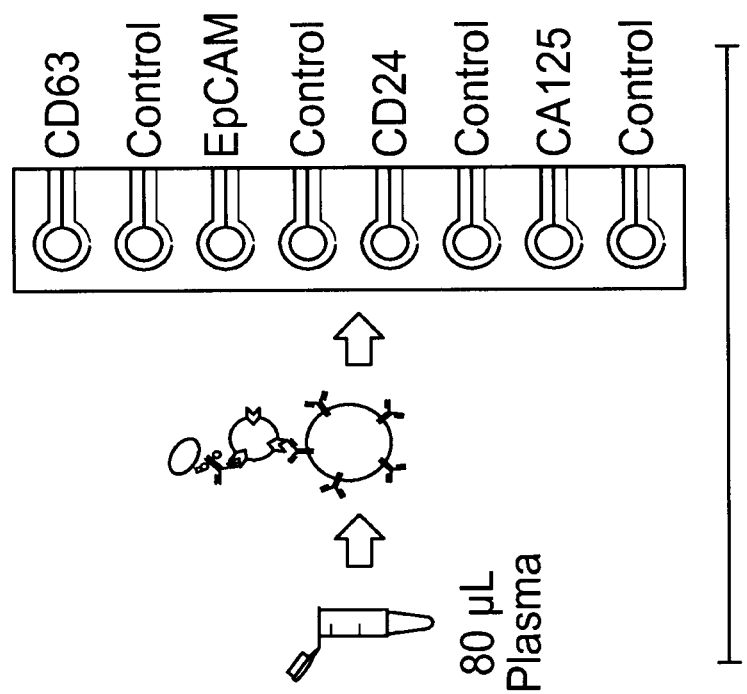
FIG. 24 shows an iMEX assay for clinical sample analysis.

The iMEX assay isolates EVs directly from plasma or serum, and allows profiling in a rapid, high-throughput manner—key for successful integration into the clinical workflow. To demonstrate clinical feasibility, we customized the iMEX assay for ovarian cancer EV detection in blood (see FIG. 24). Clinical plasma samples were aliquoted without any purification, and each aliquot (10 µL per marker) was incubated with magnetic beads for EV capture (15 min), followed by magnetic washing. The bead-bound EVs were consecutively labeled for target markers (15 min) and HRP (15 min), and loaded onto the device. With the 8-electrodes independently operated, we were able to simultaneously measure four different markers (CD63, EpCAM, CD24, and CA125) along with their respective IgG-controls. The IgG-controls were beneficial to specific detection of target molecules among non-purified clinical samples. The entire assay was completed within 1 hour without filtration and centrifugation processes.

Figure 25:
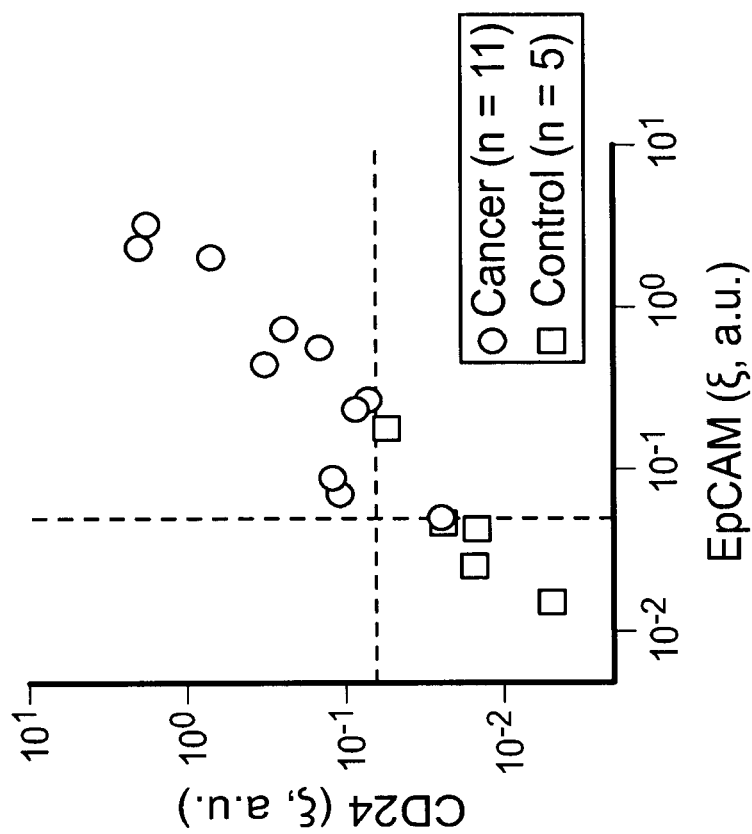
FIG. 25 shows an analysis of plasma samples from ovarian cancer patients (n=11) and healthy controls (n=5) obtained using an iMEX assay.
Figure 27:
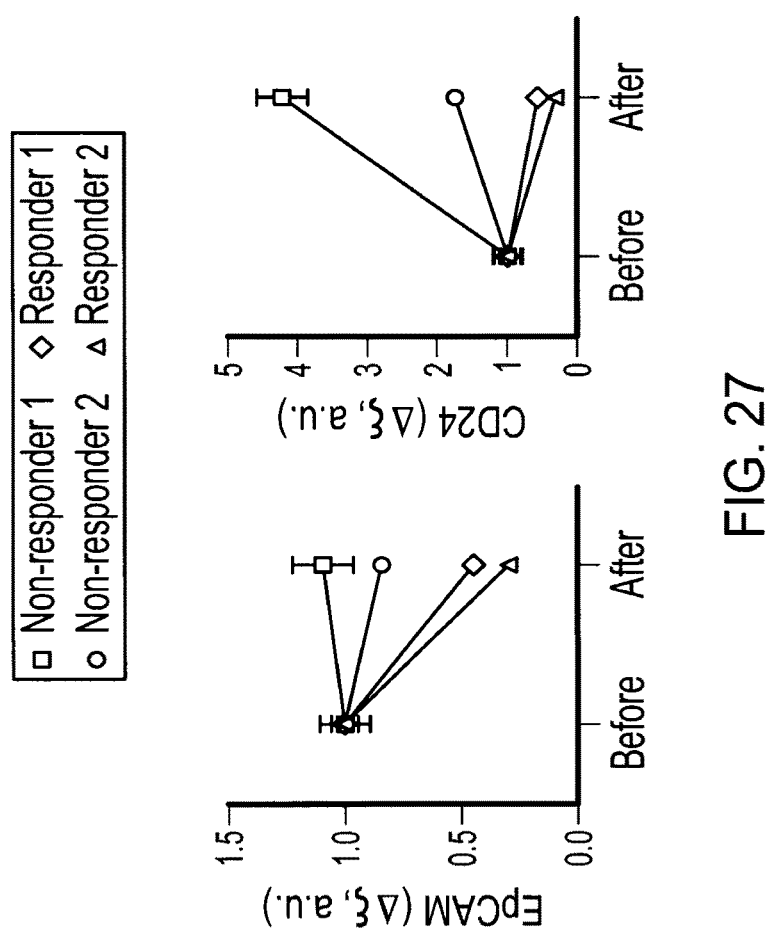
FIG. 27 shows longitudinal monitoring of drug treatment responses using an iMEX assay.
Figure 26:
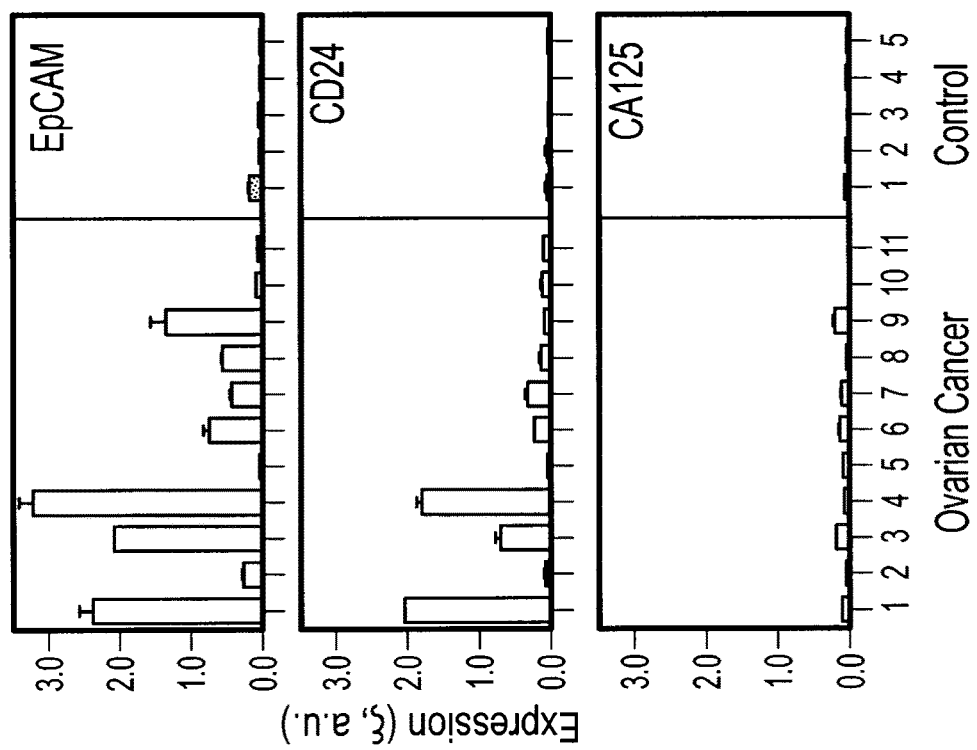
FIG. 26 shows EpCAM, CD24, and CA125 levels in plasma samples from ovarian cancer patients obtained using an iMEX assay.

We tested single-time point plasma samples from 11 ovarian cancer patients and five healthy controls. The expression levels of EpCAM and CD24 in EVs were much higher in ovarian cancer patients than healthy controls, and both metrics showed high correlation ($R^2=0.870$) (see FIGS. 25 and 26). We next examined iMEX's potential for serial EV testing by measuring EpCAM and CD24 in plasma collected at two time points (2 months apart) from four ovarian cancer patients undergoing drug treatment. The iMEX assays were conducted blinded to treatment response. For "non-responding" patients, expression levels of EpCAM and CD24 increased while "responding" patients displayed a significant decrease in both markers (see FIG. 27). The level of CD24 showed steeper increases than that of EpCAM for non-responders. All measurements were in duplicate. a.u., arbitrary unit.

Fabrication of the iMEX System

The device included of a micro-controller (Atmega328, Atmel Corporation), a digital-to-analog converter (DAC8552, Texas Instruments), an analog-to-digital converter (ADC161S626, Texas Instruments), a multiplexer (ADG708, Analog Devices), and eight potentiostats. Each potentiostat included of two operational amplifiers (AD8606, Analog Devices): one amplifier maintains the potential difference between a working electrode and a reference electrode, and the other one works as a transimpedance amplifier to convert a current to a voltage signal. The current measuring range of the transimpedance amplifier was ±7.5 µA. The eight-channel electrodes are commercially available (DropSens, Spain).

Preparation of Immunomagnetic Beads 5 mg of magnetic beads coated with epoxy groups (Dynabeads M-270 Epoxy, Invitrogen) were suspended in 1 mL of 0.1M sodium phosphate solution at room temperature for 10 minutes. The magnetic beads were separated from the solution with a permanent magnet and re-suspended in 100 µL of the same solution. 100 µg of antibodies against CD63 (Ancell) or respective IgG (Ancell) were added and mixed thoroughly. 100 µL of 3M ammonium sulfate solution was added, and the whole mixture was incubated overnight at 4° C. with slow tilt rotation. The beads were washed twice with phosphate buffer saline (PBS) solution and finally re-suspended in 2 mL of PBS with 1% bovine serum albumin (BSA). More details can be found in the manual provided by the manufacturer of the magnetic beads.

Biotinylation of Labeling Antibodies 10 mM Sulfo-NHS-Biotin (Pierce) solution in PBS was incubated with antibodies for two hours at room temperature. Unreacted Sulfo-NHS-Biotin was removed using Zeba spin desalting column, 7K MWCO (Thermo Scientific). Antibodies were kept at 4° C. until use.

iMEX Assay

10 µL of exosomes-spiked PBS solution (or plasma) was mixed with 50 µL of the immunomagnetic bead solution for 15 minutes at room temperature. The bead concentration was determined according to the following criterion: $[C_b \times V_b \times 4\pi R_b^2]/[C_e \times V_e \times \pi Re^2] > 100$, where $C_b$ and $C_e$ are the bead and the exosome concentrations, respectively; $V_b$ and $V_e$ are the volume of the bead solution and the exosome-spiked solution (or plasma), respectively; $R_b$ and $R_e$ are the mean radius of beads and exosomes, respectively. This requirement ensured that sufficient bead surface was available for exosome capture. In our experiment condition, $R_e \sim 50$ nm, $R_b = 1.4$ µm, and $C_e \sim 10^{10}$/mL. Therefore, we adjusted the bead concentration to $\sim 10^8$/mL. The magnetic beads were separated from the solution with a permanent magnet and re-suspended in 80 µL of PBS (1% BSA). After 5 seconds of vortexing, the beads were separated and re-suspended in 80 µL of PBS (1% BSA). 10 µL of antibodies of interest (20 µg/mL in PBS) were mixed with the beads for 15 minutes at room temperature. The magnetic beads were separated and washed as described before, and they were re-suspended in 50 µL of PBS (1% BSA). 5 µL of streptavidin-conjugated HRP enzymes (1:100 diluted in PBS) were mixed with the beads for 15 minutes at room temperature. The magnetic beads were separated and washed as described before, and they were re-suspended in 7 µL of PBS. The prepared bead solution and 20 µL of UltraTMB solution (ThermoFisher Scientific) were loaded on top of the screen-printed electrode. After 3 minutes, chronoamperometry measurement was started with the electrochemical sensor. The current levels in the range of 40-45 seconds were averaged.

Enzyme-Linked Immunosorbent Assay (ELISA)

CD63 antibody (Ancell) and IgG1 antibody (Ancell) were dilute to 5 µg/mL concentration in PBS and added to the Maxisorp 96 well plate (Nunc) for overnight incubation at 4° C. After washing with PBS, 2% BSA in PBS blocking solution was added to the plate for 1 hour incubation at room temperature. Subsequently, $10^8$ exosomes in 100 µL PBS were added to each well for 1 hour incubation at room temperature. After discarding the blocking solution, antibodies (1 µg/mL) against various markers were added to each well and incubated at room temperature for 1 hour. Unbounded antibodies were washed with PBS three times. Streptavidin-HRP molecules were added to the each well for 1 hour at room temperature. After washout with PBS, the chemiluminescence signal was measured.

Flow Cytometry $5 \times 10^5$ cells per antibody were used for flow cytometry experiments. Cells were fixed with 4% paraformaldehyde for 10 minutes at room temperature, and then washed with PBS (0.5% BSA). Subsequently, cells were blocked with BSA (0.5% in PBS) and then incubated with primary antibodies (4 µg/mL). After primary antibody incubation, cells were washed, incubated with fluorophore conjugated secondary antibody (2 µg/mL; Abcam) and washed. The fluorescence signals from the labeled cells were measured using BD LSRII Flow Cytometer (BD Biosciences). Mean fluorescent intensities (MFIs) recorded were normalized using the following formula [(signal-IgG isotype control)/secondary]. Blocking and incubation with antibodies (primary and secondary) were preformed for 30 min each at room temperature. Every washing step included three 5-min washes at 300 g with PBS (0.5% BSA).

Cell Culture

OV90, OVCAR3, OCVA420, and TIOSE6 cells were grown in RPMI-1640 medium (Cellgro). CaOV3 were cultured in Dulbecco's modified essential medium (DMEM, Cellgro). All media were supplemented with 10% FBS and penicillin-streptomycin (Cellgro). All cell lines were tested and were free of mycoplasma contamination (MycoAlert Mycoplasma Detection Kit, Lonza, LT07-418).

Exosome Isolation from Cultured Cells

We used a conventional method to harvest exosomes from cell culture media. Cells at passages 1-15 were cultured in vesicle-depleted medium (with 5% depleted FBS) for 48 hours. Conditioned medium from ~$10^7$ cells was collected, centrifuged at 300 g for five minutes. Supernatant was filtered through a 0.2-μm membrane filter (Millipore) and concentrated by 100,000 g for one hour. After the supernatant was removed, exosome pellet was washed with PBS and centrifuged at 100,000 g for 1 hour. Exosome pellet was resuspended in PBS.

Clinicl Sample Preparation The study was approved by the Institutional Review Board at the Dana-Farber/Harvard Cancer Center, and the procedures followed were in accordance with institutional guidelines. Informed consent was obtained from all subjects (n=11). Peripheral blood was withdrawn (~15 mL) from patients with ovarian cancer and centrifuged at 400 g for 15 minutes to separate plasma from red blood cells and buffy coat. 10 μL of plasma was used for each surface marker analysis.

CONCLUSION

This example demonstrated the use of magnetic electrochemical sensing to screen exosomes for biomarkers correlated with the progression of ovarian cancer, such as CD63.

A beneficial feature of the sensing system is the integration of vesicle isolation and detection into a single platform. The use of magnetic actuation simplifies vesicle isolation and subsequent assay steps, and the electrochemical sensing facilitates high-throughput screening and sensor miniaturization. The current study validated these concepts: i) a portable detection system was implemented with the capacity for parallel measurements; ii) the system enriched exosomes directly from blood, and profiled them for molecular information; iii) the entire system assay (i.e., exosome isolation, labeling, detection) was completed within 1 hour while consuming only 10 μL of plasma per marker. We also demonstrated the system's clinical potential by profiling EVs within blood collected from ovarian cancer patients.

The bead-based magnetic enrichment brings several advantages in the sensing system. First, the method provides a convenient way of concentrating signal sources on the electrodes, which enhances the detection sensitivity. Second, compared to the surface-based capture wherein antibodies are immobilized on the chip surface, the bead-based method is amenable to reliable and simpler conjugation chemistry, and benefits from faster binding kinetics between antibodies and exosomes. Third, the bead-bound vesicles could be readily recovered for downstream molecular analyses in tandem with the sensing sytem. For instance, bead-bound EVs can be eluted or lysed to profile their nucleic acid contents.

In this example, we focused on profiling CD63+ EV population (exosomes), which was motivated by two factors: i) the signal from CD63 capture was the highest among the tetraspanin markers tested; and ii) we and others have previously shown that ovarian cancer exosomes are enriched with CD63. The system's profiling found a high correlation in protein expression between CD63-positive exosomes and their parent cells; this result validated the potential use of CD63-positive exosomes as cellular surrogates. However, we note the exosome-capture strategy may be extended, considering that diverse EV types (e.g. CD63-negative) may exist in patient samples. Examining these populations could yield more precise information to capture tumor heterogeneity. The sensing method can be readily adopted for such purposes by changing capture antibodies.

We envision multiple directions to further advance the technology. First, the assay throughput can be improved by increasing the number of detection sites. Electrochemical sensing is ideally suited for such a scale-up: the sensing elements (electrodes) can be readily microfabricated into a large array format, and signals (electrical currents) can be read out by compact electronics with high-speed multiplexing. Second, the detection sensitivity could be improved by exploring new designs for electrochemical signal detection. The signal level is correlated with the surface area of a sensor and the amount of enzyme bound to target entities; thus, higher sensitivity can be achieved by using a nanostructured sensor surface or multi-label nanoparticles. Third, detection targets can be expanded to include other exosomal constituents. For example, exosomes carry various nucleic acids (e.g. mRNA, microRNA); analyzing nucleic acids along with exosomal proteins would provide more accurate snapshot of tumor states. Electrochemical sensing has been applied to detect a trace amount of nucleic acids (<1 pM) without PCR amplification. We expect similar approaches could be adopted to profile exosomal nucleic acids. The resulting iMEX could be a powerful clinical tool for affordable, scalable, and comprehensive exosome analyses, thereby deepening our insights into tumor biology and accelerating effective cancer management.

Example 2—Organ Rejection Testing

The purpose of this example was to demonstrate the use of magnetic electrochemical sensing to screen exosomes for biomarkers correlated with the transplanted kidney rejection.

Cell Culture

OV90, OVCAR3, OVCA420, and TIOSE6 cells were grown in RPM-1640 medium (Cellgro). CaOV3 were cultured in Dulbecco's modified essential medium (Cellgro). All media were supplemented with 10% fetal bovine serum (FBS) and penicillin-streptomycin (Cellgro). All cell lines were tested and were free of mycoplasma contamination (MycoAlert mycoplasma detection kit, Lonza, LT07-418).

EV Isolation from Cell Culture

We used a conventional method to harvest EVs from cell culture media. Cells at passages 1-15 were cultured in vesicle-depleted medium (with 5% depleted FBS) for 48 h. Conditioned medium from $10^7$ cells was collected and centrifuged at 300×g for 5 min. Supernatant was filtered through a 0.2 μm membrane filter (Millipore) and concentrated by 100,000×g for 1 h. After the supernatant was removed, the EV pellet was washed with PBS and centrifuged at 100,000×g for 1 h. The EV pellet was resuspended in PBS.

Biotinylation of Labeling Antibodies

Sulfo-NHS-biotin (10 mM, Pierce) solution in PBS was incubated with antibodies for 2 h at room temperature. Unreacted sulfo-NHS-biotin was removed using Zeba spin desalting column, 7K MWCO (Thermo Scientific). Antibodies were kept at 4° C. until use.

Enzyme-Linked Immunosorbent Assay

CD63 and IgG1 antibodies (Ancell) were diluted to 5 µg/mL in PBS and added to the Maxisorp 96-well plate (Nunc), respectively, for overnight incubation at 4° C. After being washed with PBS, a blocking solution with 2% BSA in PBS was added to the plate and incubated for 1 h at room temperature. Subsequently, ~$10^8$ exosomes in 100 µL of PBS were added to each well for 1 h incubation at room temperature. After the blocking solution was removed, antibodies (1 µg/mL) against various markers were added to each well and incubated at room temperature for 1 h. Unbound antibodies were triple washed with PBS. Streptavidin-horseradish peroxidase (HRP) molecules were added to the each well for 1 h at room temperature. After being washed out with PBS, chemiluminescence signals were measured.

iMEX Assay

Ten microliters of exosome-spiked PBS solution was mixed with 50 µL of the immunomagnetic bead solution for 30 min at room temperature. The bead concentration was determined according to the following criterion: $[C_b \times V_b \times 4\pi R_b^2]/[C_e \times V_e \times \pi R_e^2] > 100$, where $C_b$ and $C_e$ are the bead and the exosome concentrations, respectively; $V_b$ and $V_e$ are the volume of the bead solution and the exosome-spiked solution, respectively; $R_b$ and $R_e$ are the mean radius of beads and exosomes, respectively. This requirement ensured that sufficient bead surface was available for exosome capture. In our experiment condition, $R_e \sim 50$ nm, $R_b = 1.4$ µm, and $C_e \sim 10^{10}$/mL. Therefore, we adjusted the bead concentration to ~$10^8$/mL. The magnetic beads were separated from the solution with a permanent magnet and resuspended in 80 µL of PBS (1% BSA). After 5 s of vortexing, the beads were separated and resuspended in 80 µL of PBS (1% BSA). Ten microliters of antibodies of interest (20 µg/mL in PBS) was mixed with the beads for 30 min at room temperature. The magnetic beads were separated and washed as described before, and they were resuspended in 50 µL of PBS (1% BSA). Five microliters of streptavidin-conjugated HRP enzymes (1:100 diluted in PBS) was mixed with the beads for 15 min at room temperature. The magnetic beads were separated and washed as described before, and they were resuspended in 7 µL of PBS. The prepared bead solution and 20 µL of UltraTMB solution (Thermo-Fisher Scientific) were loaded on top of the screen-printed electrode. After 3 min, chronoamperometry measurement was started with the electrochemical sensor. The current levels in the range of 40-45 s were averaged.

EV Isolation from Clinical Samples

The study conducted was approved by the research institution's Institutional Review Board, and the procedures followed were in accordance with institutional guidelines. Informed consent was obtained from all subjects (n=xx). Urine sample was collected (~15 mL) from patients with kidney transplant and centrifuged at 400 g for 15 min to separate plasma from red blood cells and buffy coat. Ten microliters of plasma were used for each surface marker analysis.

Figure 28:
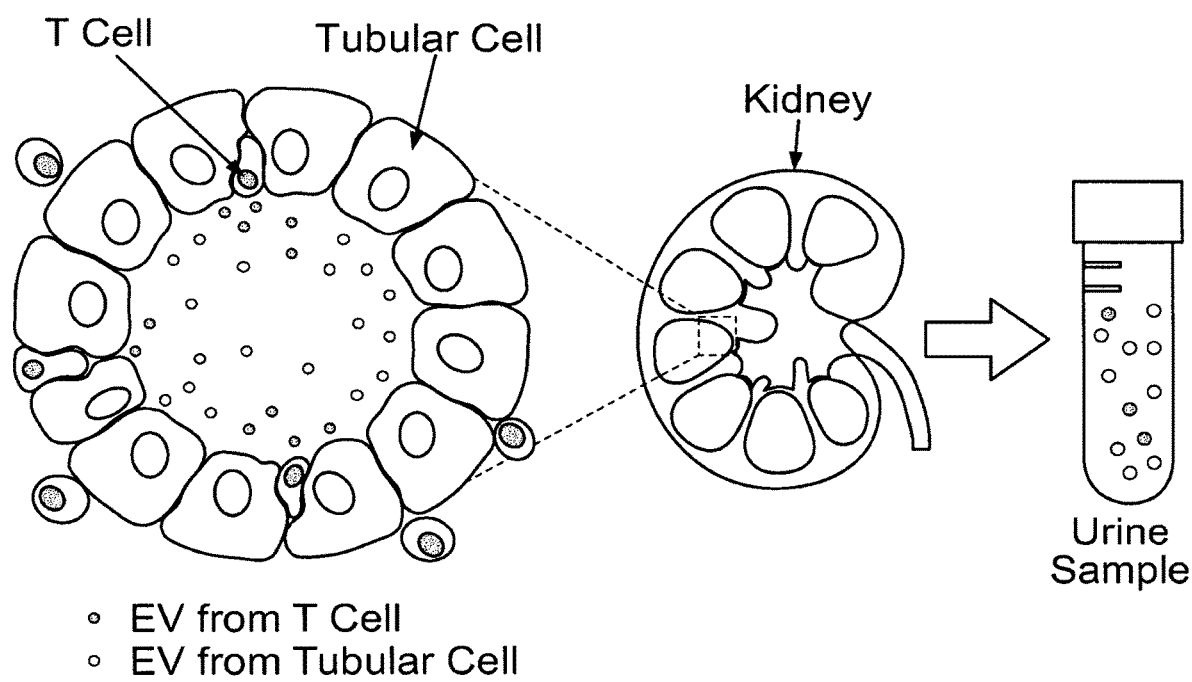
FIG. 28 is a schematic illustration of a T cell-derived extracellular vesicle (EV) secreted tubule in a kidney.
Figure 29:
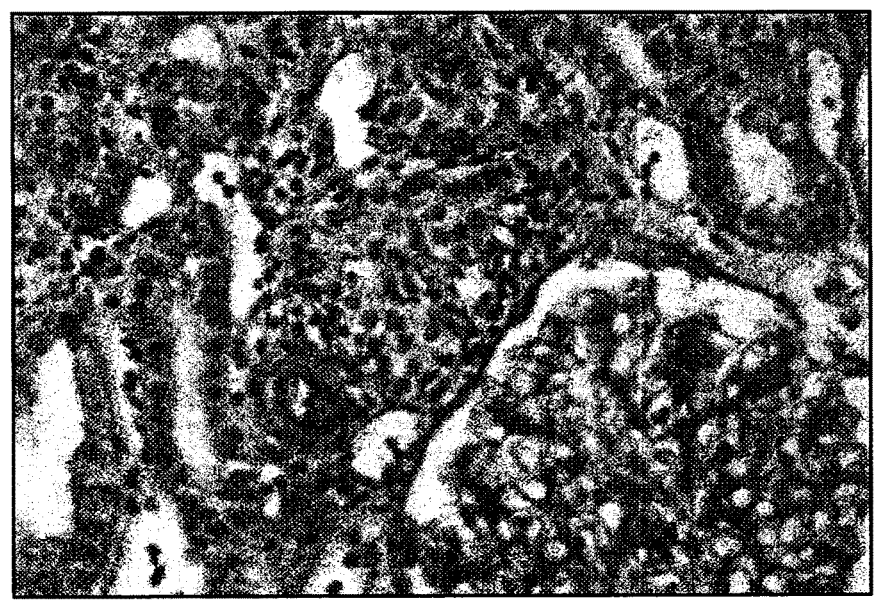
FIG. 29 shows histology of kidney transplant rejection patient biopsy samples.
Figure 30:
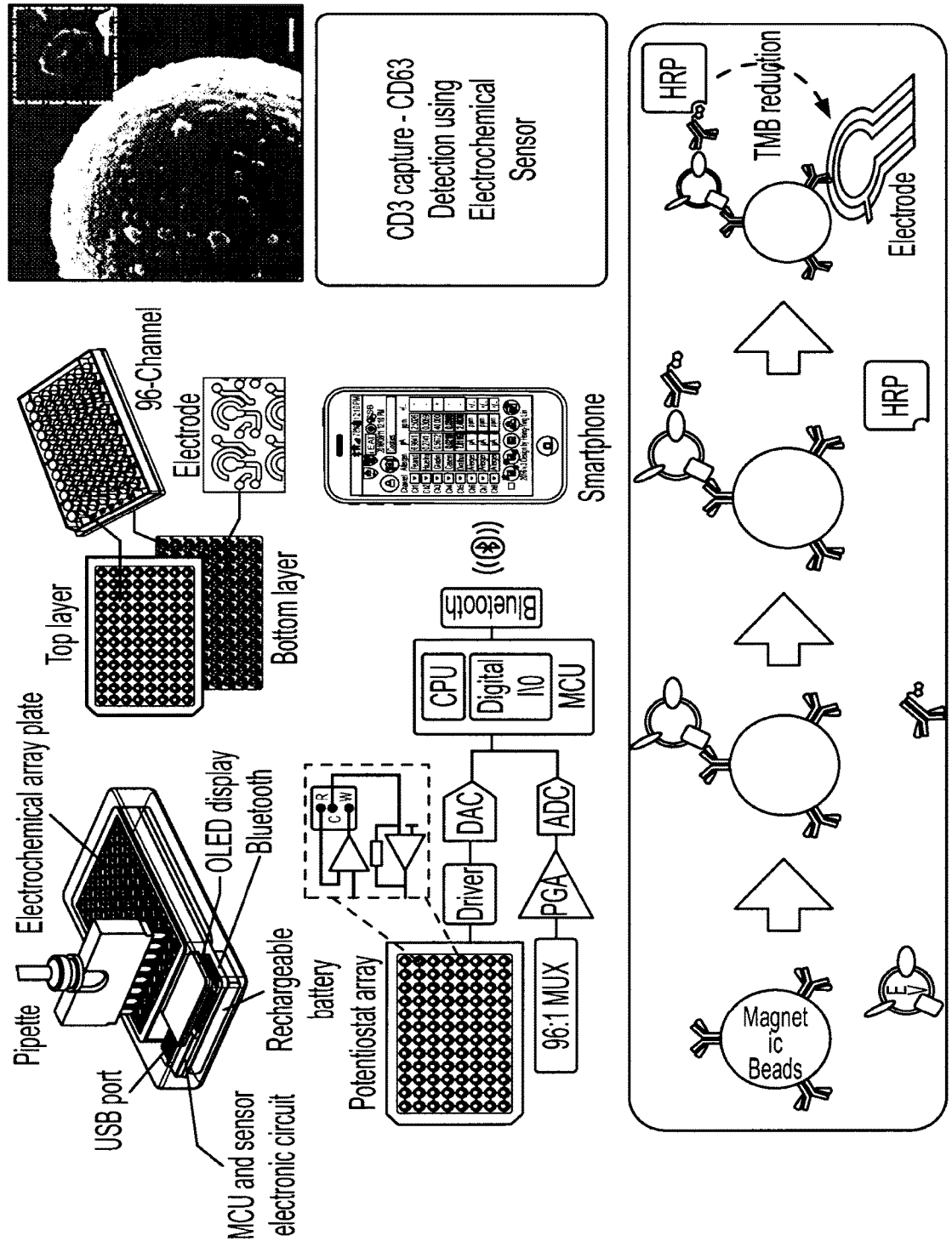
FIG. 30 shows a schematic of a 96 well plate format iMEX system for the detection of Jurkat T cell-derived extracellular vesicles, scanning electron microscopy (SEM) images of an EV captured by CD3 antibody-functionalized magnetic beads, titration curves of Jurkat derived EV detection by iMEX, and a schematic of the iMEX.

FIG. 28 is a schematic illustrate that T cell derived EVs secreted tubule in kidney. FIG. 29 shows histology of kidney transplant rejection patient biopsy samples. FIG. 30 shows a schematic of a 96 well plate format iMEX system for the detection of jurkat T cell derived exosome. The sensor can measure the signals from 96 samples simultaneously. Scanning Electron Microscopy shows EV captured by CD3 antibody functionalized magnetic beads. A schematic of the iMEX assay is also shown. EVs from jurkat cell or patient urine were captured by anti-CD3 antibody conjugated magnetic beads. Subsequent biotinylated anti-CD63 antibody and HRP enzyme labeling gave electrochemical signals.

Figure 31A:
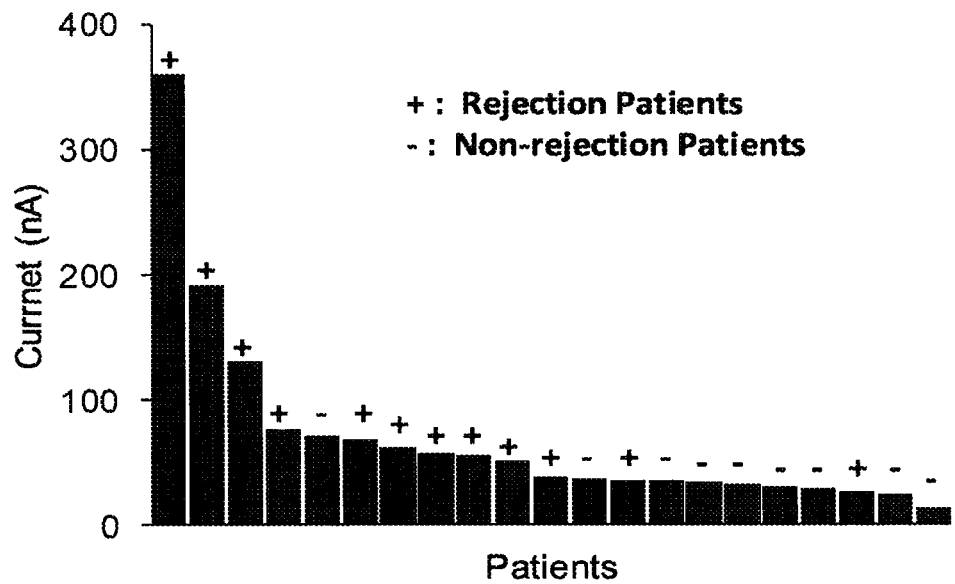
FIG. 31A shows the measured current when EVs with CD3 expression were detected with iMEX assay in a discovery set.
Figure 31B:
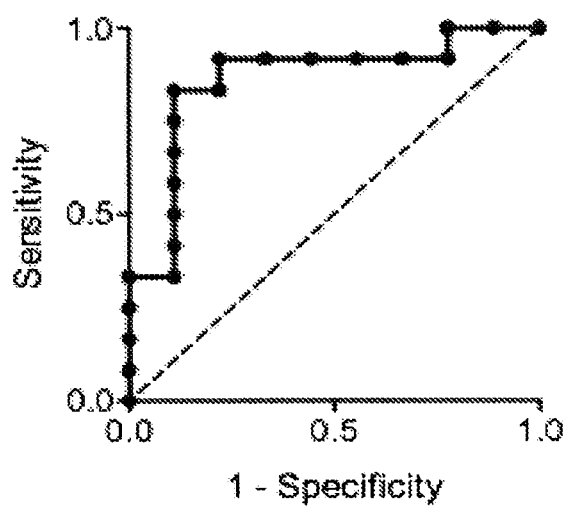
FIG. 31B shows a ROC curve used to determine the sensitivity, specificity and accuracy of CD3 marker in the discovery set.

FIG. 31A shows the measured current when EVs with CD3 expression were detected with iMEX assay in a discovery set. FIG. 31B shows a ROC curve used to determine the sensitivity, specificity and accuracy of CD3 marker in the discovery set.

FIG. 32A shows the measured current when EVs with CD3 expression were detected with iMEX assay in a validation set. FIG. 32B shows a ROC curve used to determine the sensitivity, specificity and accuracy of CD3 marker in the validation set.

CONCLUSION

This example demonstrates the use of magnetic electrochemical sensing to screen exosomes for biomarkers correlated with the transplanted kidney rejection as a means of detecting rejection at its early stages.

Example 3—Food Testing

The purpose of this example was to demonstrate the use of magnetic electrochemical sensing to detect the presence of allergens in food products.

Adverse food reactions, including food allergies, food sensitivities, and autoimmune reaction (like celiac disease) affect 5-15% of the population and remain a considerable public health problem requiring stringent food avoidance and, for emergency episodes, epinephrine availability. Avoiding problem foods is easier said than done, given today's reliance on prepared foods and out-of-home meals. We developed a portable, point-of-use technology for rapid exogenous food-antigen testing (referred to herein as "iEAT"). The system includes a disposable antigen extraction device coupled with an electronic keychain reader for rapid sensing and communication. We optimized the prototype iEAT system to detect five major food antigens in peanuts, hazelnuts, wheat, milk, and eggs. Antigen extraction and detection with iEAT requires less than 10 min and achieves detection sensitivies below 0.003 ppm, far lower than regulatory limits. When testing under restaurant conditions, we were able to detect hidden food antigens such as gluten in "gluten-free" food items. The small size and rapid, simple testing of the iEAT system will help not only consumers but also clinicians, the food industry and regulators enhance food safety More than 50 million Americans have a food reaction of some kind. Food allergies cost 25 billion dollars annually in the US alone. Even trace amounts of food antigens can trigger acute anaphylaxis, a potentially life-threatening hypersensitivity reaction requiring epinephrine injection. Although the results of immunotherapeutic trials have been encouraging, the primary approach continues to rely on food avoidance. The Food Allergen Labeling and Consumer Protection Act (FALCPA) mandates food labeling to inform customers about allergenic substances in products. Even so, mislabeling or cross-contamination in manufacturing continue to pose regulatory challenges. Furthermore, FALCPA only oversees packaged food, not food served in restaurants. Food labeling outside the US is less strict, and food allergies often affect travelers. Thus, the ability to rapidly test foods for common allergens is a major unmet need.

The system includes a disposable allergen extraction device and an electronic keychain reader for sensing and communication. The extraction kit captures and concentrates food antigens from dispersed food. Captured allergens are then quantified using the miniaturized key-chain reader. Overall, the iEAT system enables quantitative allergen detection in a short and actionable time frame (i.e., <10 min for the entire assay). We designed iEAT specifically to promote consumer-based operations: i) the extraction kit is simple to use, inexpensive and disposable; ii) detection is fast, reliable and accurate, and iii) embedded communication protocols allow users to record and upload information to a cloud server with time and locale stamps. We optimized the iEAT prototype to detect five representative allergens from wheat, peanut, hazelnut, milk, and egg white. The rapid iEAT assay achieved highly sensitivity, far-surpassing gold standard ELISA. We also show iEAT's practical use in surveying common foods for these allergens.

iEAT Assay

Figure 33A:
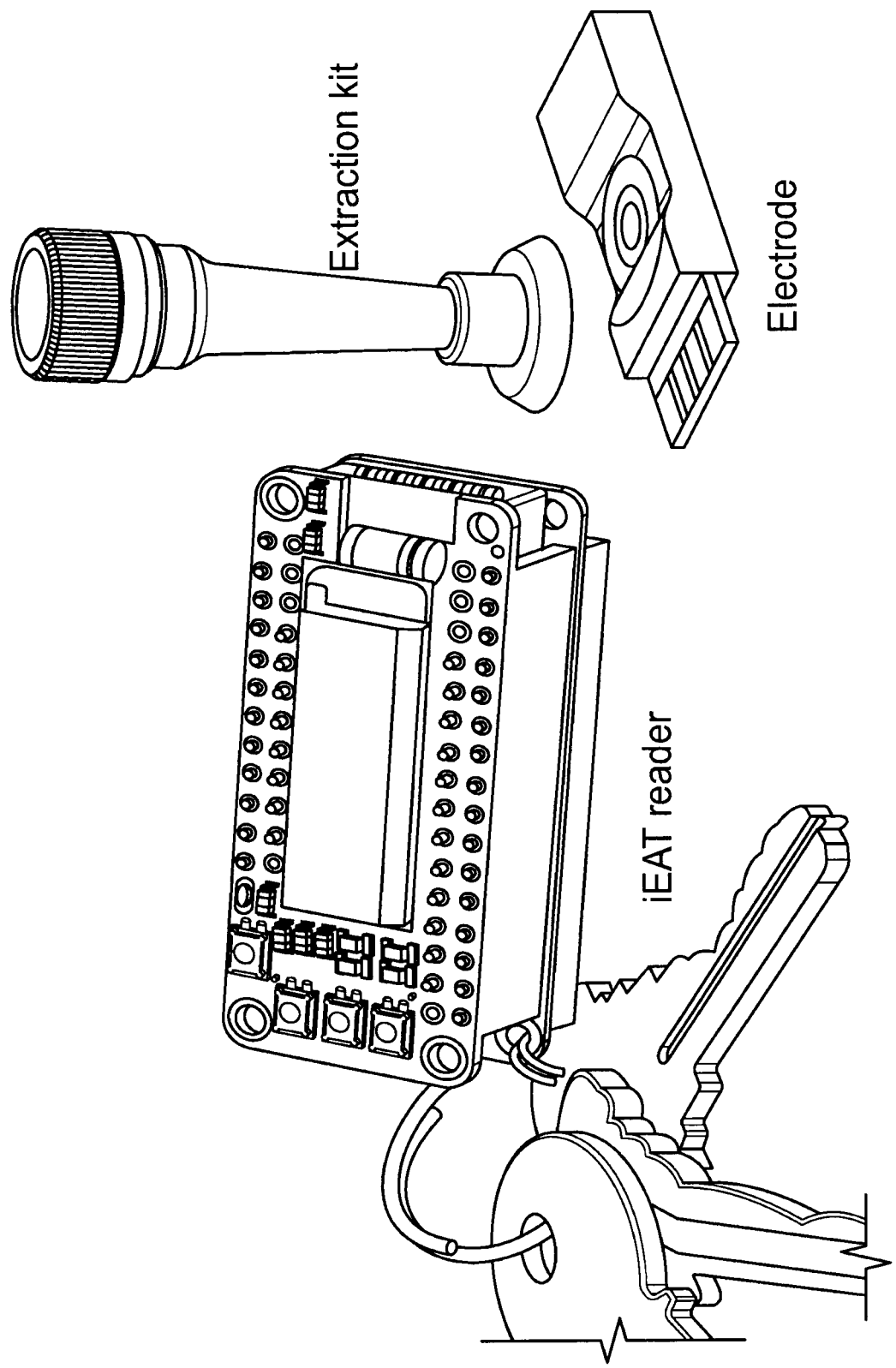
FIG. 33A magnetic electrochemical sensing system (integrated exogenous antigen testing system, iEAT).

FIG. 33A depicts the portable iEAT system including a keychain reader, an extraction kit, and a smartphone App, such as described herein with respect to FIGS. 6-9. The system including of a keychain-size detector, an electrode chip and a disposable kit for allergen extraction. The detector connects with a smartphone for system control and data upload to a cloud server.

Figure 33B:
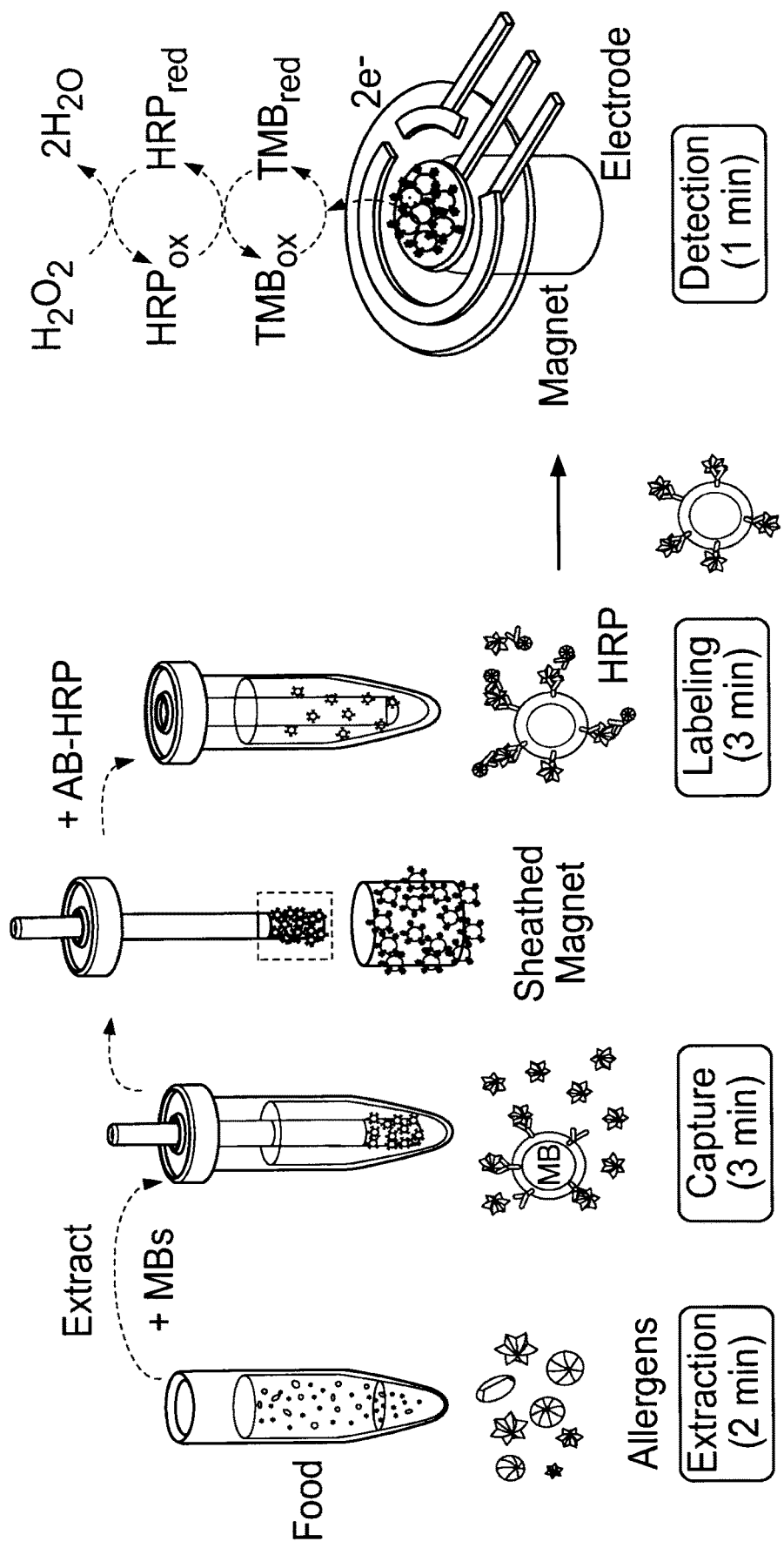
FIG. 33B is a diagram of an example iEAT assay technique.

The first step in sensing was extracting allergen via a specially-designed disposable kit that uses immunomagnetic enrichment (see FIG. 33B). Allergens were captured on magnetic beads and labeled with a second antibody conjugated with an oxidizing enzyme (horseradish peroxidase, HRP). A disposable kit has been developed to handle samples; the sheathed magnet collects and re-disperses MBs. When mixed with chromogenic electron mediators (3,3',5,5'-tetramethylbenzidine, TMB), the beads generated electrical current from TMB oxidation. The current was then measured by an electrode. The signal is amplified through the enzymatic reaction as well as the magnetic enrichment of MBs. The electrical detection scheme made it possible to perform quantitative measurements with a miniaturized electronic device. Furthermore, using magnetic beads as a solid substrate improved the assay performance in two ways.

First, the extraction process and sample handling was simplified via magnetic actuation. To enable portable operations, we designed a simple sheathed magnetic bar for bead collection and resuspension (see FIG. 8), which obviates the need for specialized equipment (e.g., centrifuge, pipettes). The extraction kit simplified the allergen extraction and labeling processes. A magnet was attached at the end of a glass stick and sheathed by a quartz tube. This assembly was inserted to a sample tube containing a mixture of food extraction fluid and immunomagnetic beads. The collected beads were easily transferred to different tubes for washing and labeling.

Second, electrochemical signals were amplified by magnetically concentrating beads on top of the electrode. For this we designed an electrode holder fitted with a small magnet (see FIG. 6D). The holder had a small magnet, one for each electrode, to concentrate magnetic beads. A holder for a single electrode is shown.

We designed the iEAT reader as a keychain-size device for easy portability (see FIGS. 6A-6C). The mini-reader not only detected and displayed results but also wirelessly communicated with smartphones via Bluetooth to transmit test results and other information to a cloud server for web-based data collection and sharing amongst users. The smartphone app communicated with the iEAT device through Bluetooth, and uploaded data to a cloud server. Functions included (i) taking photos of users and analyzed foods, (ii) setting detection channels (e.g., allergen types), (iii) displaying measurement results, (iv) tracking food intake, and (v) storing measurement time and location in a map.

Furthermore, this communication capability provides an extended user interface for system control, data storage, and wireless battery charging. The device houses multiple components including potentiostats for current measurements, a micro-controller unit (MCU) for signal processing, a mini display screen, a rechargeable battery, and a card-edge connector to insert an electrode board. This miniaturized device is a standalone unit, measuring electrical currents and displaying allergen concentrations according to preloaded lookup tables.

Figure 34:
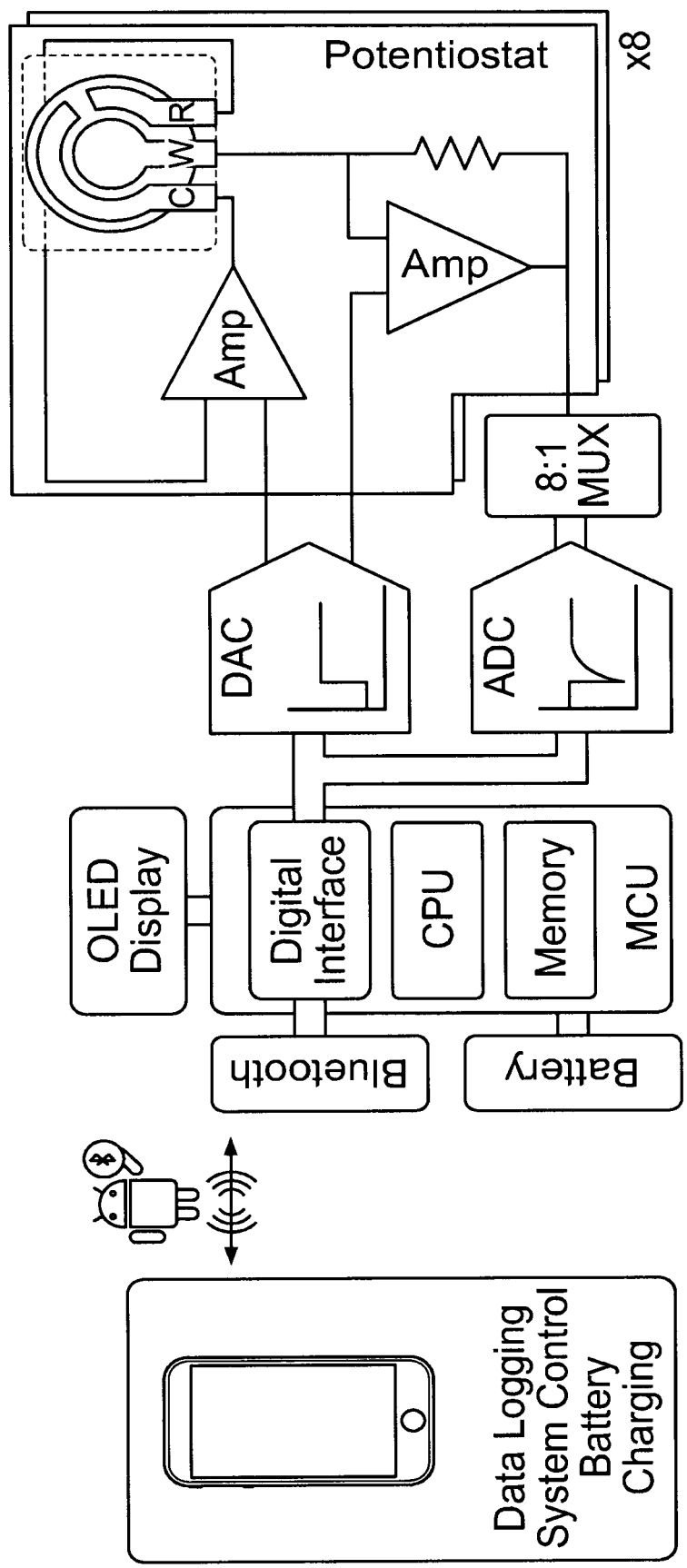
FIG. 34 is a schematic diagram of the iEAT system.

As shown in FIG. 34, the iEAT reader included custom-designed potentiostats connect to a digital-to-analog converter for potential control and an analog-to-digital converter for signal digitization. The MCU was programmed to measure electrical current from working (W) to counter (C) electrodes while keeping a constant potential between working and reference (R) electrodes. The circuit was designed to accommodate either a single electrode or an array of electrodes. For a single electrode, electrical contact occurred on the top side of the card-edge connector; for a multichannel array, contact occurred through the bottom side of the card-edge connector. The iEAT reader automatically sensed the operation mode (i.e., single or multichannel). For multichannel detection, the MCU sequentially polled electrodes through the multiplexer.

We benchmarked the iEAT performance against a commercial benchtop potentiostat (SP-200, Bio-Logic) using potassium ferrocyanide [$K_4Fe(CN)_6$] standards. We generated a $K_4Fe(CN)_6$ calibration curve for each system. Next, we measured test samples with varying $K_4Fe(CN)_6$ concentrations, and we obtained their concentrations from the calibration curves. We observed an excellent match between two systems ($R^2$=0.995; see FIG. 35). The iEAT reader also showed good precision: the coefficient of variations (CVs) from five repetitive measurements were <4.1%, comparable to CVs obtained with the benchtop system (<4.9%). The iEAT reader, however, had a much smaller form factor (5.5×2.5×2.4 $cm^3$, 35 g) than the benchtop system (38×21×17 $cm^3$, 6 kg) and was capable of 8 parallel measurements.

Antigen Extraction

We first optimized the antigen extraction protocol. Our goal was to minimize both extraction time and cost while maximizing recovery yield. We used five major protein antigens as extraction targets: gliadin (wheat), Ara h1 (peanut), Cor a1 (hazelnut), casein (milk), and ovalbumin (egg white). Mock meals were prepared by spiking a known amount (10 ppm) of protein into white rice. We tested three extraction buffers: 2-mercaptoethanol (2-ME), tris-(2-carboxyethyl)phosphine augmented with guanidine (TECP/GUA) and TECP with N-lauroylsarcosine (TECP/sarkosyl). The 2-ME reduction buffer is commonly used to extract protein from highly processed food but has a strong odor. We prepared TECP-based reducing agents as potential user-friendly alternatives.

Figure 36C:
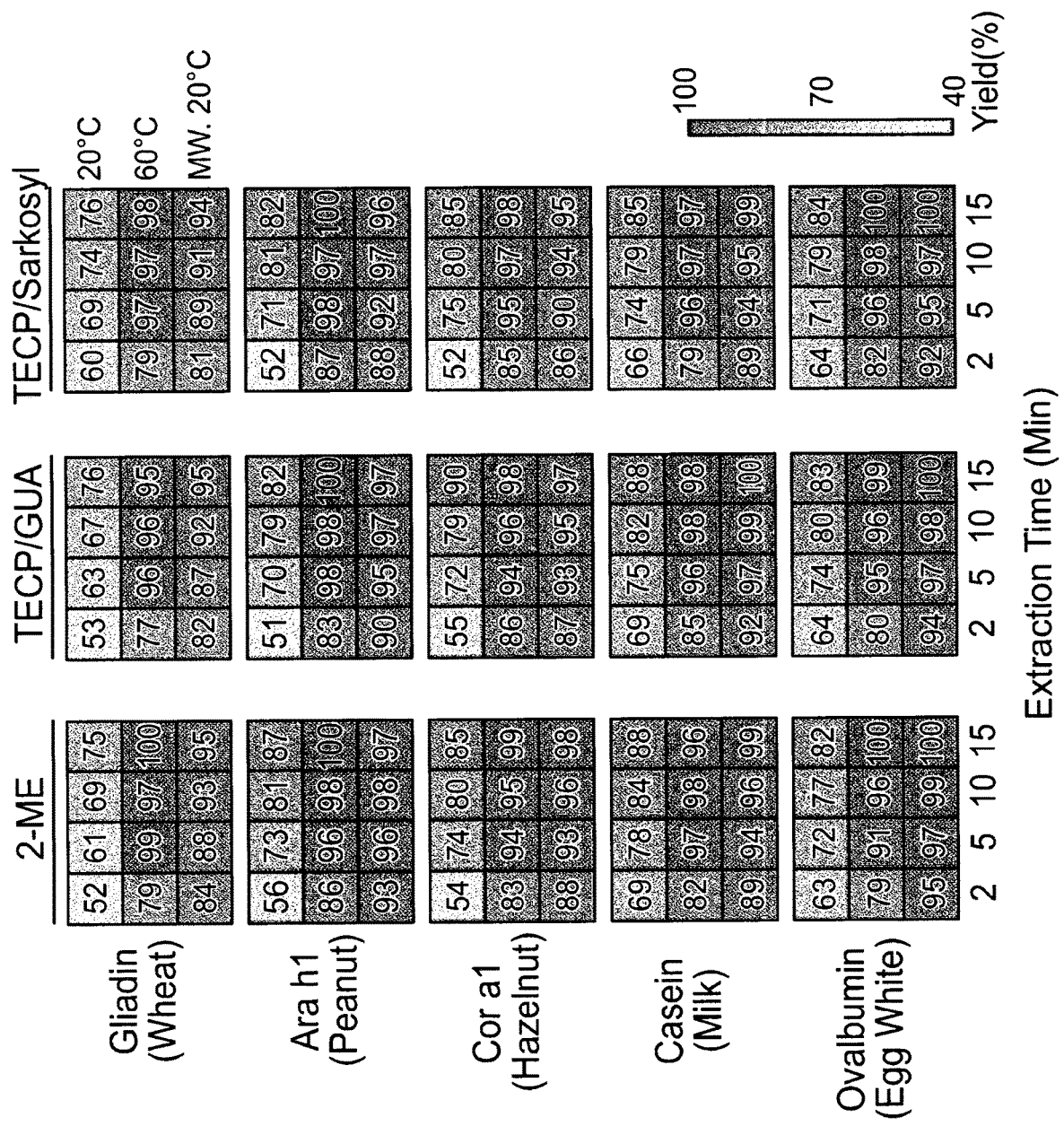

For a given extraction buffer, we changed the incubation time and temperature, and we monitored the recovery yield. FIG. 36A shows an example Ara h1 extraction with 2-ME buffer. The extraction was efficient even at room temperature; more than 60% of antigens were recovered within 2 minutes of incubation. The extraction yields increased with temperature. For example, after 20 seconds of heating in a microwave oven (1100 W), yields increased to 80% with 1 minute of incubation in the extraction buffer. All three extraction buffers showed similar performance for five tested antigens (see FIGS. 36B and 36C). We therefore opted to use the odorless, low-cost TECP/sarkosyl extraction buffer (see Table 1)

TABLE 1 iEAT detection limits for the five food antigens.

| Allergen | Limit of detection (ppm) | Action level 1 (ppm)* |
|---|---|---|
| Gliadin | 0.076 | 20 |
| Ara h1 | 0.007 | 8 |
| Cor a1 | 0.090 | 10 |
| Casein | 0.812 | 50 |
| Ovalbumin | 0.003 | 20 |

*A set of action levels was created by VITAL (Voluntary Incidental Trace Allergen Labeling). Action level 1 requires no labeling or declaration for food manufacturers.

We also built a small heating device (see FIG. 37) to speed up the extraction process. The extraction condition was set for 2 minutes incubation at ~60° C.

Measurement

To capture the predetermined antigens, we prepared immunomagnetic beads (2.8 μm in diameter) by conjugating monoclonal antibodies to magnetic beads. Control beads were conjugated to isotype-matched IgG antibodies. An optimal bead concentration, determined using peanut allergen titration, was $\sim 8 \times 10^6$ beads/mL (see FIG. 38A). Magnetic beads specific to peanut allergen (Ara h1) were used to detect 20 ppm Ara h1. Bead concentrations >107 mL−1 led to the signal saturation. The optimal bead concentration was set to 8×106 mL−1. Similar experiments were repeated for other allergens. The data are shown as mean±s.d. from duplicate measurements.

Following incubation at room temperature (3 minutes) with food extracts, beads were collected with the sheathed magnetic and transferred to fresh buffer for washing. Subsequently, the beads were labeled with an HRP-conjugated antibody (3 minutes at room temperature), washed and mixed with TMB for signal generation. The electrical current stabilized within 60 seconds after the reduction potential (−0.1 V) was applied (see FIG. 38B, dynamic current responses). The measured signal between 50 and 60 sec was averaged. The net current difference between the background and the targeted sample was used as an analytical measure. We therefore programmed the iEAT reader to average the current level between 50 to 60 seconds. Electrical current levels from control beads were about −110 nA across different allergens, and the current difference between targeted sample and background was defined as the net signal. The total assay time, including the allergen extraction, was <10 minutes.

To facilitate reagent storage and transport, we further lyophilized immunomagnetic beads and antibodies. We tested different lyophilization media (PBS, sucrose) and storage conditions (refrigeration, room temperature). There were no significant differences in reagent activities; all lyophilized reagents retained their activity (>96%) after four weeks in storage (see FIGS. 39A and 39B). With respect to FIG. 39B, immunomagnetic beads and detection antibodies were lyophilized either in PBS or sucrose. The lyophilized products were stored at room temperature or at 4° C., and were used to detect 10 ppm peanut allergen. The reagents retained their activity regardless of the excipient type and the storage conditions. All measurements were in duplicate, and the data are displayed as mean±s.d. Given its ready availability, we chose PBS as an excipient, and for ease of use, we chose ambient conditions for stored lyophilized reagents.

Analytical Performance

We next generated response curves, varying the target allergen dose (see FIG. 40A for Ara h1 and FIG. 40B for others); these curves were loaded to the iEAT reader as lookup tables. The iEAT assay was highly sensitive, precise and allowed robust allergen quantification. The limit of detection (LOD), defined as $3\sigma \cdot m^{-1}$ (where σ and m are the standard deviation and the slope of calibration curve, respectively), was >220-fold lower than the eliciting dose (ED) thresholds (see Table 1). The intra-assay variations, estimated by measuring three different concentrations of standard (1, 5 and 10 ppm) with six duplicates, were <5% (See FIG. 40C), and the inter-assay variations were <5%. For comparison, we also tested the same samples by ELISA. The iEAT results correlated well with ELISA measurements (see FIG. 40D, $R^2 = 0.995$). The iEAT assay, however, was much faster (10 minutes vs. 2 hours for ELISA). To test the assay specificity, we applied target probes to different allergen standards (5 ppm). As shown in FIG. 43E, specific signals were >20-fold larger than non-target samples.

Field Testing

Figure 41A:
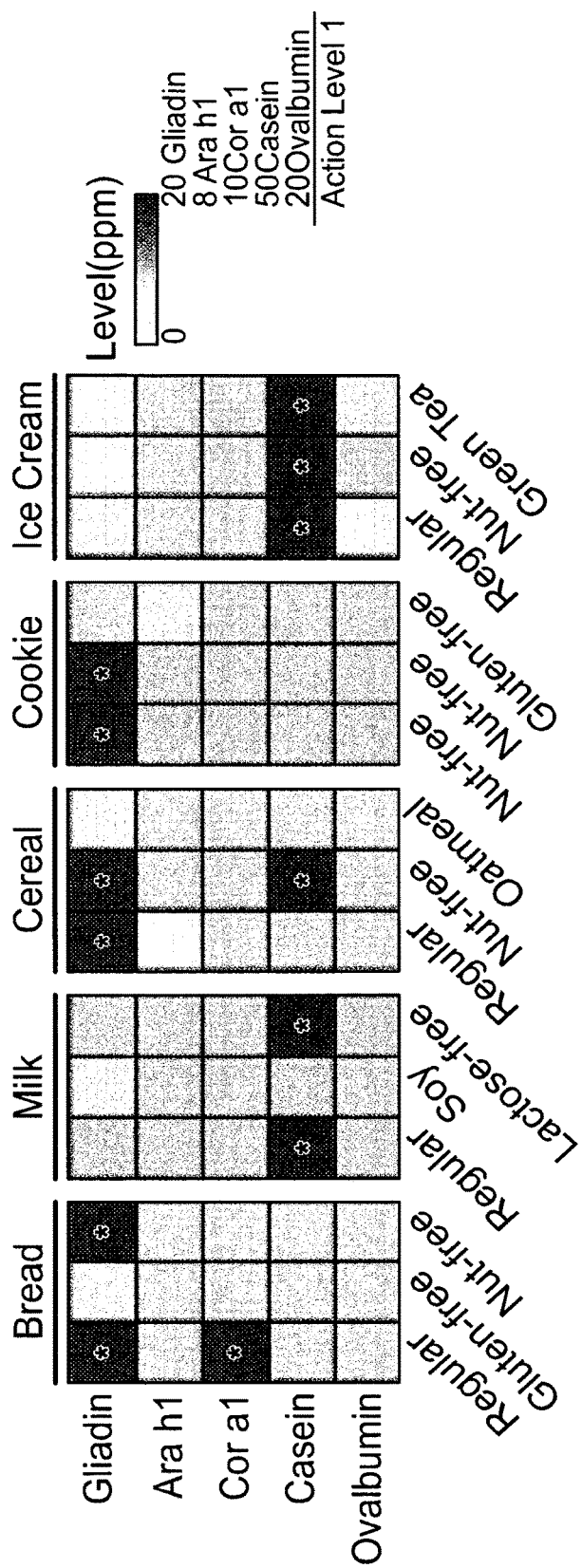
FIGS. 41A and 41B show profiling results obtained using the iEAT system.

We next applied the iEAT platform to testing consumer food products. We first tested a panel of packaged staple foods (bread, milk, cereal) and desserts (cookie, ice cream). Small portions of food (~1 g) were processed over 2 minutes, as described above, and extracts were assayed for gliadin, are Ara h1 (peanut), Cor a1 (hazelnut), casein (milk), and ovalbumin (egg white). The profiling results are summarized in FIG. 41A. As expected, products with specific labeling (e.g., "gluten-free," "nut-free") were largely devoid of the listed allergen. However, most products contained at least one unspecified antigen; for instance, brands of nut-free cookies contained gluten, whereas a gluten-free brand contained peanut allergen.

Figure 41B:
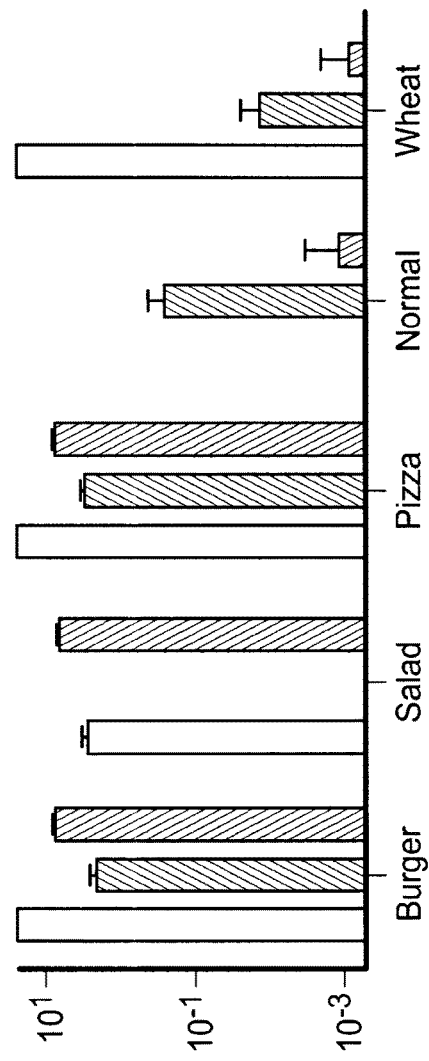

We next assayed foods (burger, salads with dressing, pizza, and beer) obtained from restaurants. The profiling results (see FIG. 41B) showed the expected allergens, such as gluten in hamburgers and pizza, but we also detected unexpected antigens contributed by food processing. For example, salad contained gluten, likely from the salad dressing. We also identified ovalbumin and casein in beer, which was not entirely surprising as egg-white is used to improve the foam characteristics, and casein is used to stabilize beer during the brewing process.

Utilizing iEAT's interface with a smartphone, we tracked personal dietary intake, recording antigens data with time stamps in a cloud server (see FIG. 41C). As one example, we surveyed gluten-free menu items from seven local restaurants and logged the results (e.g., food name, gluten contents) with locale information. Among "gluten-free" items, we observed a wide spectrum of antigen levels (1 ppm to >100 ppm); three items had gluten far exceeding the regulatory limit (see FIG. 41D, left). These results were then used to create an evidence-based restaurant map (see FIG. 41D, right). These maps can be shared and expanded to include other antigens for personalization.

Materials

The following chemical and biochemical reagents were used as received: superparamagnetic beads ($6.7 \times 10^7$ beads/mg, Dynabeads® M-270 Epoxy, Invitrogen); bovine serum albumin (≥98%, BSA, Sigma); ovalbumin (OVA, InvivoGen), gliadin from wheat (Sigma); casein from bovine milk (Sigma); sulfuric acid (1N, Fluka); Pierce® high sensitivity streptavidin-horseradish peroxidase (strep-HRP, Thermo Scientific); monoclonal mouse $IgG_1$ (1.0 mg/mL, Ancell); monoclonal mouse $IgG_{2a}$ (1.0 mg/mL, Ancell); gliadin peptide antibody (14D5, 1.0 mg/mL, monoclonal mouse $IgG_{2a}$, Enzo Life Sciences); anti-gliadin antibody (15.5 mg/mL, conjugated to HRP, polyclonal rabbit IgG, abcam; conjugated to HRP from MIoBS's gliadin ELISA kit); ovalbumin antibody (6C8, 0.98 mg/mL, monoclonal mouse IgGi, Thermo Fisher); anti-OVA polyclonal antibody (conjugated to HRP, from MIoBS's egg ovalbumin ELISA kit); naturally purified *Arachis hypogaea* allergen (peanut protein Ara h1, Indoor Biotechnologies); anti-Ara h1 antibody (2C12, 2.7 mg/mL, monoclonal mouse $IgG_1$, Indoor Biotechnologies); biotinylated anti-Ara h1 antibody (2F7, monoclonal mouse $IgG_1$, Indoor Biotechnologies); peanut standard (Diagnostic Automation, Inc.), rabbit anti-bovine casein polyclonal antibody (2 mg/mL, AGRO-BIO); anti-casein polyclonal antibody (conjugated to HRP, from MIoBS's casein ELISA kit); hazelnut protein standard (RIDASCREEN® hazelnut ELISA kit and Diagnostic Automation, Inc.); rabbit polyclonal antisera to hazelnut protein (anti-hazelnut antibody, Accurate Chemical & Scientific Corporation); HRP-conjugated anti-hazelnut antibody (RIDASCREEN® hazelnut ELISA kit); sucrose (≥99.5%, Sigma); 1-Step ultra 3,3',5,5'-tetramethylbenzidine (TMB) ELISA substrate solution (Thermo Scientific); Tris(hydroxymethyl)aminomethane hydrochloride (Tris-HCl, ≥99%, Sigma); 2-mercaptoethanol (2-ME, ≥99%, Aldrich); guanidine hydrochloride (GUA, ≥99%, Sigma); sodium dodecyl sulfate (SDS, ≥99%, Sigma-Aldrich); N-Lauroylsarcosine (≥95%, Sigma); Tris(2-carboxyethyl)phosphine hydrochloride (TCEP, ≥98%, Aldrich); Tween 20 (Sigma) and potassium ferrocyanide (≥98.5%, Sigma-Aldrich). Unless otherwise stated, all solutions were prepared at 25° C., used ultrapure water with an electrical resistivity of 18.2 MΩ.cm and were stored at 4° C.

Fabrication of TEAT Reader

The keychain detector (5.5×2.5×2.4 cm$^3$) was built around a microcontroller unit (MCU, ATSAMD21G18, Atmel Corporation). A digital-to-analog converter (DAC8552, Texas Instruments) was used to set the potential between the reference and the working electrodes. For the current measurements, a digital-to-analog converter (ADS1115, Texas Instruments) and a potentiostat were connected to MCU's peripheral interface. The potentiostat included of two operational amplifiers (AD8608, Analog Devices): one amplifier maintains the potential difference between a working electrode and a reference electrode, and the other one works as a transimpedance amplifier to convert a current to a voltage signal. Other peripherals include a communication module (Bluefruit EZ-Link) for Bluetooth connection with external devices, a display module, and a rechargeable battery.

Smartphone Application

Using MIT App Inventor 2, we created an Android application to facilitate system operation and data recording. The application allowed users to control the device, take sample photos, and record measurement details (time stamps, current value, estimated analyte concentration and GPS location). The data were stored with cloud storage (Google Drive).

Preparation of Antibody-Tagged Immunomagnetic Beads (Ab-MBs)

Magnetic beads (~3.4×10$^8$) were resuspended in 1 mL sodium phosphate buffer. The bead solution was briefly vortexed, and the beads were collected by placing a magnet. The supernatant was discarded. This washing step was repeated twice. Next, beads were mixed with ~100 μg capture antibody or reference IgG with 1 M ammonium sulfate in sodium phosphate buffer. The total volume was 300 μL, making the bead concentration ~1.1×10$^9$ beads/mL. The bead solution was incubated for 16 hr at 4° C. with slow tilt rotation to avoid bead settling. The surface epoxy groups of magnetic beads allowed for direct covalent binding of antibodies via primary amino groups. Afterwards, the coated beads were collected and washed with 1 mL PBS three times. The prepared Ab-MBs were then resuspended in 200 μL PBS, 1% BSA, which was used as a stock solution.

Lyophilization of Immunomagnetic Beads and Detection Antibody

Sucrose and PBS were used in preparing the lyophilization of Ab-MBs and antibodies. An amount of 300-fold higher molar concentration of sucrose (in PBS) with respect to antibody concentration or same volume of PBS solvent (as preparing sucrose) was added into Ab-MB or antibody stock solutions. The mixture was frozen in liquid nitrogen and then dried in a VirTis Freezemobile 25EL Freeze Dryer (SP Scientific). The lyophilized reagents were stored at room temperature or at 4° C. and reconstituted before use by adding 200 μL of ultrapure distilled water.

Antigen Standards

We used white rice flour as a model food matrix. 1.0 g rice flour was prepared in 10 mL PBS and boiled to make a homogeneously mixed solution. We then added each of five allergens (gliadin, Ara h1, Cor a1, casein, ovalbumin) into the rice solution.

Extraction Buffers:

Three extraction buffers were prepared: (1) 50 mM Tris-HCl, 150 mM NaCl, 0.05% Tween®20, 250 mM 2-ME, 2M GUA, 1% SDS, pH 7.4; (2) 50 mM Tris-HCl, 150 mM NaCl, 0.05% Tween®20, 20 mM TCEP, 2M GUA, pH 7.4; (3) 50 mM Tris-HCl, 150 mM NaCl, 0.05% Tween®20, 5 mM TCEP, 2% N-lauroylsarcosine, pH 7.4.

Food Sample Preparation

Food samples were obtained from local supermarkets and restaurants. Food samples (~1 g) were cut into small pieces and mixed with 19 mL extraction buffer. Following the allergen extraction, the supernatant was taken as a sample extract for subsequent iEAT detection. An amount of allergen in a sample was reverted by multiplying 20 dilution fold.

iEAT Assay

20 μL of food extract was mixed with 50 μL Ab-MB solution, and incubated for 3 min at room temperature. For washing, the beads were collected using a glass-sheathed magnetic bar and released in PBS (100 μL). The beads were then incubated with HRP-conjugated antibodies (10 μL) for 3 min and washed as described above. The HRP-bead complex was mixed with TMB substrate, and was loaded on the electrode. After 1 min, the chronoamperometry measurement was started. The current levels between 50~60 sec were averaged.

Enzyme-Linked Immunosorbent Assay (ELISA)

The stock capturing antibody and reference IgG antibody were diluted to ~3 μg/mL in carbonate-bicarbonate buffer (15 mM $Na_2CO_3$, 35 mM $NaHCO_3$, pH 9.6) and added to 96-well polystyrene sterile flat bottom microplates (100 μL/well) for overnight incubation at 4° C. The coated plates were washed three times with PBS with 0.05% Tween 20 (PBST) to remove unbound antibody. Then PBS with 1% BSA was added (100 μL/well) to block unoccupied binding sites. Plates were rinsed three times with PBST. Allergen standards and sample extracts were dispensed (100 μL/well) into plate wells in duplicate for 1 hr incubation at room temperature. Plates were washed three times with PBST.

Then a 100 μL aliquot of biotinylated detection antibody was added and incubated for 1 hr at room temperature. After washing three times with PBST, 100× diluted strept-HRP solution was filled (100 μL/well) for 30 min at room temperature. Plates were rinsed three times with PBST. The chemiluminescence signal was developed by adding 100 μL TMB substrate. After 10 min incubation at room temperature, 100 μL sulfuric acid (1N) was added to each well to stop the enzyme reaction. The optical absorbance of each well was measured at 450 nm using a plate reader (TECAN).

Statistical Analysis

All data obtained were presented as mean±standard deviation (SD). Statistical analyses were performed using GraphPad Prism 6. A p-value of under 0.05 was considered significant.

Discussion

We developed the point-of-care food testing system (iEAT) to sensitively detect multiple food antigens, clear "safe" foods, eliminate unnecessary avoidance and thus empower consumers. We further envision the system being used by the food industry, food reactions clinics and regulators. The signal detection, based on electrochemical reaction, is fast, scalable, well-suited to compact electronic devices and amenable to multiplexing. We prototyped the keychain reader to be operable as a standalone that can also be charged wirelessly and enable bluetooth communication with the cloud. The device is relatively inexpensive, and the assay cost was ~$3 per antigen in the current device. With scale-up and the ability to produce lyophilized kits, we expect these costs would decrease considerably. With these features, the iEAT system closely aligns with the WHO guideline for point-of-use devices, ASSURED, which is defined as affordable, sensitive, specific, user-friendly, rapid and robust, equipment free (i.e., no large electricity-dependent instruments) and deliverable.

We chose to quantify five representative model antigens that are commonly found in consumer foods and responsible for the majority of food reactions. While these antigens were chosen for proof-of-principle, many other potential antigens remain such as those in shellfish (shrimp, lobster), finned fish (tuna, salmon), tree nuts (walnuts, pecan, cashew), pollen and fruits, among others. It would be relatively straightforward to add these and other allergens to the detection list. The iEAT reader features both a single and a multichannel electrode, and the latter can measure eight allergens simultaneously. Sequential measurements or scaling up the channel number are both feasible ways to allow broader testing.

While we focused on specific protein antigens, the current assay format could also be modified to detect small molecules, toxins or nucleic acids by changing affinity ligands (e.g., aptamers, oligonucleotides); creating detection panels for food safety (e.g., pesticides) and for food-source identification (e.g., DNA-based testing). The device could have many interesting applications, such as verifying food origins, confirming the absence of contaminants or supporting dietary restrictions for religious purposes. These and other applications could be further enhanced through system integration, for example, by developing disposable fluidic cartridges to simplify sample processing. Irrespective of the specific application, we envision that the portable iEAT technology will allow for more rigorous and evidence-based analysis of food products, enhance consumer protection, reduce accidental allergy exposure, and identify problems in our food supply chain.

OTHER EMBODIMENTS

While this specification contains many details, these should not be construed as limitations on the scope of what may be claimed, but rather as descriptions of features specific to particular examples. Certain features that are described in this specification in the context of separate implementations can also be combined. Conversely, various features that are described in the context of a single implementation can also be implemented in multiple embodiments separately or in any suitable sub-combination.

A number of embodiments have been described. Nevertheless, it will be understood that various modifications may be made without departing from the spirit and scope of the invention. Accordingly, other embodiments are within the scope of the following claims.

What is claimed is:

1. A method of detecting a presence of a target analyte in a first fluid sample, the method comprising:
   providing a plurality of magnetic beads to a first fluid sample, wherein the plurality of magnetic beads comprises first binding moieties that specifically bind to the target analyte;
   allowing the plurality of magnetic beads to bind to the target analyte within the first fluid sample;
   transferring the magnetic beads from the first fluid sample to a second fluid sample, wherein the second fluid sample comprises second binding moieties that specifically bind to the target analyte, and wherein the second binding moieties are bound to a reactive enzyme;
   allowing the second binding moieties within the second fluid sample to bind to the target analyte bound to the first binding moieties of the magnetic beads;
   combining the second fluid sample comprising the plurality of magnetic beads and the second binding moieties with an electron mediator solution to obtain a third fluid sample;
   providing the third fluid sample to a first sample detection region of a device comprising a plurality of sample detection regions, wherein each sample detection region is arranged on a different corresponding set of electrodes, and wherein each set of electrodes is electrically coupled to a different corresponding potentiostat of a plurality of potentiostats;
   inducing an oxidation-reduction reaction between electron mediators within the third fluid sample and the reactive enzyme, wherein a signal produced by a first potentiostat of the plurality of potentiostats is due to the oxidation-reduction reaction; and
   monitoring a plurality of outputs of the plurality of potentiostats, to determine a presence of the target analyte,
   wherein monitoring the plurality of outputs of the plurality of potentiostats comprises
      performing simultaneous polling of the plurality of outputs of the plurality of potentiostats,
      selecting measurement data from one or more outputs of the plurality of outputs of the plurality of potentiostats, and
      analyzing, by a microcontroller unit, the selected measurement data to obtain analyzed data about the third fluid sample; and
   outputting, from the microcontroller unit, the analyzed data about the third fluid sample to a display.

2. The method of claim 1, wherein inducing the oxidation-reduction reaction comprises applying an electrical potential between a first electrode and a second electrode such that the oxidation-reduction reaction occurs, wherein the second electrode is electrically coupled to a corresponding potentiostat.

3. The method of claim 2, wherein performing simultaneous polling of the plurality of outputs of the plurality of potentiostats comprises, for each potentiostat of the plurality of potentiostats, measuring a voltage or current from a corresponding electrode coupled to the potentiostat, wherein the voltage or current from the corresponding electrode is indicative of a presence and/or prevalence of the target analyte in a corresponding sample-detection region associated with the potentiostat.

4. The method of claim 1, wherein the reactive enzyme comprises horseradish peroxidase (HRP) and the electron mediator solution comprises 3,3',5,5'-tetramethylbenzidine (TMB).

5. The method of claim 1, wherein the target analyte comprises extracellular vesicles.

6. The method of claim 5, wherein the extracellular vesicles comprise exosomes.

7. The method of claim 1, wherein the target analyte comprises any one of CD24, EpCAM, CA125, EGFR, HER2, MUC1, CD44, CD44v6, CEA, Mesothelin, Trop2, GPC1, WNT2, Grp94, SSTR2, EGFRv3, IDH1-R132, GPA33, KRAS, CD166, CD133, MET, B7H3, CD63, CD9, and CD81 biomarkers.

8. The method of claim 5,
wherein analyzing the selected measurement data to obtain analyzed data about the third fluid sample comprises comparing data from the first potentiostat to a reference level to determine whether the data from the first potentiostat is above or below the reference level; and
diagnosing the presence or absence of a cancer within a patient based on the comparison.

9. The method of claim 1, wherein the target analyte comprises immune cell markers.

10. The method of claim 9, wherein the immune cell markers comprise CD2, CD3, CD45, CD52, HLA-ABC, CD81, CXCL10, or CXCL9 biomarkers.

11. The method of claim 5,
wherein analyzing the selected measurement data to obtain analyzed data about the third fluid sample comprises:
comparing data from the first potentiostat to a reference level to determine whether the data from the first potentiostat is above or below the reference level; and
diagnosing whether or not a patient has rejected an organ transplant based on the comparison.

12. The method of claim 1, wherein the first fluid sample comprises blood or urine.

13. The method of claim 1, wherein the target analyte comprises a protein, a cell, a peptide, a lipid, a toxin, nucleic acides, microbes, food antigens, or a metabolite.

14. The method of claim 1, further comprising:
combining a food sample with an extraction buffer to provide the first fluid sample; and
incubating the food sample with the extraction buffer to extract the target analyte from the food sample.

15. The method of claim 1,
wherein analyzing the selected measurement data to obtain analyzed data about the third fluid sample comprises comparing data from the first potentiostat to a reference level to determine whether the data from the first potentiostat is above or below the reference level; and
making a diagnosis, administering a treatment to a patient, or both making a diagnosis and administering a treatment to a patient based on the comparison.

16. The method of claim 1,
wherein analyzing the selected measurement data to obtain analyzed data about the third fluid sample comprises comparing data from the first potentiostat to a reference level to determine whether the data from the first potentiostat is above or below the reference level; and
diagnosing the presence or absence of an allergen in a food product based on the comparison.

17. The method of claim 16, wherein the allergen is gliadin, Ara h1, Cor a1, Casein, or Ovalbumin.

18. The method of claim 1, further comprising exposing the third fluid sample to a magnetic field to retain the plurality of magnetic beads within the third fluid sample next to a first electrode, wherein the first electrode is electrically coupled to the first potentiostat.

19. The method of claim 1, wherein transferring the magnetic beads comprises:
immersing a sheath within the first fluid sample;
placing a magnet within the sheath that is immersed within the first fluid sample, such that the magnetic beads adhere to the sheath;
removing the sheath containing the magnet from the first fluid sample; and
immersing the sheath containing the magnet in the second fluid sample.

20. The method of claim 1, wherein analyzing the selected measurement data comprises normalizing the selected measurement data using a reference value.

21. The method of claim 1, wherein outputting the analyzed data about the third fluid sample to a display comprises displaying one or more geographical locations where the target analyte was collected.

22. The method of claim 1, wherein the outputs of the potentiostats are coupled to a multiplexer, and wherein selecting measurement data from the one or more outputs of the plurality of potentiostats comprises selectively retrieving the measurement data from the multiplexer.

23. The method of claim 1, wherein performing simultaneous monitoring of the outputs of the plurality of potentiostats comprises automatically changing an amplification gain of the measurement data.

24. The method of claim 1, wherein the plurality of sample detection regions and the corresponding set of electrodes are located on a probe card that is removably attachable from a housing unit comprising the microcontroller unit.

25. The method of claim 24, further comprising attaching the probe card to the housing unit so that the set of electrodes are electrically coupled to the plurality of potentiostats.

26. The method of claim 25, comprising transmitting, to the probe card, a signal identifying a particular probe on the probe card.

27. The method of claim 1, comprising:
receiving, from a graphical user interface, an input identifying a particular type of analyte to be analyzed, wherein selecting the measurement data from the one or more of the outputs of the plurality of potentiostats is performed in response to receiving the input identifying the particular type of analyte.

28. The method of claim 1, wherein performing simultaneous polling of the plurality of outputs of the plurality of potentiostats, respectively, comprises rapidly polling the plurality of outputs of the plurality of potentiostats.

* * * * *

UNITED STATES PATENT AND TRADEMARK OFFICE
CERTIFICATE OF CORRECTION

PATENT NO. : 11,125,745 B2  
APPLICATION NO. : 16/073540  
DATED : September 21, 2021  
INVENTOR(S) : Hakho Lee et al.

Page 1 of 1

It is certified that error appears in the above-identified patent and that said Letters Patent is hereby corrected as shown below:

In the Claims

Column 43, Claim 13, Line 51:
Delete "acides," and Insert --acids,--

Signed and Sealed this
Fourth Day of January, 2022

Drew Hirshfeld
*Performing the Functions and Duties of the*
*Under Secretary of Commerce for Intellectual Property and*
*Director of the United States Patent and Trademark Office*